United States Patent
Ma et al.

(10) Patent No.: US 7,202,246 B2
(45) Date of Patent: Apr. 10, 2007

(54) SPIRO-RIFAMYCIN DERIVATIVES TARGETING RNA POLYMERASE

(75) Inventors: Zhenkun Ma, Dallas, TX (US); In Ho Kim, Lewisville, TX (US); Jing Li, Dallas, TX (US)

(73) Assignee: Cumbre Pharmaceuticals Inc., Dallas, TX (US)

( * ) Notice: Subject to any disclaimer, the term of this patent is extended or adjusted under 35 U.S.C. 154(b) by 0 days.

(21) Appl. No.: 11/147,520

(22) Filed: Jun. 8, 2005

(65) Prior Publication Data

US 2005/0277633 A1    Dec. 15, 2005

Related U.S. Application Data

(60) Provisional application No. 60/578,405, filed on Jun. 9, 2004.

(51) Int. Cl.
  *C07D 225/04*  (2006.01)
  *A61K 31/495*  (2006.01)
  *A61P 31/04*   (2006.01)

(52) U.S. Cl. .................. 514/250; 540/453; 540/457
(58) Field of Classification Search ............... 540/453, 540/457; 514/250
  See application file for complete search history.

(56) References Cited

U.S. PATENT DOCUMENTS

| 4,219,478 A | 8/1980 | Marsili et al. |
| 4,341,785 A | 7/1982 | Marchi et al. |
| 4,690,919 A | 9/1987 | Yamane et al. |
| 4,859,661 A | 8/1989 | Kano et al. |
| 4,965,261 A | 10/1990 | Kanoo et al. |
| 4,983,602 A | 1/1991 | Yamane et al. |

OTHER PUBLICATIONS

Farr, B. M.; "Rifamycins"; Principles and Practice of Infectious Diseases; Mandell, G. L., Bennett, J. E., Dolin, R., Eds.; Churchhill Livingstone: Philadelphia, pp. 348-361.

Marchi, E., et al; "4-Deoxypyrido[1',2':1,2]imidazo[5,4-c]rifamycin SV Derivatives. A new Series of Semisynthetic Rifamycins with High Antibacterial Activity and Low Gastroenteric Absorption";, J. Med Chem, vol. 28, pp. 960-963, 1985.

*Primary Examiner*—Bruck Kifle
(74) *Attorney, Agent, or Firm*—Jackson Walker L.L.P.

(57) ABSTRACT

Compounds of the current invention relate to rifamycin derivatives having antimicrobial activities, including activities against drug-resistant microorganisms. More specifically, compounds of the current invention relate to a series of novel spiro rifamycin derivatives which have demonstrated potent antimicrobial activity.

34 Claims, 6 Drawing Sheets

Scheme 1

1. X = H; rifamycin S
2. X = Br: 3-bromo rifamycin S

Scheme 2

Scheme 4

Scheme 5

SPIRO-RIFAMYCIN DERIVATIVES TARGETING RNA POLYMERASE

RELATED APPLICATIONS

This application claims priority to U.S. Provisional Patent Application Ser. No. 60/578,405, entitled "Spiro-Rifamycin Derivatives Targeting RNA Polymerase," filed on Jun. 9, 2004, having Ma, et al., listed as the inventors, the entire content of which is hereby incorporated by reference.

BACKGROUND OF THE INVENTION

This invention relates to rifamycin derivatives having antimicrobial activity, compositions containing the compounds, and methods for treatment and prevention of microbial infections. The compounds of the current invention exhibit potent antimicrobial activity and improved activity against rifamycin-resistant bacteria. In particular, the compounds of the current invention relate to a series of novel spiro rifamycin derivatives which demonstrated potent antibiotic activity.

Rifamycins are potent antibiotics targeting bacterial RNA polymerase. The therapeutic applications of the naturally-occurring rifamycins are limited due to their poor oral bioavailability, weak activity against Gram-negative pathogens and low distribution into the infected tissues. Significant efforts have been made toward identifying semi-synthetic rifamycin derivatives to address these deficiencies. As a result, many semi-synthetic rifamycin derivatives with improved spectra and pharmacological profiles have been identified. Among the semi-synthetic compounds, rifampin, rifabutin and rifapetine have been developed into therapeutic agents and are currently used for the treatment of tuberculosis and other microbial infections (Farr, Rifamycins).

At present, one of the major problems associated with the rifamycin class of antimicrobial agents is the rapid development of microbial resistance. Mutations in RNA polymerase are mainly responsible for the high frequency of microbial resistance to rifamycins. Consequently, rifamycins are currently used only in combination therapies to minimize the development of resistance to this class of drug.

Reference is made to U.S. Pat. No. 4,219,478 that disclosed a series of spiro compounds which contain a 5-membered imidazoline ring, fused to the 3,4-position of rifamycin. The compounds of the current invention are structurally distinct, containing a 6-membered heterocycle fused to the 3,4-position of rifamycin. The compounds of the current invention have demonstrated improved activity against rifamycin resistant strains.

References are also made to U.S. Pat. No. 4,690,919, U.S. Pat. No. 4,859,661, U.S. Pat. No. 4,965,261, and U.S. Pat. No. 4,983,602 that disclosed a series of 6-membered heterocyclic rifamycin derivatives. Compounds of the current invention are structurally distinct by having a spiro system in the structure.

SUMMARY

A preferred embodiment of the current invention is a series of compounds having general Formula I:

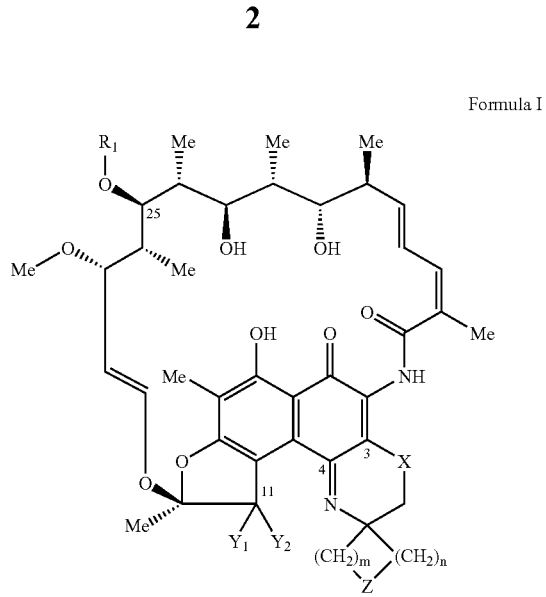

Formula I

The rifamycin derivatives illustrated in general Formula I above have been labeled at the C-3, C-4, C-11 and C-25 positions for illustration purposes. Structures having Formula I of the current invention contain many asymmetric and geometric centers. In some cases, one or more of the asymmetric or geometric centers can be converted to their opposite configurations. These stereoisomers of rifamycin are expected to have antimicrobial activity and therefore are within the scope of the invention.

A preferred $R_1$ in Formula I represents hydrogen, $(C_1-C_6)$ alkyl, substituted $(C_1-C_6)$alkyl, —C(O)CH$_2$R$_{10}$, or —C(O) NR$_{11}$R$_{12}$. In the natural form, rifamycins have an acetyl group at this C-25 position. Chemical or enzymatic hydrolysis of the acetyl group provides the de-acetylated compounds wherein $R_1$ is a hydrogen. These de-acetylated compounds can be further transformed to compounds having the $R_1$ substitutions listed above. $R_{10}$ can be a variety of groups, such as hydrogen, halogen, hydroxyl, thio, amino, $(C_1-C_6)$alkyl, $(C_1-C_6)$alkoxy, $(C_1-C_6)$alkylthio, $(C_1-C_6)$ acyloxy, $(C_1-C_6)$alkylamino, di$(C_1-C_6)$alkylamino, aryl, heteroaryl, or heterocyclic group, all of which are optionally substituted. Alternatively, $R_{10}$ represents -L$_{25}$-Q$_{25}$. L$_{25}$ represents a linker group consisting of any combination of 1–3 groups selected from those illustrated in FIG. 1. Q$_{25}$ represents an antibacterial pharmacophore associated with quinolones, macrolides, oxazolidinones, β-lactams, or other antibiotics. $R_{11}$ and $R_{12}$ independently can be a variety of groups such as hydrogen, $(C_1-C_6)$alkyl, substituted $(C_1-C_6)$ alkyl, or -L$_{25}$-Q$_{25}$. Alternatively, $R_{11}$ and $R_{12}$, together with the nitrogen atom to which they are attached, can form a 3- to 8-membered heterocyclic ring, optionally containing up to two additional heteroatoms, wherein the carbon or nitrogen atoms are optionally substituted by one $(C_1-C_6)$alkyl or -L$_{25}$-Q$_{25}$.

In the natural form, the C-11 position of rifamycins is a ketone group, which can be reduced to hydroxyl group in diastereomeric mixture by chemical reagents. In this case, one of $Y_1$ and $Y_2$ in Formula I represents —OH and the other represents hydrogen. Alternatively, the ketone group of the C-11 position can be transformed to oxime =N—OH or =N—OR$_{21}$ by the treatment with hydroxylamine or alkoxylamine. Thus, $Y_1$ and $Y_2$ together with the carbon at position 11 to which they are attached can form a C=O or C=N—O—R$_{21}$ wherein R$_{21}$ is hydrogen, $(C_1-C_6)$alkyl or -L$_{11}$-Q$_{11}$.

$L_{11}$ represents a linker group consisting of any combination of 1–3 groups selected from FIG. 1. $Q_{11}$ represents an antibacterial pharmacophore associated with quinolones, macrolides, oxazolidinones, β-lactams, or other antibiotics.

X in Formula I represents $-CR_{31}R_{32}-$, $-NR_{33}-$, $-S-$ or $-O-$, to form a piperidine ring, piperazine ring, thiazine ring, or oxazine ring fused to the 3,4-position of the rifamycin core. $R_{31}$, $R_{32}$ and $R_{33}$ independently can be similar or different and can be hydrogen or $(C_1-C_6)$alkyl. The variables m and n represent an integer between 1 and 3.

Z in Formula I represents $-CR_{42}R_{43}-$ to form a carbocycle, or $-NR_{41}-$, $-O-$, or $-S(O)_p-$ to form a heterocycle, wherein p is an integer between 0 and 2. $R_{41}$ can be hydrogen, $(C_1-C_6)$alkyl, $(C_1-C_6)$alkyl sulfonyl, aryl sulfonyl, $(C_1-C_6)$alkoxycarbonyl, aryloxycarbonyl, $(C_1-C_6)$alkyl amino carbonyl, or aryl amino carbonyl, which are all optionally substituted, or -L-Q. L may be absent or may be a linker group comprising any combination of from 1 to 5 groups selected from $(C_1-C_6)$alkylene, $(C_3-C_8)$cycloalkylene, arylene, heteroarylene, bivalent heterocyclic group containing 1 to 3 heteroatoms, $-C(=O)-$, $-C(=N-O-R_{13})$, $-C=N-$, $-O-$, $-S(O)_n-$, wherein n is an integer between 0 and 2, and $-N(R_{14})-$. The carbon or nitrogen atoms of the linker group are optionally substituted by 1 to 3 substituents selected from $(C_1-C_6)$alkyl, amino, $(C_1-C_6)$alkylamino, di$(C_1-C_6)$alkylamino, hydroxyl, $(C_1-C_6)$alkoxy, or heterocyclic group. $R_{13}$ and $R_{14}$ are independently a group selected from hydrogen, $(C_1-C_6)$alkyl, aryl, heteroaryl, and heterocyclic group, all of which may be optionally substituted. Q represents an antibacterial pharmacophore associated with quinolones, macrolides, oxazolidinones, β-lactams, or other antibiotics. When Z is $-CR_{42}R_{43}-$, $R_{42}$ and $R_{43}$ independently may be the same or different and represent hydrogen, hydroxyl, amino, carboxyl, halo, cyano, $(C_1-C_6)$alkyl, $(C_3-C_6)$cycloalkyl, $(C_1-C_6)$heteroaryl, or heterocyclic groups, which are all optionally substituted.

An additional preferred embodiment of the current invention is a series of compounds having general Formula II:

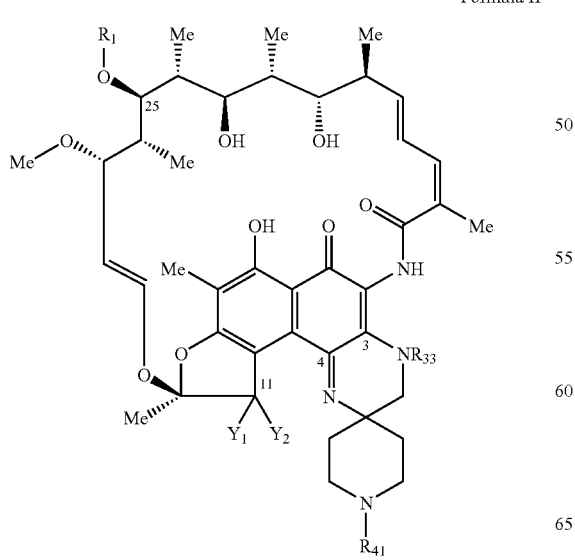

Formula II

An additional preferred embodiment of the current invention is a series of compounds having general Formula III:

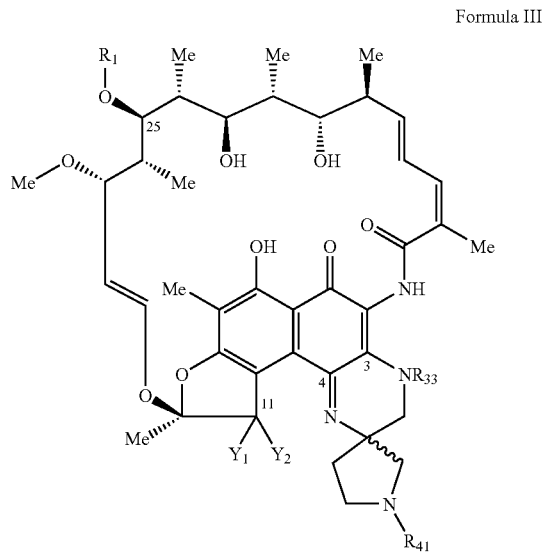

Formula III

An additional preferred embodiment of the current invention is a series of compounds having general Formula IV:

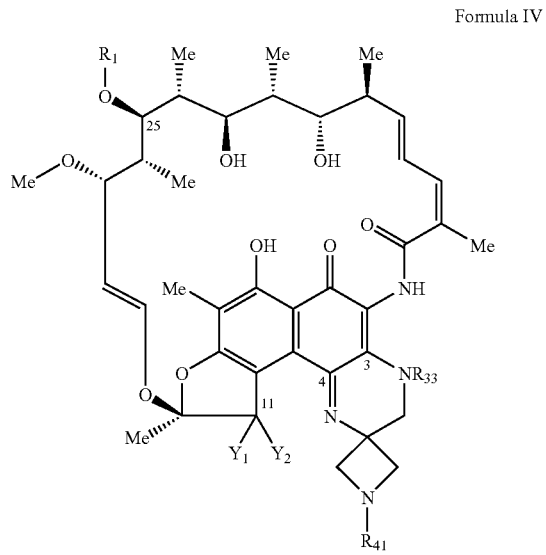

Formula IV

In general Formula II, Formula III, and Formula IV above, all substituents are defined as they were defined above with respect to general Formula I.

Another aspect of the current invention comprises a method of treating a microbial infection in a subject; wherein the subject is any species of the animal kingdom. The microbial infection can be caused by a bacterium or microorganism. The term "subject" refers more specifically to human and animals, wherein the animals can be used for: pets (e.g. cats, dogs, etc.); work (e.g. horses, cows, etc.); food (chicken, fish, lambs, pigs, etc); and all others known in the art. The method comprises administering an effective amount of one or more compounds of the present invention to the subject suffering from a microbial infection.

DETAILED DESCRIPTION

Figure 1:
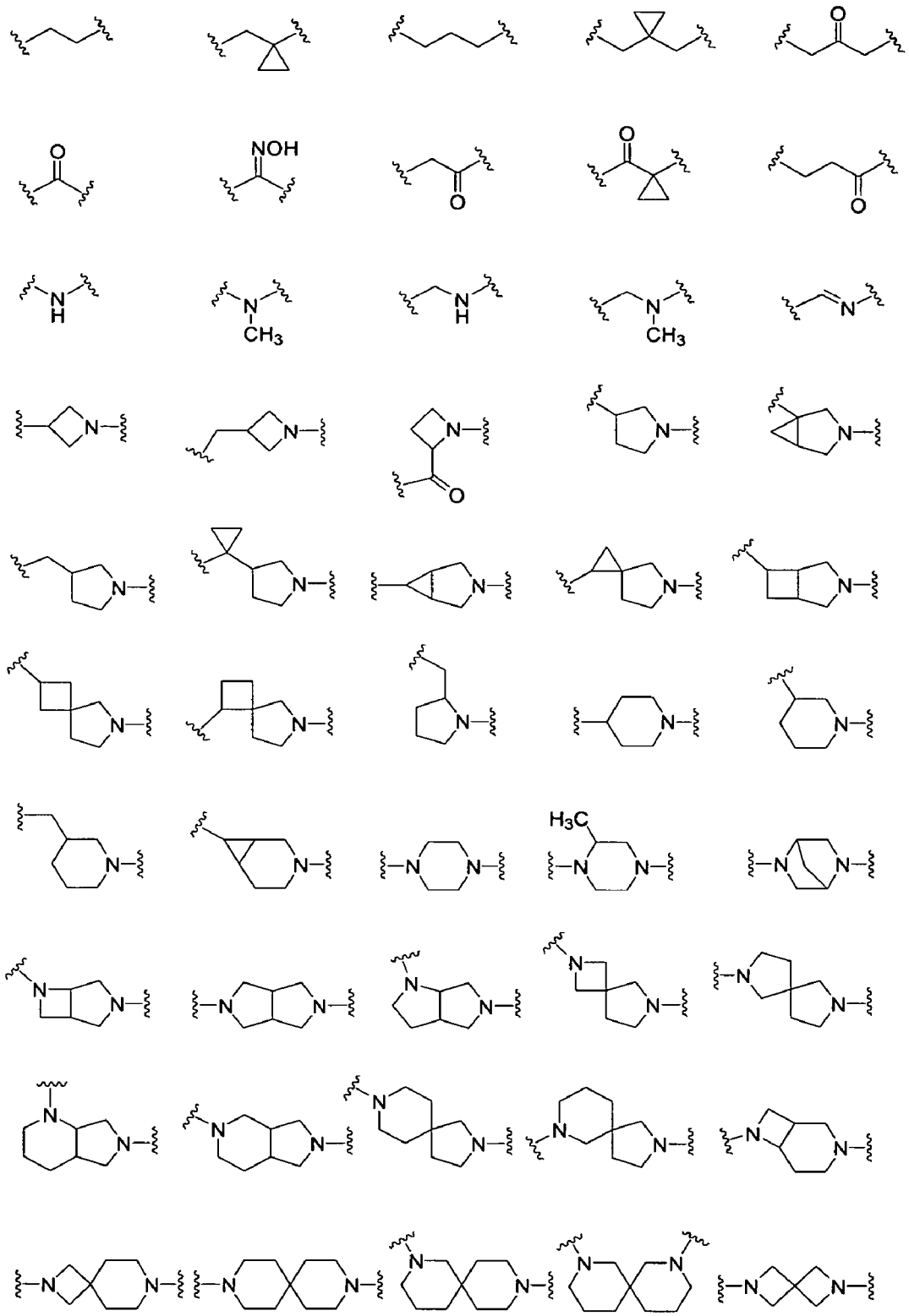
FIG. 1 shows a group of linkers, which are preferred structures for L, $L_{11}$, and $L_{25}$.

Terms:

The term "alkenyl," as used herein, refers to a monovalent straight or branched chain group containing at least one carbon-carbon double bond. The alkenyl groups of this invention can be optionally substituted.

The term "alkenylene," as used herein, refers to a bivalent straight or branched chain group containing at least one carbon-carbon double bond. The alkenylene groups of this invention can be optionally substituted.

The term "alkyl," as used herein, refers to a monovalent, saturated, straight or branched chain hydrocarbon group. Examples of alkyl group include methyl, ethyl, propyl, iso-propyl, n-butyl, iso-butyl, tert-butyl, neo-pentyl, and n-hexyl. The alkyl groups of this invention can be optionally substituted.

The term "alkyl sulfonyl," as used herein, refers to an alkyl group, as previously defined, attached to the parent molecular group through a sulfonyl group (—S(O)$_2$—). Examples of alkyl sufonyl include methyl sulfonyl, ethyl sulfonyl, propyl sulfonyl, iso-propyl sulfonyl, n-butyl sulfonyl, tert-butyl sulfonyl, neo-pentyl sulfonyl and n-hexyl sulfonyl. The alkyl groups of this invention can be optionally substituted.

The term "alkylene," as used herein, refers to bivalent saturated, straight or branched chain hydrocarbon structures. Examples of alkylene groups include methylene, ethylene, propylene, iso-propylene, n-butylene, iso-butylene, and n-hexylene. The alkylene groups of this invention can be optionally substituted.

The term "alkylamino," as used herein, refers to an amino group (—NH$_2$), wherein one hydrogen atom is replaced by an alkyl group. Examples of alkylamino include methylamino, ethylamino, propylamino, and isopropylamino.

The term "alkylamino carbonyl," refers to an alkylamino group, as previously defined, attached to the parent molecular group through a carbonyl group (—C(═O)—). Examples of alkylamino carbonyl include methylamino carbonyl, ethylamino carbonyl, propylamio carbonyl, iso-propylamino carbonyl, n-butylamino carbonyl, tert-butylamino carbonyl, neo-pentylamino carbonyl and n-hexylamino carbonyl. The alkylamino groups of this invention can be optionally substituted.

The term "alkylthio," as used herein, refers to an alkyl group, as defined herein, attached to the parent molecular group through a sulfur atom. Examples of alkylthio include methylthio, ethylthio, propylthio, and isopropylthio.

The term "alkoxy," as used herein, refers to an alkyl group, as previously defined, attached to the parent molecular group through an oxygen atom. Examples of alkoxy include methoxy, ethoxy, propoxy, iso-propoxy, n-butoxy, tert-butoxy, neo-pentoxy and n-hexoxy. The alkoxy groups of this invention can be optionally substituted.

The term "alkoxy carbonyl," refers to an alkoxy group, as previously defined, attached to the parent molecular group through a carbonyl group (—C(═O)—). Examples of alkoxy carbonyl include methoxy carbonyl, ethoxy carbonyl, propoxy carbonyl, iso-propoxy carbonyl, n-butoxy carbonyl, tert-butoxy carbonyl, neo-pentoxy carbonyl and n-hexoxy carbonyl. The alkoxy groups of this invention can be optionally substituted.

The term "alkynyl," as used herein, refers to a monovalent straight or branched chain group of two to six carbon atoms containing at least one carbon-carbon triple bond. Examples of alkynyl include ethynyl, propynyl, and butynyl. The alkynyl groups of this invention can be optionally substituted.

The term "alkynylene," as used herein, refers to a bivalent straight or branched chain group of two to six carbon atoms containing at least one carbon-carbon triple bond. Examples of alkynylene include ethynylene, propynylene, and butynylene. The alkynylene groups of this invention can be optionally substituted The term "aprotic solvent," as used herein, refers to a solvent that is relatively inert to protonic activity, i.e., not acting as a proton donor. Examples include hexane, toluene, dichloromethane, ethylene dichloride, chloroform, tetrahydrofuran, N-methylpyrrolidinone, diethyl ether.

The term "aryl" as used herein refers to a monovalent carbocyclic aromatic group including phenyl, naphthyl, and anthracenyl.

The term "aryl sulfonyl," as used herein, refers to an aryl group, as previously defined, attached to the parent molecular group through a sulfonyl group (—S(O)$_2$—). Examples of aryl sulfonyl include phenyl sulfonyl, naphthyl sulfonyl, anthracenyl sulfonyl.

The term "arylamino carbonyl," refers to an arylamino group attached to the parent molecular group through a carbonyl group (—C(═O)—). Examples of arylamino carbonyl include phenylamino carbonyl, naphtylamino carbonyl and anthracenylamino carbonyl.

The term "arylene" as used herein refers to bivalent carbocyclic aromatic groups which can be optionally substituted.

The term "aryloxy carbonyl," refers to an aryloxy group attached to the parent molecular group through a carbonyl group (—C(═O)—), wherein the term "aryloxy," refers an aryl group attached to the parent molecular group through oxygen (—O—). Examples of aryloxy carbonyl include phenoxy carbonyl, naphtyloxy carbonyl, anthracenyloxy carbonyl.

The term "benzyl," as used herein, refers to —CH$_2$C$_6$H$_5$.

The term "benzyloxy," as used herein, refers to a benzyl group, as defined herein, attached to the parent molecular group through an oxygen atom.

The term "carboxaldehyde," as used herein, refers to —CHO.

The term "cycloalkyl," as used herein, refers to a monovalent saturated carbocyclic group having three to eight carbons such as cyclopropyl, cyclobutyl, cyclopentyl, cyclohexyl, cycloheptyl and cyclooctyl.

The term "cycloalkylene," as used herein, refers to bivalent saturated carbocyclic groups having three to eight carbons. The cycloalkylene groups can be optionally substituted.

The term "halogen," as used herein, refers to fluorine, chlorine, bromine and iodine atoms and the term "halo" refers to —F, —Cl, —Br, and —I as substituent.

The term "heteroaryl," as used herein, refers to a cyclic aromatic group having five or six ring atoms wherein at least one ring atom is selected from the group consisting of oxygen, sulfur, and nitrogen, and the remaining ring atoms are carbon. Heteroaryl groups of this invention include those derived from furan, imidazole, isothiazole, isoxazole, oxazole, pyrazine, pyrazole, pyridazine, pyridine, pyrimidine, pyrrole, quinoline, thiazole, 1,3,4-thiadiazole, triazole, and tetrazole.

The term "heteroarylene," as used herein, refers to a bivalent cyclic aromatic group having five or six ring atoms wherein at least one ring atom is selected from the group consisting of oxygen, sulfur, and nitrogen, and the remaining ring atoms are carbon. The heteroarylene group can be optionally substituted.

The term "heteroatom," as used herein, refers to oxygen, nitrogen or sulfur atom.

The term "heterocycloalkyl" as used herein, refers to a non-aromatic five-, six- or seven-membered ring or a bi- or tri-cyclic group having one or more heteroatoms independently selected from oxygen, sulfur and nitrogen wherein each 5-membered ring has zero to one double bonds and each six-membered ring has zero to 2 double bonds. The nitrogen and sulfur heteroatoms can optionally be oxidized, the nitrogen heteroatom can optionally be quaternized, and any of the above heterocyclic rings can be fused to an aryl or heteroaryl ring. Representative heterocycles include, but are not limited to: pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofurranyl. The heterocycloalkyl groups of this invention can be optionally substituted with one, two, or three substituents independently selected from —F, —Cl, —OH, —NO$_2$, —CN, —C(O)-alkyl, —C(O)-aryl, —C(O)-heteroaryl, —CO$_2$-alkyl, —CO$_2$-aryl, —CO$_2$-heteroaryl, —C(O)NH$_2$, —C(O)NH-alkyl, —C(O)NH-aryl, —C(O)NH-heteroaryl, —OC(O)-alkyl, —OC(O)-aryl, —OC(O)-heteroaryl, —OC(O)NH$_2$, —OC(O)NH-alkyl, —OC(O)NH-aryl, —OCONH-heteroaryl, —NHC(O)-alkyl, —NHC(O)-aryl, —NHC(O)-heteroaryl, —NHCO$_2$-alkyl, —NHCO$_2$-aryl, —NHCO$_2$-heteroaryl, —NHC(O)NH$_2$, —NHC(O)NH-alkyl, —NHC(O) NH-aryl, —NHC(O)NH-heteroaryl, —SO$_2$-alkyl, —SO$_2$-aryl, —SO$_2$-heteroaryl, —SO$_2$NH$_2$, —SO$_2$NH-alkyl, —SO$_2$NH-aryl, —SO$_2$NH-heteroaryl, -alkyl, -cycloalkyl, -heterocycloalkyl, —CF$_3$, —CH$_2$OH, —CH$_2$NH$_2$, -aryl, -heteroaryl, -benzyl, -benzyloxy, -aryloxy, -heteroaryloxy, -alkoxy, -methoxymethoxy, -methoxyethoxy, -amino, -benzylamino, -arylamino, -heteroarylamino, -alkylamino, -thio, -arylthio, -heteroarylthio, -benzylthio, -alkylthio, or -methylthiomethyl.

The term "heterocycloalkylene" as used herein, refers to a bivalent non-aromatic five-, six- or seven-membered ring having one or more heteroatoms independently selected from oxygen, sulfur and nitrogen wherein each 5-membered ring has zero to one double bonds and each six-membered ring has zero to 2 double bonds. The heterocycloalkylene groups of this invention can be optionally substituted.

The term "hydroxyl," as used herein, refers to —OH.

The term "pharmaceutically acceptable carrier," as used herein, means a nontoxic, inert solid, semi-solid or liquid filler, diluent, encapsulating material or formulation auxiliary of any type. Some examples of materials which can serve as pharmaceutically acceptable carriers are carbohydrates such as lactose, glucose and sucrose; starches such as corn starch and potato starch; cellulose and its derivatives such as sodium carboxymethyl cellulose, ethyl cellulose and cellulose acetate; glycols; such a propylene glycol; esters such as ethyl oleate and ethyl laureate; agar; buffering agents such as magnesium hydroxide and aluminum hydroxide; isotonic saline; ethyl alcohol, and phosphate buffer solutions, as well as other nontoxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The term "pharmaceutically acceptable prodrugs," as used herein refers to the prodrugs of the compounds of the current invention which are suitable for use in humans and animals with acceptable toxicity, irritation, allergic response, and the like, commensurate with a reasonable benefit to risk ratio, and effective for their intended use. The term "prodrug," as used herein, represents compounds which can be transformed in vivo to parent compounds defined above.

The term "pharmaceutically acceptable salt," as used herein refers to those salts which are suitable for use in humans and animals with acceptable toxicity, irritation, and allergic response, etc., and are commensurate with a reasonable benefit to risk ratio. Pharmaceutically acceptable salts are well known in the art. The salts can be prepared in situ during the final step of isolation and purification of the compounds of the invention or separately prepared by reacting the compounds of the invention with an acid or base. Examples of pharmaceutically acceptable salts are salts of an amino group formed with inorganic acids such as hydrochloric acid, hydrobromic acid, phosphoric acid, and sulfuric acid or with organic acids such as acetic acid, oxalic acid, maleic acid, tartaric acid, citric acid, succinic acid, or malonic acid. Examples of pharmaceutically acceptable salts are salts of an acid group formed with inorganic bases such as sodium hydroxide, sodium carbonate, sodium phosphate, etc. Other metal salts include lithium, potassium, calcium, and magnesium. Additional pharmaceutically acceptable salts include ammonium cations formed with counterions such as halide, hydroxide, carboxylate, sulfate, phosphate, nitrate, lower alkyl sulfonate, and aryl sulfonate.

The term "protecting group", as used herein, refers to an easily removable group to which are known in the art to protect a functional group, such as hydroxyl and amino, against undesirable reaction during synthetic procedures and to be selectively removable. The use of protecting groups is well-known in the art for protecting groups against undesirable reactions during a synthetic procedure and many such protecting groups are known (T. H. Greene and P. G. M. Wuts, Protective Groups in Organic Synthesis, 2nd edition, John Wiley & Sons, New York, 1991).

The term "substituted aryl," as used herein, refers to an aryl group, as defined herein, substituted by independent replacement of one, two or three of the hydrogen atoms with —F, —Cl, —OH, —NO$_2$, —CN, —C(O)-alkyl, —C(O)-aryl, —C(O)-heteroaryl, —CO$_2$-alkyl, —CO$_2$-aryl, —CO$_2$-heteroaryl, —C(O)NH$_2$, —C(O)NH-alkyl, —C(O)NH-aryl, —C(O)NH-heteroaryl, —OC(O)-alkyl, —OC(O)-aryl, —OC(O)-heteroaryl, —OC(O)NH$_2$, —OC(O)NH-alkyl, —OC(O)NH-aryl, —OCONH-heteroaryl, —NHC(O)-alkyl, —NHC(O)-aryl, —NHC(O)-heteroaryl, —NHCO$_2$-alkyl, —NHCO$_2$-aryl, —NHCO$_2$-heteroaryl, —NHC(O) NH$_2$, —NHC(O)NH-alkyl, —NHC(O)NH-aryl, —NHC(O) NH-heteroaryl, —SO$_2$-alkyl, —SO$_2$-aryl, —SO$_2$-heteroaryl, —SO$_2$NH$_2$, —SO$_2$NH-alkyl, —SO$_2$NH-aryl, —SO$_2$NH-heteroaryl, -alkyl, -cycloalkyl, -heterocycloalkyl, —CF$_3$, —CH$_2$OH, —CH$_2$NH$_2$, -aryl, -heteroaryl, -benzyl, -benzyloxy, -aryloxy, -heteroaryloxy, -alkoxy, -methoxymethoxy, -methoxyethoxy, -amino, -benzylamino, -arylamino, -heteroarylamino, -alkylamino, -thio, -arylthio, -heteroarylthio, -benzylthio, -alkylthio, or -methylthiomethyl.

The term "substituted heteroaryl" as used herein refers to a heteroaryl group as defined herein substituted by independent replacement of one, two or three of the hydrogen atoms with —F, —Cl, —OH, —NO₂, —CN, —C(O)-alkyl, —C(O)-aryl, —C(O)-heteroaryl, —CO₂-alkyl, —CO₂-aryl, —CO₂-heteroaryl, —C(O)NH₂, —C(O)NH-alkyl, —C(O)NH-aryl, —C(O)NH-heteroaryl, —OC(O)-alkyl, —OC(O)-aryl, —OC(O)-heteroaryl, —OC(O)NH₂, —OC(O)NH-alkyl, —OC(O)NH-aryl, —OCONH-heteroaryl, —NHC(O)-alkyl, —NHC(O)-aryl, —NHC(O)-heteroaryl, —NHCO₂-alkyl, —NHCO₂-aryl, —NHCO₂-heteroaryl, —NHC(O)NH₂, —NHC(O)NH-alkyl, —NHC(O)NH-aryl, —NHC(O)NH-heteroaryl, —SO₂-alkyl, —SO₂-aryl, —SO₂-heteroaryl, —SO₂NH₂, —SO₂NH-alkyl, —SO₂NH-aryl, —SO₂NH-heteroaryl, -alkyl, -cycloalkyl, -heterocycloalkyl, —CF₃, —CH₂OH, —CH₂NH₂, -aryl, -heteroaryl, -benzyl, -benzyloxy, -aryloxy, -heteroaryloxy, -alkoxy, -methoxymethoxy, -methoxyethoxy, -amino, -benzylamino, -arylamino, -heteroarylamino, -alkylamino, -thio, -arylthio, -heteroarylthio, -benzylthio, -alkylthio, or -methylthiomethyl.

The term "substituted heterocycloalkyl," as used herein, refers to a heterocycloalkyl group, as defined above, substituted by independent replacement of one, two or three of the hydrogen atoms with —F, —Cl, —OH, —NO₂, —CN, —C(O)-alkyl, —C(O)-aryl, —C(O)-heteroaryl, —CO₂-alkyl, —CO₂-aryl, —CO₂-heteroaryl, —C(O)NH₂, —C(O)NH-alkyl, —C(O)NH-aryl, —C(O)NH-heteroaryl, —OC(O)-alkyl, —OC(O)-aryl, —OC(O)-heteroaryl, —OC(O)NH₂, —OC(O)NH-alkyl, —OC(O)NH-aryl, —OCONH-heteroaryl, —NHC(O)-alkyl, —NHC(O)-aryl, —NHC(O)-heteroaryl, —NHCO₂-alkyl, —NHCO₂-aryl, —NHCO₂-heteroaryl, —NHC(O)NH₂, —NHC(O)NH-alkyl, —NHC(O)NH-aryl, —NHC(O)NH-heteroaryl, —SO₂-alkyl, —SO₂-aryl, —SO₂-heteroaryl, —SO₂NH₂, —SO₂NH-alkyl, —SO₂NH-aryl, —SO₂NH-heteroaryl, -alkyl, -cycloalkyl, -heterocycloalkyl, —CF₃, —CH₂OH, —CH₂NH₂, -aryl, -heteroaryl, -benzyl, -benzyloxy, -aryloxy, -heteroaryloxy, -alkoxy, -methoxymethoxy, -methoxyethoxy, -amino, -benzylamino, -arylamino, -heteroarylamino, -alkylamino, -thio, -arylthio, -heteroarylthio, -benzylthio, -alkylthio, or -methylthiomethyl.

The term "substituent," as used herein, refers to —F, —Cl, —OH, —NO₂, —CN, —C(O)-alkyl, —C(O)-aryl, —C(O)-heteroaryl, —CO₂-alkyl, —CO₂-aryl, —CO₂-heteroaryl, —C(O)NH₂, —C(O)NH-alkyl, —C(O)NH-aryl, —C(O)NH-heteroaryl, —OC(O)-alkyl, —OC(O)-aryl, —OC(O)-heteroaryl, —OC(O)NH₂, —OC(O)NH-alkyl, —OC(O)NH-aryl, —OCONH-heteroaryl, —NHC(O)-alkyl, —NHC(O)-aryl, —NHC(O)-heteroaryl, —NHCO₂-alkyl, —NHCO₂-aryl, —NHCO₂-heteroaryl, —NHC(O)NH₂, —NHC(O)NH-alkyl, —NHC(O)NH-aryl, —NHC(O)NH-heteroaryl, —SO₂-alkyl, —SO₂-aryl, —SO₂-heteroaryl, —SO₂NH₂, —SO₂NH-alkyl, —SO₂NH-aryl, —SO₂NH-heteroaryl, -alkyl, -cycloalkyl, -heterocycloalkyl, —CF₃, —CH₂OH, —CH₂NH₂, -aryl, -heteroaryl, -benzyl, -benzyloxy, -aryloxy, -heteroaryloxy, -alkoxy, -methoxymethoxy, -methoxyethoxy, -amino, -benzylamino, -arylamino, -heteroarylamino, -alkylamino, -thio, -arylthio, -heteroarylthio, -benzylthio, -alkylthio, or -methylthiomethyl.

Abbreviations:

Abbreviations as used herein have the meanings known by one skilled in the art. Specifically, Ac represents acetyl group, AOC (alloc) represents allyloxycarbonyl group, BOC represents t-butoxycarbonyl group, Bn represents benzyl group, Bu represents butyl group, Bz represents benzoyl group, Cbz represents benzyloxycarbonyl group, CDI represents carbonyldiimidazole, DCM represents dichloromethane, DMAP represents 4-N,N-dimethylaminopyridine, DME represents 1,2-dimethoxyethane, DMF represents N,N-dimethylformamide, DMSO represents dimethyl sulfoxide, Et represents ethyl group, EtOAc represents ethyl acetate, Me represents methyl group, MEM represents 2-methoxyethoxymethyl group, MOM represents methoxylmethyl group, NMP represents N-methylpyrrolidinone, Ph represents phenyl group, Pr represents propyl group, TEA represents triethylamine, TFA represents trifluoroacetic acid, TFAA represents trifluoroacetic anhydride, THF represents tetrahydrofuran, TMS represents trimethylsilyl group, and Ts represents p-toluenesulfonyl group.

A preferred embodiment of the current invention is a series of compounds having general Formula I:

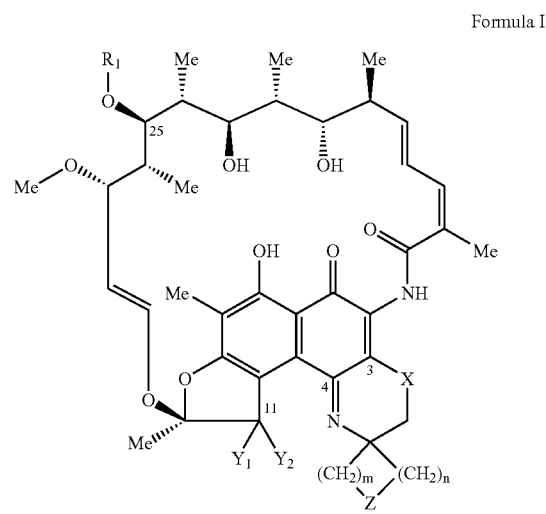

Formula I wherein, $R_1$ is hydrogen, $(C_1-C_6)$alkyl, substituted $(C_1-C_6)$alkyl, —C(O)CH₂R₁₀, or —C(O)NR₁₁R₁₂, wherein $R_{10}$ is hydrogen, halogen, hydroxyl, thio, amino, $(C_1-C_6)$alkyl, $(C_1-C_6)$alkoxy, $(C_1-C_6)$alkylthio, $(C_1-C_6)$acyloxy, $(C_1-C_6)$alkylamino, di$(C_1-C_6)$alkylamino, aryl, heteroaryl, or -L₂₅-Q₂₅, wherein $L_{25}$ is a linker group consisting of any combination of from 1 to 3 groups selected from those shown in FIG. 1 and $Q_{25}$ is an antibacterial pharmacophore associated with quinolones, macrolides, oxazolidinones, β-lactams, or other antibiotics;

wherein $R_{11}$, and $R_{12}$ independently are hydrogen, $(C_1-C_6)$alkyl, substituted $(C_1-C_6)$alkyl, or -L₂₅-Q₂₅, or $R_{11}$ and $R_{12}$, together with the nitrogen atom to which they are attached, form a 3- to 8-membered heterocyclic ring, optionally containing up to two heteroatoms, wherein one or more of the carbon or nitrogen atoms of the heterocyclic ring is optionally substituted by $(C_1-C_6)$alkyl or -L₂₅-Q₂₅;

one of $Y_1$ and $Y_2$ represents —OH and the other represents hydrogen, or $Y_1$ and $Y_2$ together with the carbon to which they are attached form C=O or C=N—O—R₂₁, wherein $R_{21}$ is hydrogen, $(C_1-C_6)$alkyl or -L₁₁-Q₁₁, wherein $L_{11}$ represents a linker group consisting of any combination of one to three groups selected from FIG. 1 and $Q_{11}$ is an antibacterial pharmacophore associated with quinolones, macrolides, oxazolidinones, β-lactams, or other antibiotics;

X is —$CR_{31}R_{32}$—, —$NR_{33}$—, —S— or —O—,
wherein $R_{31}$, $R_{32}$ and $R_{33}$ independently represent hydrogen or $(C_1-C_6)$alkyl, and
m and n independently are the same or different and are an integer between 1 and 3; and Z is —$NR_{41}$—, —$CR_{42}R_{43}$—, —O—, or —$S(O)_p$—,
wherein p is an integer between 0 and 2,
$R_4$, is hydrogen, $(C_1-C_6)$alkyl, $(C_1-C_6)$alkyl sulfonyl, aryl sulfonyl, $(C_1-C_6)$alkoxycarbonyl, aryloxycarbonyl, $(C_1-C_6)$alkyl amino carbonyl, aryl amino carbonyl, which are all optionally substituted, or -L-Q,
wherein L represents a linker group comprising any combination of from 1 to 5 groups selected from $(C_1-C_6)$alkylene, $(C_3-C_8)$cycloalkylene, arylene, heteroarylene, bivalent heterocyclic group containing 1 to 3 heteroatoms, —C(=O)—, —C(=N—O—$R_{13}$), —C=N—, —O—, —$S(O)_n$—, and —$N(R_{14})$—,
wherein n is an integer between 0 and 2, the carbon or nitrogen atoms of the linker group are optionally substituted by 1 to 3 substituents selected from $(C_1-C_6)$alkyl, amino, $(C_1-C_6)$alkylamino, di$(C_1-C_6)$alkylamino, hydroxyl, $(C_1-C_6)$alkoxy, and heterocyclic group, $R_{13}$ and $R_{14}$ are independently the same or different and are hydrogen, $(C_1-C_6)$alkyl, aryl, heteroaryl, or heterocyclic group, and Q is an antibacterial pharmacophore associated with quinolones, macrolides, oxazolidinones, β-lactams, or other antibiotics, and
$R_{42}$ and $R_{43}$ independently are the same or different and are hydrogen, hydroxyl, amino, carboxyl, halo, cyano, $(C_1-C_6)$alkyl, $(C_3-C_6)$cycloalkyl, $(C_1-C_6)$heteroaryl, or heterocyclic group.

An additional preferred embodiment of the current invention is a series of compounds having general Formula II:

Formula II

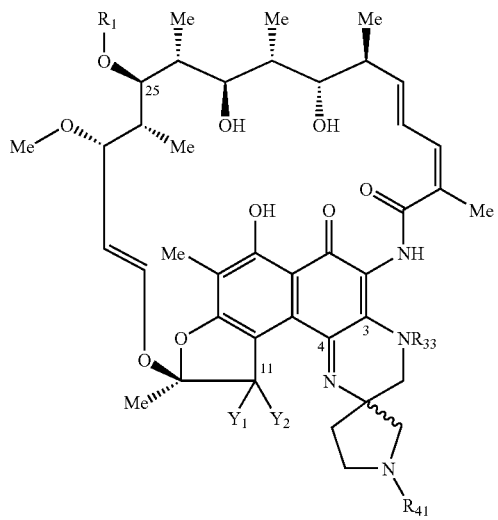

Formula III

An additional preferred embodiment of the current invention is a series of compounds having general Formula IV:

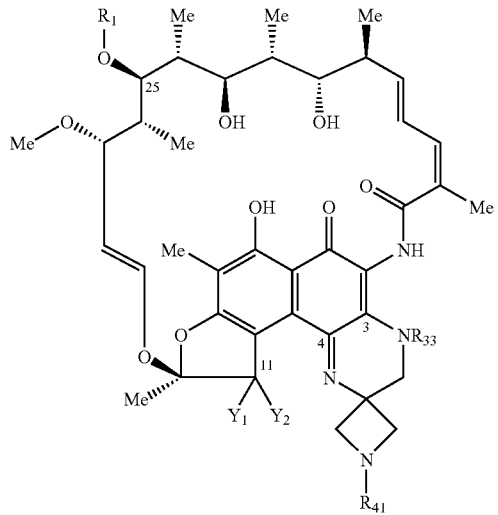

Formula IV

In general Formula II, Formula III, and Formula IV above, all substituents are defined as they were defined above with respect to general Formula I.

Compositions:

The compounds of the current invention are rifamycin derivatives of Formula I, which have been labeled at the $C_3$, $C_4$, $C_{11}$, and $C_{25}$ positions for illustration purposes. In one aspect, compounds of the current invention contain many asymmetric and geometric centers. In some cases, one or more of the asymmetric or geometric centers can be converted to their opposite configurations. These stereoisomers of rifamycin are within the scope of the present invention.

EXAMPLE 1

These examples are intended for illustration purposes only and are not intended to limit the scope of this invention.

A preferred embodiment of the current invention is a series of compounds having general Formula I:

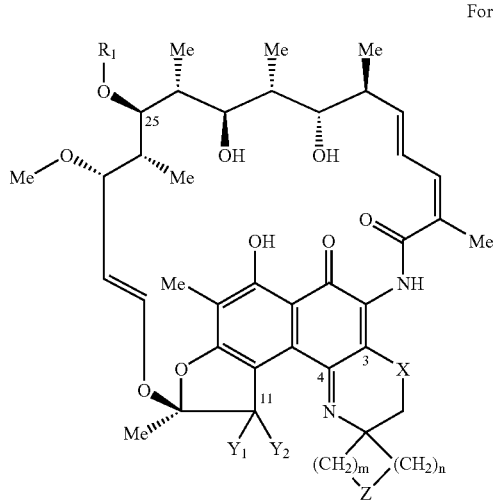

Formula I $R_1$ in Formula I is hydrogen, $(C_1-C_6)$alkyl, substituted $(C_1-C_6)$alkyl, —C(O)CH$_2$R$_{10}$, or —C(O)NR$_{11}$R$_{12}$. $R_{10}$ is hydrogen, halogen, hydroxyl, thio, amino, $(C_1-C_6)$alkyl, $(C_1-C_6)$alkoxy, $(C_1-C_6)$alkylthio, $(C_1-C_6)$acyloxy, $(C_1-C_6)$alkylamino, di$(C_1-C_6)$alkylamino, aryl, heteroaryl, heterocyclic group, or -L$_{25}$-Q$_{25}$. L$_{25}$ is a linker group comprising any combination of 1–3 groups selected from those illustrated in FIG. 1. Q$_{25}$ is an antibacterial pharmacophore associated with quinolones, macrolides, oxazolidinones, β-lactams, or other antibiotics. $R_{11}$ and $R_{12}$ independently are similar or different and are hydrogen, $(C_1-C_6)$alkyl, substituted $(C_1-C_6)$alkyl, or -L$_{25}$-Q$_{25}$. Alternatively, R$_1$, and R$_{12}$, together with the nitrogen atom to which they are attached, can form a 3- to 8-membered heterocyclic ring, optionally containing up to two additional heteroatoms, wherein the carbon or nitrogen atoms are optionally substituted by one $(C_1-C_6)$alkyl or -L$_{25}$-Q$_{25}$.

One of $Y_1$ and $Y_2$ in Formula I is —OH and the other is hydrogen. Alternatively, $Y_1$ and $Y_2$ together with the carbon at position 11 to which they are attached form C=O or C=N—O—R$_{21}$, wherein R$_{21}$ is hydrogen, $(C_1-C_6)$alkyl or -L$_{11}$-Q$_{11}$. L$_{11}$ is a linker group comprising any combination of 1–3 groups selected from FIG. 1. Q$_{11}$ is an antibacterial pharmacophore associated with quinolones, macrolides, oxazolidinones, β-lactams, or other antibiotics.

X in Formula I is —CR$_{31}$R$_{32}$—, —NR$_{33}$—, —S— or —O—. R$_{31}$R$_{32}$ and R$_{33}$ independently are similar or different and are hydrogen or $(C_1-C_6)$alkyl. The variables m and n are an integer between 1 and 3.

Z in Formula I is —CR$_{42}$R$_{43}$—, —NR$_{41}$—, —O—, or —S(O)$_p$—, wherein p is an integer between 0 and 2. R$_{41}$ is hydrogen, $(C_1-C_6)$alkyl, $(C_1-C_6)$alkyl sulfonyl, aryl sulfonyl, $(C_1-C_6)$alkoxycarbonyl, aryloxycarbonyl, $(C_1-C_6)$alkyl amino carbonyl, aryl amino carbonyl, or -L-Q. L is absent or is a linker group comprising any combination of from 1 to 5 groups selected from $(C_1-C_6)$alkylene, $(C_3-C_8)$cycloalkylene, arylene, heteroarylene, bivalent heterocyclic group containing 1 to 3 heteroatoms, —C(=O), —C(=N—O—R$_{13}$)—, —C=N—, —O—, —S(O)$_n$—, wherein n is an integer between 0 and 2, and —N(R$_{14}$)—. The carbon or nitrogen atoms of the linker group are optionally substituted by 1 to 3 substituents selected from $(C_1-C_6)$alkyl, amino, $(C_1-C_6)$alkylamino, di$(C_1-C_6)$alkylamino, hydroxyl, $(C_1-C_6)$alkoxy, or heterocyclic group. R$_{13}$ and R$_{14}$ are independently the same or different and are a group selected from hydrogen, $(C_1-C_6)$alkyl, aryl, heteroaryl, and heterocyclic group. Q is an antibacterial pharmacophore associated with quinolones, macrolides, oxazolidinones, β-lactams, or other antibiotics. R$_{42}$ and R$_{43}$ independently are the same or different and are hydrogen, hydroxyl, amino, carboxyl, halo, cyano, $(C_1-C_6)$alkyl, $(C_3-C_6)$cycloalkyl, $(C_1-C_6)$heteroaryl, or heterocyclic groups.

An additional preferred embodiment of the current invention is a series of compounds having general Formula II:

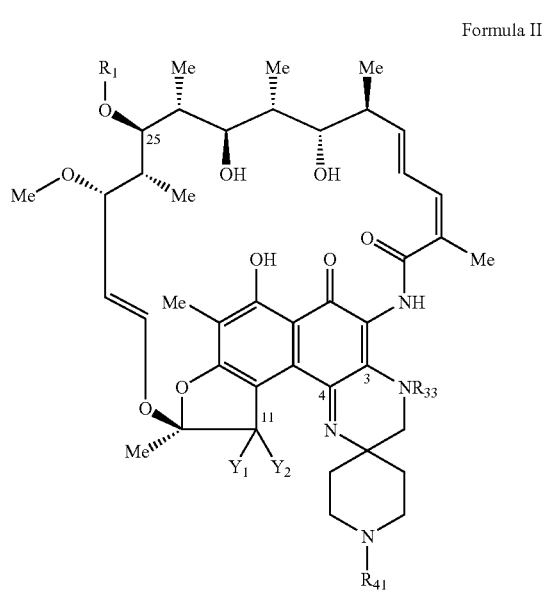

Formula II

An additional preferred embodiment of the current invention is a series of compounds having general Formula III:

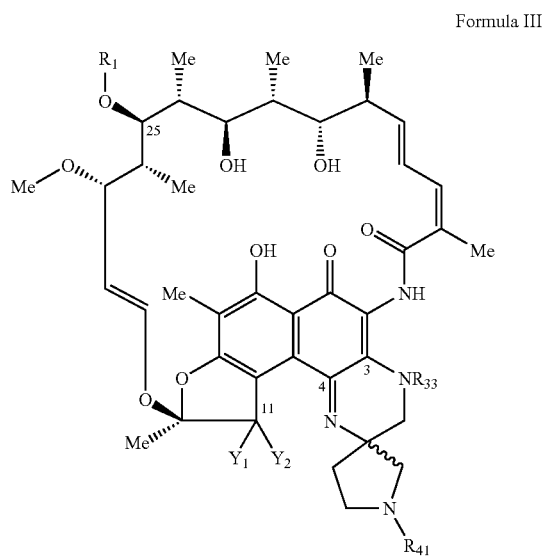

Formula III

An additional preferred embodiment of the current invention is a series of compounds having general Formula IV:

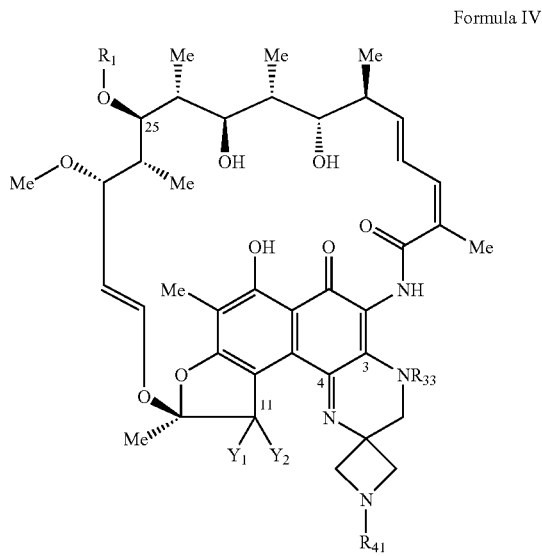

Formula IV

In general Formula II, Formula III, and Formula IV above, all substituents are defined as they were defined above with respect to general Formula I.

Preferred antibiotic compounds of the invention are as follows: 2',2'-Dimethyl-3,4-piperazinorifamycin S, 3,4-(2,2-Dimethyl-piperazino)-11-deoxy-11-hydroxyimino-rifamycin S, Spiro[N-methyl-piperidine-3,4-piperazinorifamycin S], Spiro[N-methyl-piperidine-3,4-piperazino-11-deoxy-11-hydroxyimino-rifamycin S], [N-Boc-piperidine-3,4-piperazinorifamycin S], Spiro[N-isobutyl-piperidine-3,4-piperazinorifamycin S], Spiro[N-allyl-piperidine-3,4-piperazinorifamycin S], Spiro[N-(quinolin-3-ylmethyl)-piperidine-3,4-piperazinorifamycin S], Spiro[N-benzyl-piperidine-3,4-piperazinorifamycin S], Spiro[N-(2,2,2-trichloro-1,1-dimethyl-ethoxycarbonyl)-piperidine-3,4-piperazinorifamycin S], Spiro[N-alloc-piperidine-3,4-piperazinorifamycin S], Spiro[piperidine-3,4-piperazinorifamycin S], Spiro[N-benzyl-pyrrolidine-3,4-piperazinorifamycin S], Spiro[N-methyl-pyrrolidine-3,4-piperazinorifamycin S], Spiro[N-isobutyl-pyrrolidine-3,4-piperazinorifamycin S], Spiro[N-(quinolin-3-ylmethyl)-pyrrolidine-3,4-piperazinorifamycin S], and Spiro[N-Boc-pyrrolidine-3,4-piperazinorifamycin S].

EXAMPLE 2

Administration to a Subject:

The pharmaceutical composition of the present invention comprises a therapeutically effective amount of a compound of the current invention formulated together with one or more pharmaceutically acceptable carriers. Injectable preparations can be formulated according to the known art using suitable dispersing or wetting agents and suspending agents. The sterile injectable preparation can also be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. In order to prolong the effect of a drug, it is often desirable to slow the absorption of the drug through subcutaneous or intramuscular injection. This can be accomplished by the use of a liquid suspension of crystalline or amorphous material with poor water solubility. The rate of absorption of the drug then depends upon its rate of dissolution which, in turn, can depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils, glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and the following: 1) fillers or extenders such as starches, lactose, sucrose, glucose, mannitol, and silicic acid, 2) binders such as, carboxymethylcellulose, alginates, gelatin, polyvinylpyrrolidinone, sucrose, and acacia, 3) humectants such as glycerol, 4) disintegrating agents such as agar-agar, calcium carbonate, potato or tapioca starch, alginic acid, certain silicates, and sodium carbonate, 5) solution retarding agents such as paraffin, 6) absorption accelerators such as quaternary ammonium compounds, 7) wetting agents such as, cetyl alcohol and glycerol monostearate, 8) absorbents such as kaolin and bentonite clay, and 9) lubricants such as talc, calcium stearate, magnesium stearate, solid polyethylene glycols, sodium lauryl sulfate, and mixtures thereof. In the case of capsules, tablets and pills, the dosage form can also comprise buffering agents. Solid compositions of a similar type can also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They can optionally contain opacifying agents and can also be of a composition that they release the active ingredient only, or preferentially, in a certain part of the intestinal tract, optionally, in a delayed manner. Examples of embedding compositions which can be used include polymeric substances and waxes. The active compounds can also be in microencapsulated form with one or more excipients as noted above.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as can be required. Ophthalmic formulation, ear drops, eye ointments, powders and solutions are also contemplated as being within the scope of this invention. The ointments, pastes, creams and gels can contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or animal by administering to the patient a therapeutically effective amount of a compound of the invention, in such amounts and for such time as is necessary to achieve the desired therapeutic effects. The term "therapeutically effective amount" of a compound of the invention is meant a sufficient amount of the compound to treat bacterial infections, at a reasonable benefit to risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or animals in single or in divided doses can be in amounts, for example, from 0.1 to 100 mg/kg body weight or preferably from 0.25 to 25 mg/kg body weight. Single dose compositions can contain such amounts or submultiples thereof to make up the daily dose. In general, treatment regimens according to the present invention comprise administration to an infected patient of such treatment from about 10 mg to about 2000 mg of the compounds of this invention per day in single or multiple doses. The compounds of current invention can be administrated orally, rectally, parenterally, intracistemally, intravaginally, intraperitoneally, topically, bucally, or as an oral or nasal spray.

Biological Activity:

Representative compounds were assayed for antimicrobial activity as follows: Minimum Inhibitory Concentrations (MICs) were determined by the microbroth dilution method as per NCCLS guidelines (National Committee for Clinical Laboratory Standards 2000), except that all growth incubations were conducted at 37° C. Bacterial cultures were tested in the following bacteriological media: S. aureus, S. epidermidis, and E. coli in Cation-Adjusted Mueller-Hinton Broth, S. pneumoniae in THY Broth supplemented with 1 mg/mL catalase under 5% $CO_2$ atmosphere, S. pyogenes in THY Broth, E. faecalis in BHI Broth, H. influenzae in BHI Broth supplemented with 0.75 µL of 1 mg/mL NAD and 150 µL of 1 mg/ml hematin per 5 mL, and M smegmatis in Middlebrook Broth plus ADC Enrichment. The antimicrobial activity of the example compounds of the current invention are shown in Table 1.

TABLE 1

Antimicrobial activity (MIC, mcg/ml) of selected compounds

| Organism | | Rifampin | Example 1–12 |
|---|---|---|---|
| Staphylococcus aureus ATCC29213 | rifS | 0.008 | 0.008–0.032 |
| Staphylococcus aureus ATCC29213 RpoB$^{H418Y}$ | rifR | 7.8 | 0.977–31.25 |
| Staphylococcus aureus ATCC29213 RpoB$^{D417Y}$ | rifR | >64 | 16–>250 |
| Staphylococcus epidermidis ATCC12228 | rifS | 0.03 | 0.00013–0.031 |
| Streptococcus pneumoniae ATCC6303 | rifS | 0.061 | 0.00025–0.063 |
| Streptococcus pyogenes ATCC19615 | rifS | 0.013 | 0.002–0.063 |
| Enterococcus faecalis ATCC29212 | rifS | 0.98 | 0.065–8 |
| Haemophilus influenzae ATCC10211 | rifS | 0.24 | 0.125–8 |
| Escherichia coli ATCC25922 | RifS | 16 | 2–>62.5 |
| Mycobacterium smegmatis ATCC700084 | rifS | 64 | 1–>64 |

Most importantly, compounds of the current invention demonstrate excellent activity against rifampin-resistant organisms. S. aureus ATCC 29213 RpoB$^{H418Y}$ is a rifampin-resistant strain with a mutation in RNA polymerase. This mutation results in a significant increase in the MIC for rifampin to about 8 µg/ml. Compounds of the current invention exhibit potent activity against this strain with a MIC as low as 1 µg/ml. S. aureus ATCC 29213 RpoB$^{D417Y}$ is a high level rifampin-resistant strain due to a RNA polymerase mutation with a MIC>64 µg/ml for rifampin. Compounds of the current invention are active against this highly rifampin-resistant strain with MICs as low as 16 µg/ml.

EXAMPLE 3

Synthetic Methods

The compounds of the current invention can be better understood in connection with the following synthetic schemes. The synthetic procedures shown in Schemes 1 to 5 are for illustration purposes and are not intended to limit the scope of the invention. It will be apparent to one skilled in the art that the compounds of the current invention can be prepared by a variety of synthetic routes, including but not limited to substitution of appropriate reagents, solvents or catalysts, change of reaction sequence, and variation of protecting groups.

Figure 2:
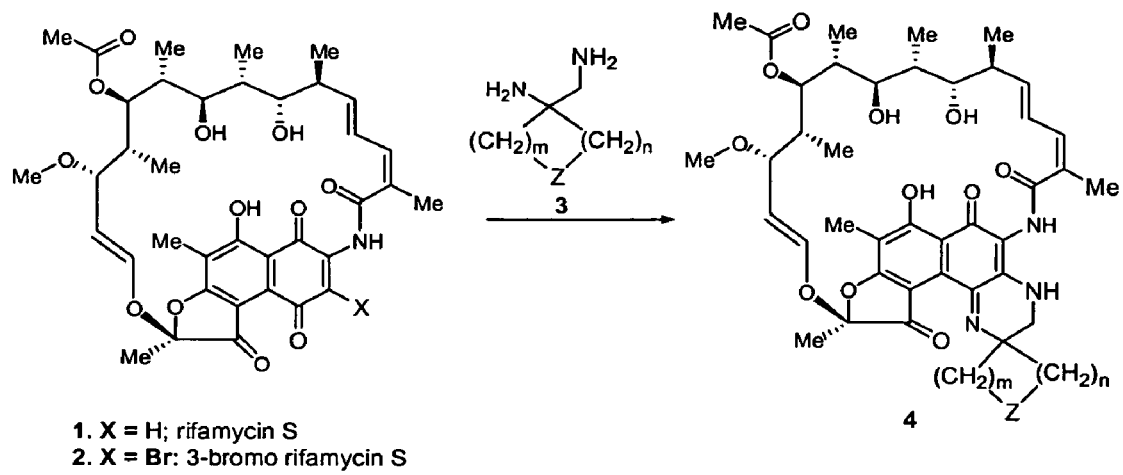
FIG. 2 shows Scheme 1, wherein a core skeleton of Formula I is constructed.

Scheme 1, shown in FIG. 2, shows the construction of the core skeleton of Formula I, in which the addition of 1,2-ethylenediamine (3) to rifamycin S (1) or 3-bromo-rifamycin (2) may afford the desired piperazinorifamycin (4). It has been known in the literature that the addition of aromatic 1,2-diamine such as 1,2-diaminotoluene, 2,3-diaminopyridine and 2-aminopyridine to rifamycin S (1) or 3-bromorifamycin (2) produces polyaromatic derivatives (U.S. Pat. No. 4,341,785; March et al. 1985). However, the addition of aliphatic 1,2-ethylenediamine (3) to rifamycin S (1) or 3-bromorifamycin (2) failed to give cyclization product. The aliphatic 1,2-ethylenediamine (3) first react as a reducing agent, which reduces rifamycin S (1) or 3-bromorifamycin (2) to the corresponding hydroquinone form and prevents addition and subsequent cyclization. This problem can be circumvented by the addition of Cu(II)Br, Cu(II)Cl, $K_3Fe(CN)_6$, or other proper oxidants that produce the desired cyclization product (4).

Figure 3:
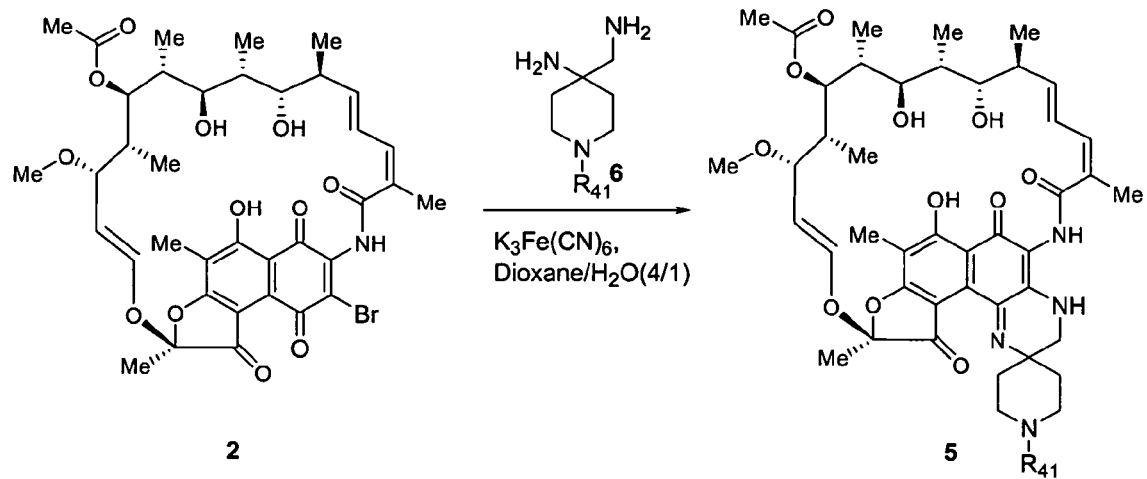
FIG. 3 shows Scheme 2, wherein the spiro[5,5] skeleton is constructed.

Scheme 2, shown in FIG. 3, illustrates the construction of the spiro[5,5] skeleton. The reaction of the diamine (6), prepared in Scheme 3 below, and 3-bromorifamycin (2) in the presence of $K_3Fe(CN)_6$ produces the desired piperazinorifamycin (5). $R_{41}$ can be a protecting group such as tert-butoxycarbonyl, allyloxycarbonyl, 2,2,2-trichloro-1,1-dimethylethoxycarbonyl, or a substituent such as methyl, isobutyl, allyl, 3-quinolinemethyl, and various other groups. After cyclization, the protecting group can be removed under proper conditions and release the amino group, which can be further converted to the other substituents by acylation, $S_N^2$ alkylation, reductive alkylation, sulfonylation and other reaction.

Figure 4:
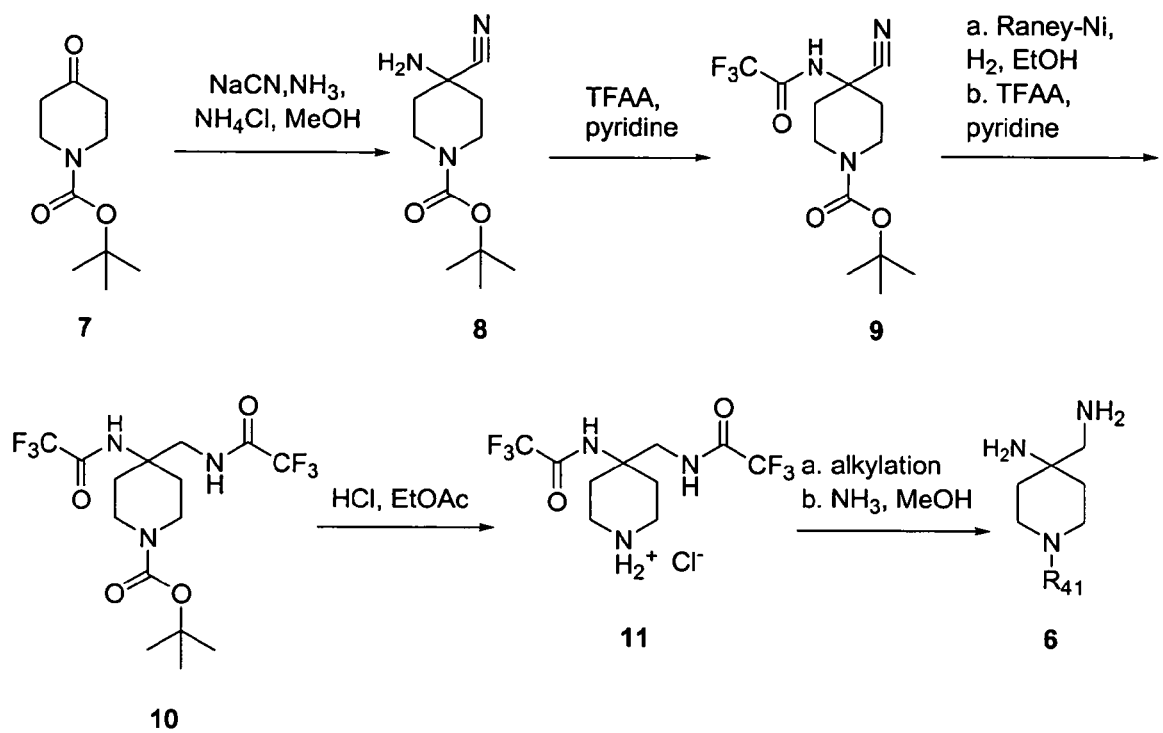
FIG. 4 shows Scheme 3, wherein the diamine is prepared from the protected piperidone.

As illustrated in Scheme 3, shown in FIG. 4, the diamine (6) can be prepared from the protected piperidone. The aminonitrile (8) was obtained by utilizing Strecker reaction from commercially available 4-BOC-piperidone (7). The reduction of the cyano group of aminonitrile (8) with Raney-Ni failed to give the desired diamine. Protection of the amino group of the aminonitrile (8) with trifluoroacetyl group and subsequent Raney-Ni reduction afforded the desired amine in good yield. In order to introduce various substituents to the piperidine nitrogen, the resulting free amino group was protected with trifluoroacetyl group to give compound (10). Treatment of compound (10) with 2N HCl in diethyl ether gave ammonium salts (11) in 84% yield. Compound (11) can serve as key intermediate for the introduction of various substituents to piperidine nitrogen. The introduction of various substituents by reductive amination, $S_N^2$ alkylation, acylation, sulfonylation and other synthetic methods and subsequent deprotection of the two trifluoroacetyl groups under basic condition can produce the desired diamine (6). Addition of diamine (6) to 3-bromorifamycin (2) can give the desired spiro-rifamycin derivatives (5). Alternatively, Boc group of compound (9) can be deprotected by the treatment of 2N HCl in diethyl ether and then a substituent can be introduced. In this case the substituent needs to be compatible with Raney-Ni reduction condition. Raney-Ni reduction of the resulting $R_{41}$ substituted amine and subsequent removal of trifluoroacetyl group under basic condition can produce the desired diamine (6).

Figure 5:
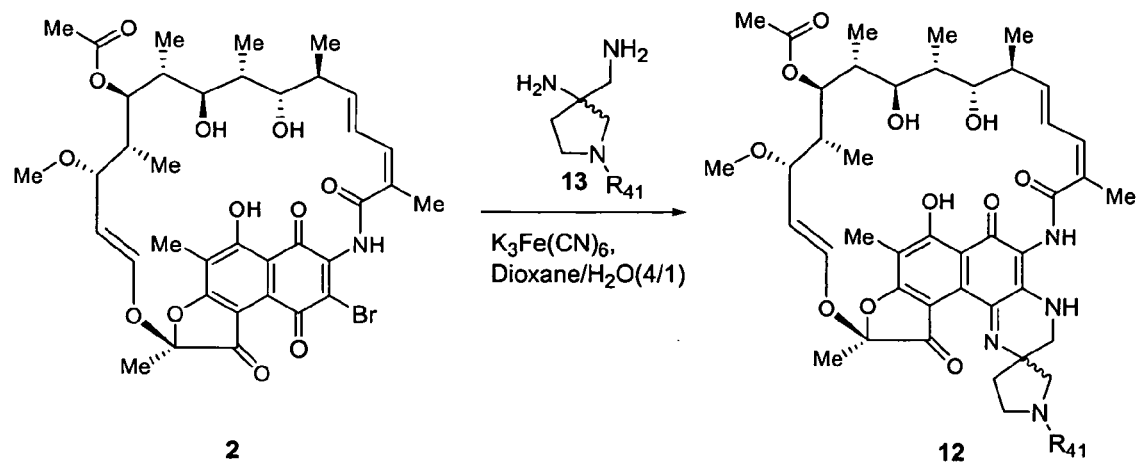
FIG. 5 shows Scheme 4, wherein the spiro[5,4] skeleton is constructed.

Scheme 4, shown in FIG. 5, illustrates the construction of spiro[5,4] skeleton of compound (12), which can be obtained by reacting diamine (13) and 3-bromorifamycin (2). The same methodology described in scheme 3 used for the preparation of diamine (6) can be used to prepare diamine (13). The addition of diamine (13) to 3-bromorifamycin (2) in the presence of $K_3Fe(CN)_6$ afforded the desired rifamycin derivatives (12). $R_{41}$ can be introduced through the same methodology described in the construction of rifamycin derivatives (5).

Figure 6:
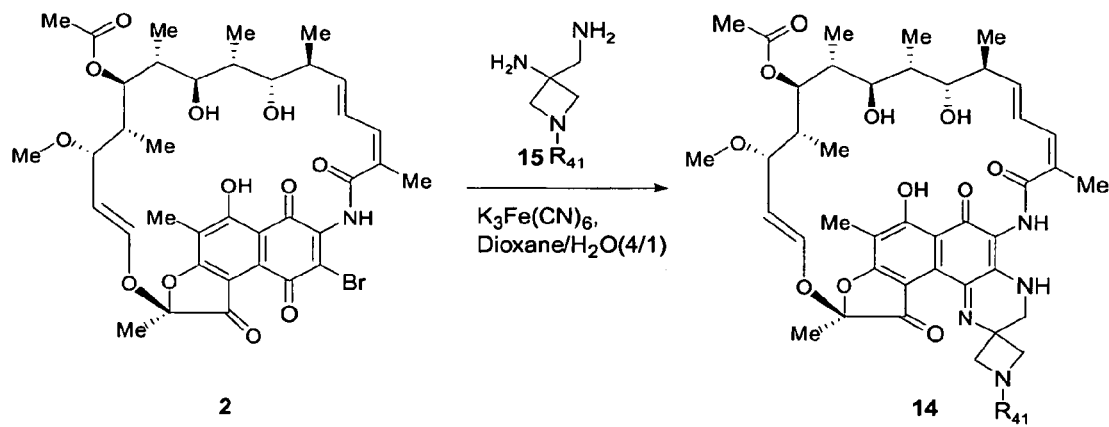
FIG. 6 shows Scheme 5, wherein the spiro[5,3] skeleton is constructed.

Scheme 5, shown in FIG. 6, illustrates the construction of spiro[5,3] skeleton of compound (14), which may be obtained by reacting diamine (15) and 3-bromorifamycin (2).

Specific Compositions

The compounds of the current invention may be better understood with reference to the following specific examples, which are representative of some of the embodiments of the invention, and are not intended to limit the invention.

All starting material used in these examples are either purchased from commercial sources or prepared according to published procedures. Operations involving moisture and/or oxygen sensitive materials are conducted under an atmosphere of nitrogen. Flash chromatography is performed using silica gel 60 as normal phase adsorbent or $C_{18}$ silica gel as reverse phase adsorbent. Thin layer chromatography ("TLC") and preparative thin layer chromatography ("PTLC") are performed using pre-coated plates purchased from E. Merck and spots are visualized with ultraviolet light followed by an appropriate staining reagent. Nuclear magnetic resonance ("NMR") spectra are recorded on a Varian 400 MHz magnetic resonance spectrometer. $^1H$ NMR chemical shift are given in parts-per million ($\delta$) downfield from TMS using the residual solvent signal ($CHCl_3=\delta$ 7.26, $CH_3OH=\delta$ 3.31) as internal standard. $^1H$ NMR information is tabulated in the following format: number of protons, multiplicity (s, singlet; d, doublet; t, triplet; q, quartet; m, multiplet; td, triplet of doublet; dt, doublet of triplet), coupling constant (s) (J) in hertz. The prefix app is occasionally applied in cases where the true signal multiplicity is unresolved and prefix br indicates a broad signal. Electro spray ionization mass spectra are recorded on a Finnegan LCQ advantage spectrometer.

EXAMPLE 4

2',2'-Dimethyl-3,4-piperazinorifamycin S

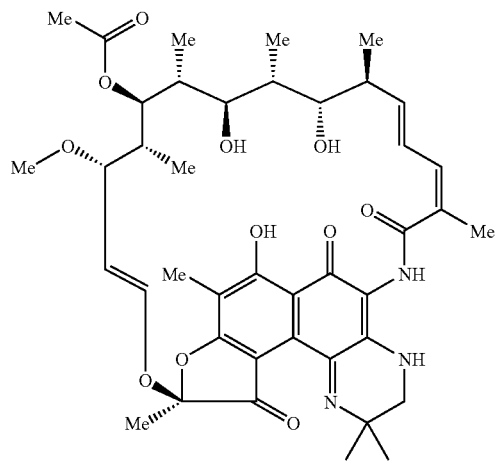

Synthesis: To a solution of 1,2-diamino-2-methyl propane (917 mg, 10.4 mmol) in dioxane (15 mL) were added $CuBr_2$ (580 mg, 2.6 mmol) and 3-bromorifamycin S (1 g, 1.3 mmol) and the mixture was stirred overnight at room temperature. The reaction mixture was cooled to 0° C. and quenched with 0.5 N HCl. The mixture was diluted with ethyl acetate and washed with 0.5 N HCl and saturated brine. The organic layer was dried over $Na_2SO_4$, filtered and evaporated. The residue was purified with silica gel column chromatography (hexanes:ethyl acetate=1:1+0.1% AcOH) to give the desired product (310 mg, 31%) as a dark red solid. ESI MS m/z 764 (M+H$^+$); $^1$H NMR (400 MHz, CDCl$_3$) δ 13.85 (s, 1H), 8.06 (s, 1H), 7.34 (s, 1H), 6.41 (dd, J=15.2 Hz and 10.8 Hz, 1H), 6.22 (d, J=10.4 Hz, 1H), 6.10 (dd, J=6.4 Hz and 15.2 Hz, 1H), 6.01 (d, J=12.4 Hz, 1H), 5.05 (dd, J=5.0 Hz and 12.4 Hz, 1H), 4.96 (d, J=10.0 Hz, 1H), 3.84 (br s, 1H), 3.74 (d, J=8.4 Hz, 1H), 3.53 (br s, 1H), 3.37 (br s, 1H), 3.32–3.27 (m, 1H), 3.08–2.97 (m, 2H), 3.03 (s, 3H), 2.34 (m, 1H), 2.22 (s, 3H), 2.02 (s, 3H), 2.01 (s, 3H), 1.79–1.50 (m, 3H), 1.72 (s, 3H), 1.59 (s, 3H), 1.24 (s, 3H), 1.01 (d, J=6.8 Hz, 3H), 0.82 (d, J=6.8 Hz, 3H), 0.63 (d, J=6.4 Hz, 3H), 0.01 (d, J=7.2 Hz, 3H).

EXAMPLE 5

3,4-(2,2-Dimethyl-piperazino)-11-deoxy-11-hydroxyimino-rifamycin S:

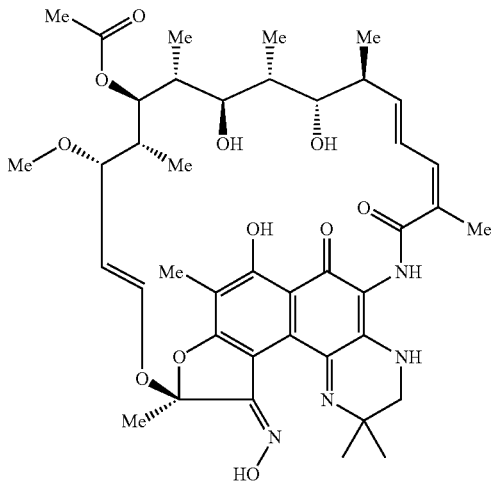

Synthesis: To a stirred solution of 2',2'-dimethyl-3,4-piperazinorifamycin S (5.0 mg, 0.006 mmol) in MeOH (0.4 mL) was added pyridine (2 μL, 0.025 mmol) and hydroxylamine hydrochloride (3.0 mg, 0.043 mmol). The reaction mixture was stirred for six days at room temperature. The reaction mixture was purified by preparative thin layer chromatography (methylene chloride:methanol=9:1) to give the desired product as a purple solid (1.2 mg, 24%). ESI MS m/z 779 (M+H)$^+$; $^1$H NMR (400 MHz, CDCl$_3$) δ 13.94 (s, 1H), 8.55 (s, 1H), 7.68 (s, 1H), 6.45 (dd, J=11.2 and 15.6 Hz, 1H), 6.31 (d, J=10.4 Hz, 1H), 6.25 (d, J=12.8 Hz, 1H), 6.04 (dd, J=6.4 and 12.8 Hz, 1H), 5.28 (dd, J=8.4 and 12.4 Hz, 1H), 4.71 (d, J=10.4 Hz, 1H), 3.70 (d, J=10.4 Hz, 1H), 3.62 (d, J=8.8 Hz, 1H), 3.53 (br s, 1H), 3.44–3.36 (m, 3H), 3.26 (dd, J=4.0 and 10.8 Hz, 1H), 3.11 (s, 3H), 3.05–3.00 (m, 1H), 2.43–2.37 (m, 1H), 2.32 (s, 3H), 2.12 (s, 3H), 2.08 (s, 3H), 2.05 (s, 3H), 2.04–1.98 (m, 1H), 1.80 (s, 3H), 1.75 (s, 3H), 1.52–1.46 (m, 1H), 1.05 (d, J=7.2 Hz, 3H), 0.86 (d, J=6.8 Hz, 3H), 0.68 (d, J=6.8 Hz, 3H), 0.08 (d, J=6.8 Hz, 3H).

EXAMPLE 6

Spiro[N-methyl-piperidine-3,4-piperazinorifamycin S]:

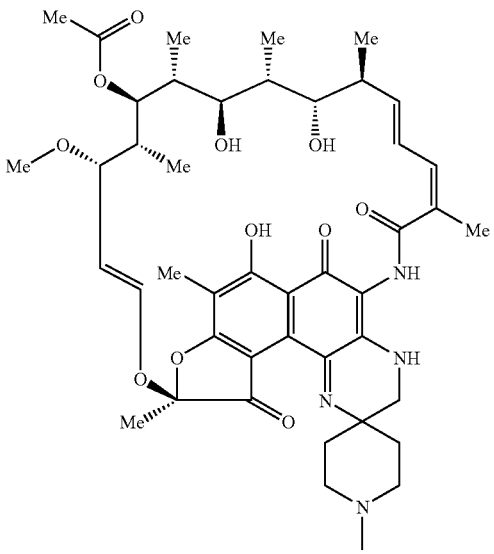

Synthesis: Step 1. 4-Amino-4-cyano-piperidine-1-carboxylic acid tert-butyl ester: To a mixture of N-Boc-piperidone (10 g, 50 mmol), ammonium chloride (2.9 g, 55 mmol) and sodium cyanide (2.7 g, 55 mmol) was added 2 M NH$_3$ in MeOH (115 mL) and the mixture was refluxed for 3 h and cooled to room temperature. Another 2M NH$_3$ in MeOH (110 mL) was added and refluxed for 3 h again. The reaction mixture was cooled to room temperature and methanol was removed under reduced pressure. The residue was dissolved in ethyl acetate and washed with water and saturated brine. The organic layer was dried over MgSO$_4$, filtered and evaporated to give 12 g of the desired product that was used without further purification. $^1$H NMR (400 MHz, CDCl$_3$) δ 3.95 (br d, J=11.6 Hz, 2H), 3.22–3.16 (m, 2H), 1.96 (br d, J=13.2 Hz, 2H), 1.80 (br s, 2H), 1.67–1.60 (m, 2H), 1.46 (s, 9H); $^{13}$C NMR (100 MHz, CDCl$_3$) δ 154.3, 123.0, 80.0, 49.7, 39.9 (2C), 36.7 (2C), 28.3 (3C).

Step 2. 4–Cyano-4-(2,2,2-trifluoro-acetylamino)-piperidine-1-carboxylic acid tert-butyl ester: To a cold (0° C.) solution of 4-amino-4-cyano-piperidine-1-carboxylic acid tert-butyl ester (8.7 g, 38.6 mmol) in pyridine (80 mL) was added trifluoroacetic anhydride (8 mL, 58 mmol) and warmed to room temperature over 2 h and the mixture was stirred overnight. The reaction mixture was diluted with ethyl acetate and washed with 1 N HCl five times and then washed with saturated brine. The organic layer was dried over MgSO$_4$, filtered and evaporated to give white solid, which was purified by recrystalization from hexanes/ethyl acetate to give the desired product (7 g, 56%) as a white solid. $^1$H NMR (400 MHz, CD$_3$OD) δ 4.00 (dt, J=14.4 Hz and 3.6 Hz, 2H), 3.20 (br s, 2H), 2.38 (br d, J=13.2 Hz, 2H), 1.90–1.82 (m, 2H), 1.46 (s, 9H); $^{13}$C NMR (100 MHz, CD$_3$OD) δ 158.5 (q, J=37.4 Hz), 156.1, 118.8, 116.9 (q, J=285.0 Hz), 81.9, 52.6, 41.2 (br d, J=66.3 Hz, 2C), 34.8 (2C), 28.7 (3C).

Step 3. 4-Aminomethyl-4-(2,2,2-trifluoro-acetylamino)-piperidine-1-carboxylic acid tert-butyl ester: To a solution of 4-cyano-4-(2,2,2-trifluoro-acetylamino)-piperidine-1-carboxylic acid tert-butyl ester (5.9 g, 18.4 mmol) in ethanol (60 mL) was added Raney nickel (3 g) and the mixture was stirred overnight under balloon of hydrogen at room temperature. The reaction mixture was filtered through celite and evaporated to give the desired amine (6 g, 100%) that was used without further purification. $^1$H NMR (400 MHz, CD$_3$OD) δ 3.63–3.57 (m, 2H), 3.37–3.30 (m, 2H), 3.34 (s, 2H), 1.54–1.38 (m, 4H), 1.45 (s, 9H); $^{13}$C NMR (100 MHz, CD$_3$OD) δ 159.8 (q, J=36.6 Hz), 156.4, 117.7 (q, J=285.1 Hz), 81.0, 52.4, 50.2, 40.7 (br d, J=89.2 Hz, 2C), 35.7 (2C), 28.9 (3C).

Step 4. 4-(2,2,2-Trifluoro-acetylamino)-4-[(2,2,2-trifluoro-acetylamino)-methyl]-piperidine-1-carboxylic acid tert-butyl ester: To a cold (0° C.) solution of 4-aminomethyl-4-(2,2,2-trifluoro-acetylamino)-piperidine-1-carboxylic acid tert-butyl ester (6 g, 18.5 mmol) in pyridine (80 mL) was added trifluoroacetic anhydride (4 mL, 28.8 mmol) and warmed to room temperature over 2 h and the mixture was stirred overnight. The reaction mixture was diluted with ethyl acetate and washed with 1 N HCl five times and then washed with saturated brine. The organic layer was dried over MgSO$_4$, filtered and evaporated to give the desired product (7 g, 88%) that was used without further purification. $^1$H NMR (400 MHz, CDCl$_3$) δ 7.63 (t, J=5.6 Hz, 1H), 6.48 (s, 1H), 3.76–3.73 (m, 4H), 3.18–3.11 (m, 2H), 2.08–2.03 (m, 2H), 1.74–1.67 (m, 2H), 1.45 (s, 9H); $^{13}$C NMR (100 MHz, CDCl$_3$) δ 158.6 (q, J=37.3 Hz), 158.0 (q, J=37.3 Hz), 154.8, 116.0 (q, J=285.8 Hz), 115.6 (q, J=286.5 Hz), 80.6, 60.8, 56.9, 39.2 (br d, J=70.1 Hz, 2C), 31.5 (2C), 28.4 (3C).

Step 5. 4-(2,2,2-Trifluoro-acetylamino)-4-[(2,2,2-trifluoro-acetylamino)-methyl]-piperidinium chloride: To a solution of 4-(2,2,2-trifluoro-acetylamino)-4-[(2,2,2-trifluoro-acetylamino)-methyl]-piperidine-1-carboxylic acid tert-butyl ester (5.1 g, 12.2 mmol) in ethyl acetate (40 mL) was added 2 N HCl in Et$_2$O (55 mL, 110 mmol) and the mixture was stirred overnight at room temperature. The reaction mixture was filtered and washed with ether to give the desired product (3.6 g, 84%) as a white solid. $^1$H NMR (400 MHz, CD$_3$OD) δ 9.55 (br s, 1H), 8.75 (s, 1H), 3.68 (s, 2H), 3.37–3.32 (m, 2H), 3.08–3.01 (m, 2H), 2.52 (br d, J=14.4 Hz, 2H), 1.90–1.82 (m, 2H).

Step 6. 2,2,2-Trifluoro-N-{1-methyl-4-[(2,2,2-trifluoro-acetylamino)-methyl]-piperidin-4-yl}-acetamide: To a cold (0° C.) solution of 4-(2,2,2-trifluoro-acetylamino)-4-[(2,2,2-trifluoro-acetylamino)-methyl]-piperidinium chloride (1 g, 2.8 mmol) in methanol (5 mL) was added formaldehyde (0.2 mL, 2.8 mmol) and NaOAc (689 mg, 8.4 mmol) and the mixture was stirred for 5 min, followed by the addition of AcOH (0.16 mL, 2.8 mmol) and NaCNBH$_3$ (211 mg, 3.4 mmol) and the reaction mixture was stirred for 4 h at 0° C. The methanol was removed under reduced pressure and the residue was diluted with ethyl acetate and washed with water and saturated NaHCO$_3$. The organic layer was dried over MgSO$_4$, filtered and evaporated to give 800 mg (85%) of the desired product that was used without further purification. $^1$H NMR (400 MHz, CD$_3$OD) δ 3.62 (s, 2H), 2.70 (br d, J=11.6 Hz, 2H), 2.34–2.28 (m, 2H), 2.28 (s, 3H), 2.18 (br t, J=11.6 Hz, 2H), 1.70–1.65 (m, 2H); ); $^{13}$C NMR (100 MHz, CD$_3$OD) δ 158.6 (q, J=36.6 Hz), 157.7 (q, J=36.6 Hz), 116.4 (q, J=285.8 Hz), 115.9 (q, J=286.6 Hz), 55.8, 50.6 (2C), 44.9 (2C), 30.8 (2C).

Step 7. 4-Aminomethyl-1-methyl-piperidin-4-ylamine: The solution of 2,2,2-trifluoro-N-{1-methyl-4-[(2,2,2,-trifluoro-acetylamino)-methyl]-piperidin-4-yl}-acetamide (730 mg, 2.2 mmol) in 7 N NH$_3$ in MeOH (20 mL) was refluxed overnight in a sealed tube. The reaction mixture was cooled to room temperature and evaporated to give 732 mg of the desired diamine that was used without further purification. $^1$H NMR (400 MHz, CD$_3$OD) δ 2.72 (s, 2H), 2.65–2.54 (m, 2H), 2.37 (m, 3H), 2.36–2.32 (m, 2H), 1.72–1.64 (m, 2H), 1.61–1.51 (m, 2H).

Step 8. Spiro[N-methyl-piperidine-3,4-piperazinorifamycin S]: To a solution of crude 4-aminomethyl-1-methyl-piperidin-4-ylamine (732 mg) in dioxane/H$_2$O (4/1) (5 mL) were added K$_3$Fe(CN)$_6$ (257 mg, 0.78 mol) and 3-bromorifamycin S (400 mg, 0.52 mmol) and the reaction mixture was stirred overnight at room temperature. The reaction mixture was cooled to 0° C. and quenched with saturated NH$_4$Cl. The mixture was diluted with ethyl acetate and washed with saturated NH$_4$Cl and saturated brine. The organic layer was dried over Na$_2$SO$_4$, filtered and evaporated. The residue was purified with preparative thin layer chromatography (methylene chloride:methanol=15:1+0.2% AcOH) to give the desired product (24 mg, 2.4%) as a dark red solid. ESI MS m/z 819 (M+H$^+$); $^1$H NMR (400 MHz, CDCl$_3$) δ 13.83 (br s, 1H), 8.18 (s, 1H), 7.21 (s, 1H), 6.46 (dd, J=10.8 Hz and 15.6 Hz, 1H), 6.26 (d, J=10.8 Hz, 1H), 6.11 (dd, J=16.0 Hz and 7.2 Hz, 1H), 5.99 (d, J=12.4 Hz, 1H), 5.04 (dd, J=12.0 Hz and 5.6 Hz, 1H), 4.99 (d, J=10.8 Hz, 1H), 3.78 (d, J=10.0 Hz, 1H), 3.72 (m, 1H), 3.48–3.40 (m, 3H), 3.28 (br d, J=11.2 Hz, 1H), 3.08–3.01 (m, 2H), 3.05 (s, 3H), 2.87 (br t, 1H), 2.73 (br s, 3H), 2.49 (br t, J=11.6 Hz, 1H), 2.39–2.34 (m, 2H), 2.24 (s, 3H), 2.16–2.02 (m, 4H), 2.05 (s, 3H), 2.02 (s, 3H), 1.79 (m, 1H), 1.72 (s, 3H), 1.65–1.62 (m, 2H), 1.02 (d, J=7.2 Hz, 3H), 0.85 (d, J=7.2 Hz, 3H), 0.65 (d, J=6.8 Hz, 3H), 0.01 (d, J=7.2 Hz, 3H).

EXAMPLE 7

Spiro [N-methyl-piperidine-3,4-piperazino-11-deoxy-11-hydroxyimino-rifamycin S]

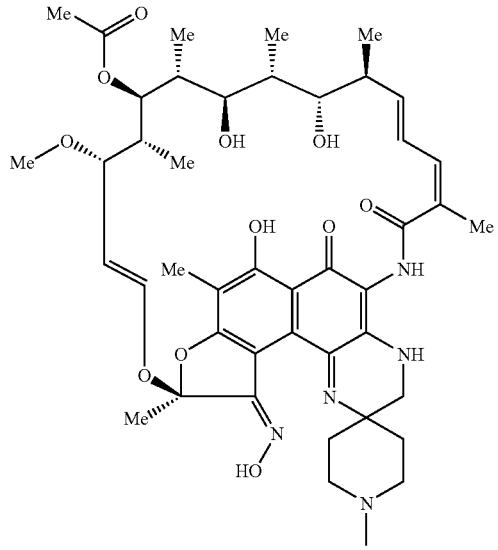

Synthesis: To a stirred solution of spiro[N-methyl-piperidine-3,4-piperazinorifamycin S] (7.0 mg, 0.009 mmol) in MeOH (0.3 mL) was added pyridine (3 μL, 0.037 mmol) and hydroxylamine hydrochloride (3.0 mg, 0.043 mmol). The reaction solution was stirred for six days at room temperature. The reaction mixture was purified by preparative thin layer chromatography (methylene chloride:methanol=9:1) to give the desired product as a purple solid (5.0 mg, 70%). ESI MS m/z 834.4 (M+H$^+$); $^1$H NMR 400 MHz, CDCl$_3$) δ 13.80 (s, 1H), 8.38 (s, 1H), 7.22 (s, 1H), 6.46 (dd, J=11.2 and 15.6 Hz, 1H), 6.30 (d, J=10.4 Hz, 1H), 6.11 (dd, J=6.4 and 14.4 Hz, 1H), 6.08 (d, J=12.4 Hz, 1H), 5.21 (dd, J=6.4 and 12.4 Hz, 1H), 4.97 (d, J=10.4 Hz, 1H), 3.88 (br s, 1H), 3.80 (d, J=9.6 Hz, 1H), 3.68 (br s, 1H), 3.44–3.35 (m, 2H), 3.16–3.10 (m, 1H), 3.10 (s, 3H), 3.08–3.03 (m, 1H), 2.85–2.78 (m, 1H), 2.66 (br s, 3H), 2.43–2.38 (m, 1H), 2.34 (s, 3H), 2.30–2.25 (m, 2H), 2.13 (s, 3H), 2.12–2.00 (m, 2H), 2.06 (s, 6H), 1.82–1.74 (m, 4H), 1.68–1.60 (m, 1H), 1.06 (d, J=7.2 Hz, 3H), 0.86 (d, J=6.8 Hz, 3H), 0.70 (d, J=6.8 Hz, 3H), 0.10 (d, J=7.2 Hz, 3H).

EXAMPLE 8

[N-Boc-piperidine-3,4-piperazinorifamycin S]

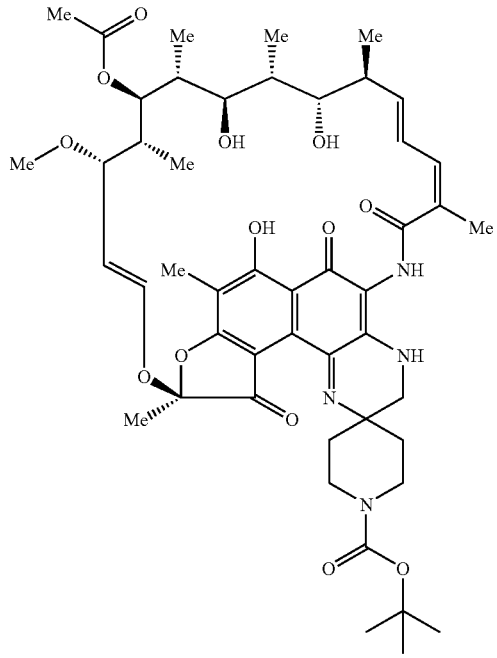

Synthesis: Step 1. 4-Amino-4-aminomethyl-piperidine-1-carboxylic acid tert-butyl ester: A solution of 4-aminomethyl-4-(2,2,2-trifluoro-acetylamino)-piperidine-1-carboxylic acid tert-butyl ester (400 mg, 1.2 mmol) in 10% K$_2$CO$_3$ in MeOH/H$_2$O (5/2) (5 mL) was refluxed overnight. The reaction mixture was cooled to room temperature and evaporated. The residue was dissolved in ethyl acetate and washed with water and saturated brine. The organic layer was dried over MgSO$_4$, filtered and evaporated to give 250 mg (91%) of the desired diamine that was used without further purification. $^1$H NMR (400 MHz, CD$_3$OD) δ 3.63–3.57 (m, 2H), 3.36 (s, 2H), 3.36–3.30 (m, 2H), 1.62–1.40 (m, 4H), 1.45 (s, 9H).

Step 2. Spiro[N-Boc-piperidine-3,4-piperazinorifamycin S]: To a solution of 4-amino-4-aminomethyl-piperidine-1-carboxylic acid tert-butyl ester (250 mg, 1.1 mmol) in dioxane (1.5 mL) were added CuBr$_2$ (14 mg, 0.06 mmol) and 3-bromorifamycin S (70 mg, 0.09 mmol) and the reaction mixture was stirred overnight at room temperature. The reaction mixture was cooled to 0° C. and quenched with 0.5 N HCl. The mixture was diluted with ethyl acetate and washed with 0.5 N HCl and saturated brine. The organic layer was dried over Na$_2$SO$_4$, filtered and evaporated. The residue was purified with preparative thin layer chromatography (hexanes:ethyl acetate=1:1+0.1% AcOH) to give the desired product (8.7 mg, 11%) as a dark red solid. ESI MS m/z 905 (M+H$^+$); $^1$H NMR (400 MHz, CDCl$_3$) δ 13.86 (s, 1H), 8.28 (s, 1H), 7.78 (s, 1H), 6.42 (dd, J=15.6 Hz and 11.2 Hz, 1H), 6.26 (d, J=10.4 Hz, 1H), 6.13 (dd, J=15.6 Hz and 7.2 Hz, 1H), 6.03 (d, J=12.8 Hz, 1H), 5.07 (dd, J=13.2 Hz and 5.6 Hz, 1H), 5.00 (d, J=10.0 Hz, 1H), 3.94–3.70 (m, 8H), 3.41–3.30 (m, 2H), 3.10–3.04 (m, 1H), 3.07 (s, 3H), 2.36–2.41 (m, 1H), 2.25 (s, 3H), 2.10 (s, 3H), 2.05 (s, 3H), 1.95–1.60 (m, 7H), 1.34 (s, 3H), 1.46 (s, 9H), 1.04 (d, J=7.2 Hz, 3H), 0.85 (d, J=6.4 Hz, 3H), 0.66 (d, J=6.8 Hz, 3H), 0.04 (d, J=7.2 Hz, 3H).

EXAMPLE 9

Spiro[N-isobutyl-piperidine-3,4-piperazinorifamycin S]:

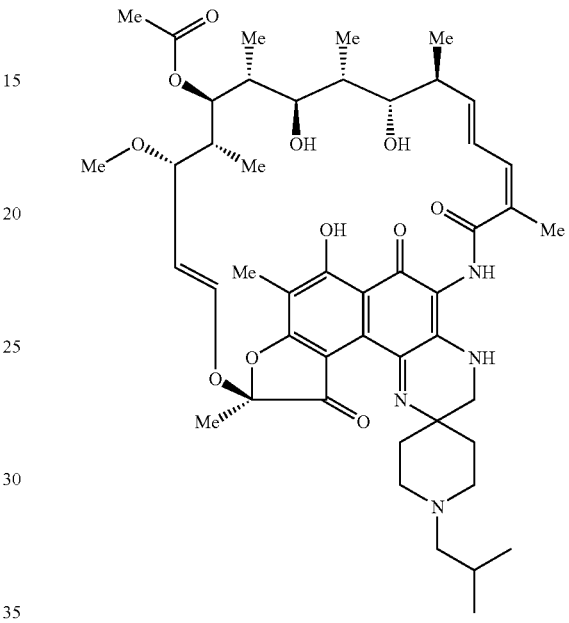

Synthesis: Step 1. 2,2,2-Trifluoro-N-{1-isobutyl-4-[(2,2,2,-trifluoro-acetylamino)-methyl]-piperidin-4-yl}-acetamide: To a solution of 4-(2,2,2-trifluoro-acetylamino)-4-[(2,2,2-trifluoro-acetylamino)-methyl]-piperidinium chloride (500 mg, 1.4 mmol) in DMF (4 mL) was added K$_2$CO$_3$ (967 mg, 7.0 mmol) and isobutyl bromide (1 mL, 5.4 mmol) and the reaction mixture was stirred for 3 d at 50° C. The reaction mixture was cooled to room temperature and diluted with ethyl acetate and washed with saturated brine. The organic layer was dried over MgSO$_4$, filtered and evaporated to give 450 mg (85%) of the desired product that was used without further purification. $^1$H NMR (400 MHz, CDCl$_3$) δ 7.98 (s, 1H), 6.64 (s, 1H), 3.69 (d, J=6.0 Hz, 2H), 2.64–2.60 (m, 2H), 2.17–2.07 (m, 4H), 2.08 (d, J=7.2 Hz, 2H), 1.82–1.72 (m, 2H), 0.86 (d, J=6.8 Hz, 6H).

Step 2. 4-Aminomethyl-1-isobutyl-piperidin-4-ylamine: The solution of 2,2,2-trifluoro-N-{1-isobutyl-4-[(2,2,2,-trifluoro-acetylamino)-methyl]-piperidin-4-yl}-acetamide (450 mg, 1.2 mmol) in 7 N NH$_3$ in MeOH (8 mL) was refluxed overnight in a sealed tube. The reaction mixture was cooled to room temperature and evaporated to give 380 mg of the desired diamine that was used without further purification. $^1$H NMR (400 MHz, CD$_3$OD) δ 2.73 (s, 2H), 2.65–2.48 (m, 4H), 4.44 (d, J=7.2 Hz, 2H), 1.86–1.56 (m, 5H), 0.92 (d, J=6.8 Hz, 6H).

Step 3. Spiro[N-isobutyl-piperidine-3,4-piperazinorifamycin S]: To a solution of crude 4-aminomethyl-1-isobutyl-piperidin-4-ylamine (380 mg) in dioxane/H$_2$O (4/1) (1.5 mL) were added K$_3$Fe(CN)$_6$ (89 mg, 0.27 mol) and 3-bromorifamycin S (70 mg, 0.09 mmol) and the reaction mixture was stirred overnight at room temperature. The reaction mixture was cooled to 0° C. and quenched with saturated NH$_4$Cl. The mixture was diluted with ethyl acetate and washed with saturated NH₄Cl and saturated brine. The organic layer was dried over Na₂SO₄, filtered and evaporated. The residue was purified with preparative thin layer chromatography (methylene chloride:methanol: AcOH=200:10:0.4) to give the desired product (5.8 mg, 7.5%) as a dark red solid. ESI MS m/z 861 (M+H⁺); ¹H NMR (400 MHz, CDCl₃) δ 13.93 (s, 1H), 8.36 (s, 1H), 7.13 (s, 1H), 6.39 (dd, J=12.0 Hz and 10.8 Hz, 1H), 6.22 (dd, J=10.4 Hz and 0.8 Hz, 1H), 6.09 (dd, J=16.0 Hz and 7.2 Hz, 1H), 6.01 (dd, J=12.4 Hz and 1.2 Hz, 1H), 5.06 (dd, J=12.8 Hz and 6.0 Hz, 1H), 4.98 (d, J=10.4 Hz, 1H), 3.92 (br s, 1H), 3.76 (d, J=10.0 Hz, 1H), 3.69 (br s, 1H), 3.45–3.37 (m, 4H), 3.08–2.99 (m, 2H), 3.04 (s, 3H), 2.69 (br s, 1H), 2.53 (br s, 1H), 2.41–2.33 (m, 2H), 2.22 (s, 3H), 2.22–2.15 (m, 3H), 2.02 (s, 6H), 2.20–1.60 (m, 6H), 1.72 (s, 3H), 1.02 (d, J=6.8 Hz, 3H), 0.89 (d, J=6.8 Hz, 6H), 0.83 (d, J=6.4 Hz, 3H), 0.64 (d, J=7.2 Hz, 3H), 0.01 (d, J=7.2 Hz, 3H).

EXAMPLE 10

Spiro[N-allyl-piperidine-3,4-piperazinorifamycin S]

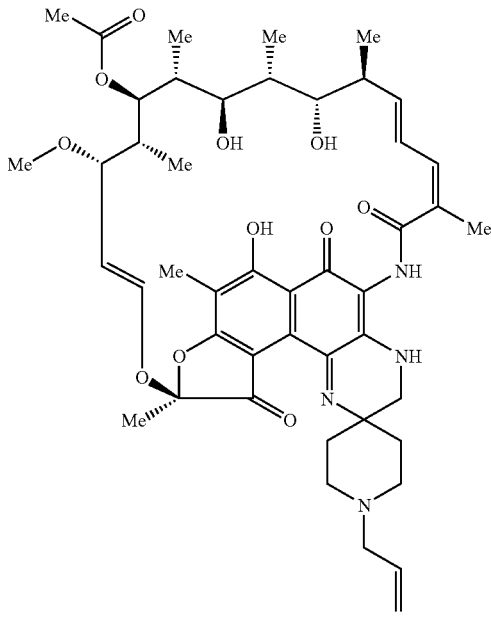

Synthesis: Step 1. N-{1-Allyl-4-[(2,2,2-trifluoro-acetylamino)-methyl]-piperidin-4-yl}-2,2,2-trifluoro-acetamide: To a solution of 4-(2,2,2-trifluoro-acetylamino)-4-[(2,2,2-trifluoro-acetylamino)-methyl]-piperidinium chloride (1 g, 2.8 mmol) in DMF (5 mL) was added K₂CO₃ (1.9 mg, 14 mmol) and allyl bromide (0.2 mL, 2.5 mmol) and the reaction mixture was stirred overnight at room temperature. The reaction mixture was diluted with ethyl acetate and washed with saturated brine. The organic layer was dried over MgSO₄, filtered and evaporated to give 1 g of the desired product that was used without further purification. ¹H NMR (400 MHz, CDCl₃) δ 7.95 (s, 1H), 6.66 (s, 1H), 5.83–5.76 (m, 1H), 5.19–5.12 (m, 2H), 3.68 (d, J=6.0 Hz, 2H), 2.98 (dt, J=6.8 Hz and 1.2 Hz, 2H), 2.68–2.65 (m, 2H), 2.20–2.12 (m, 4H), 1.81–1.74 (m, 2H).

Step 2. 1-Allyl-4-aminomethyl-piperidin-4-ylamine: The solution of N-{1-allyl-4-[(2,2,2-trifluoro-acetylamino)-methyl]-piperidin-4-yl}-2,2,2-trifluoro-acetamide (1 g, 2.8 mmol) in 7 N NH₃ in MeOH (11 mL) was refluxed overnight in a sealed tube. The reaction mixture was cooled to room temperature and evaporated to give 960 mg of the desired diamine that was used without further purification. ¹H NMR (400 MHz, CD₃OD) δ 5.88 (m, 1H), 5.26–5.19 (m, 2H), 3.29 (s, 2H), 3.09–3.04 (m, 2H), 2.64–2.45 (m, 4H), 1.69–1.51 (m, 4H).

Step 3. Spiro[N-allyl-piperidine-3,4-piperazinorifamycin S]: To a solution of crude 1-allyl-4-aminomethyl-piperidin-4-ylamine (200 mg) in dioxane/H₂O (4/1) (3 mL) were added K₃Fe(CN)₆ (95 mg, 0.29 mol) and 3-bromorifamycin S (150 mg, 0.19 mmol) and the reaction mixture was stirred overnight at room temperature. The reaction mixture was cooled to 0° C. and quenched with saturated NH₄Cl. The mixture was diluted with ethyl acetate and washed with saturated NH₄Cl and saturated brine. The organic layer was dried over Na₂SO₄, filtered and evaporated. The residue was purified with preparative thin layer chromatography (methylene chloride:methanol: AcOH=150:10:0.3) to give the desired product (5.1 mg, 3%) as a dark red solid. ESI MS m/z 845 (M+H⁺); ¹H NMR (400 MHz, CDCl₃) δ 13.81 (s, 1H), 8.13 (s, 1H), 7.30 (s, 1H), 6.40 (dd, J=16.0 Hz and 10.8 Hz, 1H), 6.23 (d, J=10.0 Hz, 1H), 6.10 (dd, J=15.6 Hz and 6.8 Hz, 1H), 6.02 (dd, J=12.4 Hz and 1.2 Hz, 1H), 5.93–5.87 (m, 1H), 5.23 (d, J=15.6 Hz, 2H), 5.07 (dd, J=12.4 Hz and 6.2 Hz, 1H), 4.96 (d, J=10.4 Hz, 1H), 3.75 (d, J=10.4 Hz, 1H), 3.38–3.33 (m, 2H), 3.23 (br s, 2H), 3.06–3.00 (m, 2H), 3.04 (s, 3H), 2.83–2.49 (m, 6H), 2.39–2.33 (m, 1H), 2.24 (s, 3H), 2.12–1.88 (m, 6H), 2.01 (s, 6H), 1.78–1.59 (m, 2H), 1.71 (s, 3H), 1.02 (d, J=6.8 Hz, 3H), 0.83 (d, J=7.2 Hz, 3H), 0.64 (d, J=7.2 Hz, 3H), 0.01 (d, J=7.2 Hz, 3H).

EXAMPLE 11

Spiro [N-(quinolin-3-ylmethyl)-piperidine-3,4-piperazinorifamycin S]

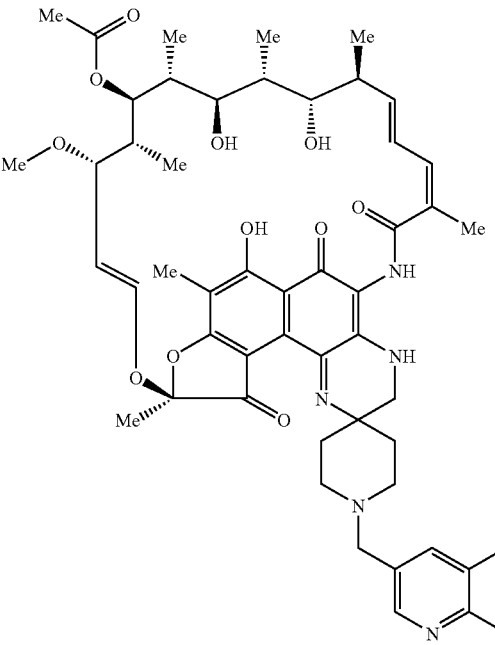

Synthesis: Step 1. 2,2,2-Trifluoro-N-{1-quinolin-3-ylm-ethyl-4-[(2,2,2-trifluoro-acetylamino)-methyl]-piperidin-4-yl}-acetamide: To a cold (0° C.) solution of 4-(2,2,2-trifluoro-acetylamino)-4-[(2,2,2-trifluoro-acetylamino)-methyl]-piperidinium chloride (450 mg, 1.3 mmol) in methanol (4 mL) was added 3-quinolinecarboxaldehyde (198 mg, 1.3 mmol) and NaOAc (310 mg, 3.8 mmol) and the reaction mixture was stirred for 5 min, followed by the addition of AcOH (0.07 mL, 1.3 mmol) and NaCNBH$_3$ (95 mg, 1.5 mmol) and the mixture was stirred for 4 h at 0° C. The MeOH was removed under reduced pressure and the residue was diluted with ethyl acetate and washed with water and saturated NaHCO$_3$. The organic layer was dried over MgSO$_4$, filtered and evaporated to give 450 mg (77%) of the desired product that was used without further purification.

Step 2. 4-Aminomethyl-1-quinolin-3-ylmethyl-piperidin-4-ylamine: The solution of 2,2,2-trifluoro-N-{1-quinolin-3-ylmethyl-4-[(2,2,2-trifluoro-acetylamino)-methyl]-piperi-din-4-yl}-acetamide (450 mg, 1.3 mmol) in 7 N NH$_3$ in MeOH (10 mL) was refluxed overnight in a sealed tube. The reaction mixture was cooled to room temperature and evaporated to give 435 mg of the desired diamine that was used without further purification. $^1$H NMR (400 MHz, CD$_3$OD) δ 8.86 (t, J=2.4 Hz, 1H), 8.31–8.29 (m, 1H), 8.02 (dd, J=8.4 Hz and 3.6 Hz, 1H), 7.94 (d, J=8.0 Hz, 1H), 7.79–7.73 (m, 1H), 7.65–7.59 (m, 1H), 3.85 (s, 2H), 3.63 (s, 2H), 3.37–3.32 (m, 2H), 3.08–3.01 (m, 2H), 2.42–2.33 (m, 2H), 1.76–1.69 (m, 2H).

Step 3. Spiro[N-(quinolin-3-ylmethyl)-piperidine-3,4-piperazinorifamycin S]: To a solution of crude 4-aminomethyl-1-quinolin-3-ylmethyl-piperidin-4-ylamine (435 mg) in dioxane/H$_2$O (4/1) (2 mL) were added K$_3$Fe(CN)$_6$ (66 mg, 0.2 mmol) and 3-bromorifamycin S (156 mg, 0.2 mmol) and the reaction mixture was stirred overnight at room temperature. The reaction mixture was cooled to 0° C. and quenched with saturated NH$_4$Cl. The mixture was diluted with ethyl acetate and washed with saturated NH$_4$Cl and saturated brine. The organic layer was dried over Na$_2$SO$_4$, filtered and evaporated. The residue was purified with pre-parative thin layer chromatography (methylene chloride: methanol:AcOH=150:10:0.4) to give the desired product (3.1 mg, 1.6%) as a dark red solid. ESI MS m/z 946 (M+H$^+$); $^1$H NMR (400 MHz, CDCl$_3$) δ 13.84 (s, 1H), 8.87 (s, 1H), 8.23 (br s, 1H), 8.20 (s, 1H), 8.10 (d, J=8.4 Hz, 1H), 7.82 (d, J=8.0 Hz, 1H), 7.72 (t, J=8.4 Hz, 1H), 7.56 (t, J=8.0 Hz, 1H), 7.27 (br s, 1H), 6.41 (dd, J=10.8 Hz and 16.0 Hz, 1H), 6.24 (d, J=10.8 Hz, 1H), 6.10 (dd, J=16.0 Hz and 6.8 Hz, 1H), 6.01 (dd, J=12.4 Hz and 1.2 Hz, 1H), 5.06 (dd, J=12.8 Hz and 6.4 Hz, 1H), 4.97 (d, J=10.4 Hz, 1H), 3.96 (s, 2H), 3.76 (d, J=10.0 Hz, 1H), 3.41–3.36 (m, 2H), 3.25 (br s, 1H), 3.05 (s, 3H), 3.02 (m, 2H), 2.81 (br s, 1H), 2.58 (br s, 1H), 2.40–2.34 (m, 1H), 2.24 (s, 3H), 2.18–2.00 (m, 8H), 2.03 (s, 3H), 2.02 (s, 3H), 1.91 (br s, 1H), 1.79–1.77 (m, 1H), 1.64 (s, 3H), 1.03 (d, J=7.2 Hz, 3H), 0.83 (d, J=7.2 Hz, 3H), 0.64 (d, J=6.4 Hz, 3H), 0.01 (d, J=7.2 Hz, 3H).

EXAMPLE 12

Spiro[N-benzyl-piperidine-3,4-piperazinorifamycin S]

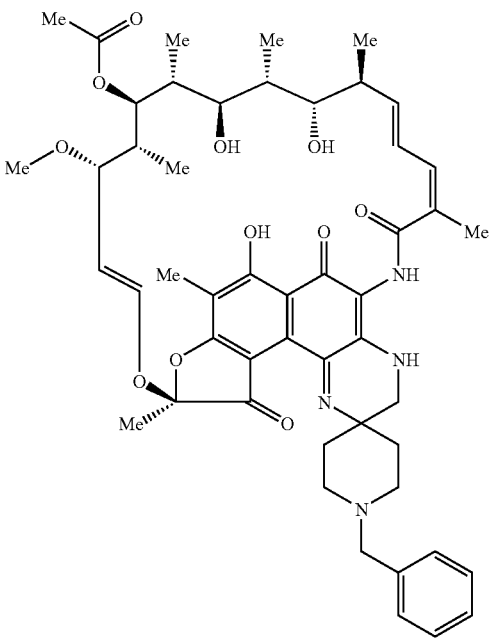

Synthesis: Step 1. 4-Amino-1-benzyl-piperidine-4-carbonitrile: To a solution of ammonium chloride (5.7 g, 105.6 mmol) and potassium cyanide (6.9 mg, 105.6 mmol) in water (155 mL) was added 1-benzyl-4-piperidone (5 g, 26.4 mmol) and the mixture was stirred for 6 days. It was cooled to 0° C. and pH was adjusted to 11 by adding K$_2$CO$_3$. The reaction mixture was extracted with ethyl acetate three times. The combined organic layer was dried over MgSO$_4$, filtered and evaporated to give the oil (5 g), which was a mixture of the desired aminonitrile, cyanohydrin and starting ketone. The crude mixture was used in next step without further purification. $^1$H NMR (400 MHz, CDCl$_3$) δ 7.36–7.25 (m, 5H), 2.77–2.74 (m, 2H), 2.48–2.31 (m, 4H), 2.13–2.08 (m, 2H), 1.81–1.74 (m, 2H).

Step 2. 4-Aminomethyl-1-benzyl-piperidin-4-ylamine: To a cold (0° C.) suspension of lithium aluminium hydride (598 mg, 15.8 mmol) in THF (20 mL) was added a solution of 4-amino-1-benzyl-piperidine-4-carbonitrile (1.1 g, 5.2 mmol) in THF (40 mL) dropwise at 0° C. and warmed to room temperature slowly. The reaction mixture was refluxed overnight and cooled to 0° C., followed by quenching with water (0.6 mL), 15% NaOH (0.6 mL) and water (1.8 mL). The mixture was stirred for 3 h at room temperature and filtered through a pad of celite. The filtrate was evaporated to give 1 g of the desired diamine that was used without further purification. $^1$H NMR (400 MHz, CD$_3$OD) δ 7.34–7.24 (m, 5H), 3.54 (s, 2H), 2.87–2.75 (m, 2H), 2.63–2.59 (m, 2H), 2.45–2.38 (m, 2H), 2.15–2.02 (m, 2H), 1.85–1.77 (m, 2H).

Step 3. Spiro[N-benzyl-piperidine-3,4-piperazinorifamycin S]: To a solution of 4-Aminomethyl-1-benzyl-piperidin-4-ylamine (285 mg, 1.3 mmol) in dioxane/H$_2$O (4/1) (2 mL) were added K$_3$Fe(CN)$_6$ (128 mg, 0.39 mmol) and 3-bromorifamycin S (100 mg, 0.13 mmol) and the reaction mixture was stirred overnight at room temperature. The reaction mixture was cooled to 0° C. and quenched with saturated NH$_4$Cl. The mixture was diluted with ethyl acetate and washed with saturated NH$_4$Cl and saturated brine. The organic layer was dried over Na$_2$SO$_4$, filtered and evaporated. The residue was purified with preparative thin layer chromatography (methylene chloride:methanol:AcOH=100: 5:0.2) to give the desired product (2.2 mg, 2%) as a dark red solid. ESI MS m/z 895 (M+H$^+$); $^1$H NMR (400 MHz, CDCl$_3$) δ 13.83 (s, 1H), 8.22 (s, 1H), 7.47–7.29 (m, 5H), 7.36 (s, 1H), 6.45 (dd, J=14.8 Hz and 10.0 Hz, 1H), 6.26 (d, J=10.8 Hz, 1H), 6.12 (dd, J=16.4 Hz and 5.6 Hz, 1H), 6.01 (d, J=12.4 Hz, 1H), 5.07 (dd, J=5.6 Hz and 12.4 Hz, 1H), 4.98 (d, J=10.0 Hz, 1H), 4.02–3.41 (m, 8H), 3.09–3.02 (m, 1H), 3.07 (s, 3H), 2.73–2.16 (m, 5H), 2.26 (s, 3H), 2.09 (s, 3H), 2.03 (s, 3H), 1.83–1.58 (m, 7H), 1.70 (s, 3H), 1.04 (d, J=6.8 Hz, 3H), 0.85 (d, J=7.2 Hz, 3H), 0.65 (d, J=6.8 Hz, 3H), 0.01 (d, J=7.2 Hz, 3H).

EXAMPLE 13

Spiro[N-(2,2,2-trichloro-1,1-dimethyl-ethoxycarbonyl)-piperidine-3,4-piperazinorifamycin S]

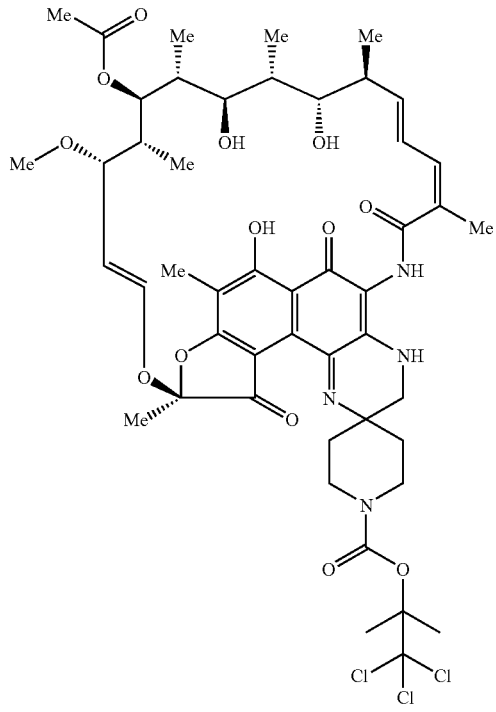

Synthesis: Step 1. 4-(2,2,2-Trifluoro-acetylamino)-4-[(2,2,2-trifluoro-acetylamino)-methyl]-piperidine-1-carboxylic acid 2,2,2-trichloro-1,1-dimethyl-ethyl ester: To a cold (0° C.) solution of 4-(2,2,2-trifluoro-acetylamino)-4-[(2,2,2-trifluoro-acetylamino)-methyl]-piperidinium chloride (500 mg, 1.4 mmol) in pyridine (5 mL) was added 2,2,2-trichloro-1,1-dimethylethyl chloroformate (504 mg, 2.1 mmol) and warmed to room temperature over 1 h and the reaction mixture was stirred overnight at room temperature. The reaction mixture was diluted with ethyl acetate and washed with 1 N HCl solution five times and washed with saturated brine. The organic layer was dried over MgSO$_4$, filtered and evaporated to give the desired product (450 mg, 61%) that was used without further purification. $^1$H NMR (400 MHz, CDCl$_3$) δ 8.46 (br s, 1H), 7.49 (br t, J=5.2 Hz, 1H), 3.81–3.51 (m, 6H), 1.97–1.69 (m, 4H), 1.95 (s, 3H), 1.93 (s, 3H).

Step 2. 4-Amino-4-aminomethyl-piperidine-1-carboxylic acid 2,2,2-trichloro-1,1-dimethyl-ethyl ester: A solution of 4-(2,2,2-trifluoro-acetylamino)-4-[(2,2,2-trifluoro-acetylamino)-methyl]-piperidine-1-carboxylic acid 2,2,2-trichloro-1,1-dimethyl-ethyl ester (450 mg, 0.86 mmol) in 10% K$_2$CO$_3$ in MeOH/H$_2$O (5/2) (7 mL) was refluxed overnight. The reaction mixture was cooled to room temperature and evaporated. The residue was dissolved in water and extracted with chloroform. The organic layer was dried over MgSO$_4$, filtered and evaporated to give 287 mg of the desired diamine that was used without further purification. $^1$H NMR (400 MHz, CD$_3$OD) δ 3.75–3.61 (m, 2H), 3.48–3.34 (m, 2H), 3.29 (s, 2H), 1.899 (s, 3H), 1.895 (s, 3H), 1.62–1.48 (m, 2H), 1.44–1.34 (m, 2H).

Step 3. Spiro[N-(2,2,2-trichloro-1,1-dimethyl-ethoxycarbonyl)-piperidine-3,4-piperazinorifamycin S]: To a solution of crude 4-amino-4-aminomethyl-piperidine-1-carboxylic acid 2,2,2-trichloro-1,1-dimethyl-ethyl ester (287 mg, 0.86 mmol) in dioxane/H$_2$O (4/1) (1 mL) were added K$_3$Fe(CN)$_6$ (66 mg, 0.2 mol) and 3-bromorifamycin S (100 mg, 0.13 mmol) and the reaction mixture was stirred overnight at room temperature. The reaction mixture was cooled to 0° C. and quenched with 0.5 N HCl. The mixture was diluted with ethyl acetate and washed with 0.5 N HCl and saturated brine. The organic layer was dried over Na$_2$SO$_4$, filtered and evaporated. The residue was purified with preparative thin layer chromatography (hexanes:ethyl acetate=1:1+0.2% AcOH) to give the desired product (63 mg, 48%) as a dark red solid. ESI MS m/z 1007 (M+H$^+$); $^1$H NMR (400 MHz, CDCl$_3$) δ 13.82 (s, 1H), 8.19 (s, 1H), 7.14 (br s, 1H), 6.43–6.36 (m, 1H), 6.23 (d, J=10.8 Hz, 1H), 6.09 (dd, J=16.4 Hz and 7.2 Hz, 1H), 6.00 (d, J=12.4 Hz, 1H), 5.05–5.02 (m, 1H), 4.97 (d, J=10.4 Hz, 1H), 4.04–3.72 (m, 6H), 3.38 (br s, 1H), 3.29 (dd, J=13.2 Hz and 6.0 Hz, 1H), 3.04 (s, 3H), 3.04–3.00 (m, 1H), 2.39–2.30 (m, 1H), 2.22 (s, 3H), 2.051 (s, 3H), 2.049 (s, 3H), 2.02 (s, 3H), 2.01 (s, 3H), 1.91–1.79 (m, 6H), 1.77–1.60 (m, 3H), 1.70 (s, 3H), 1.01 (d, J=7.2 Hz, 3H), 0.82 (d, J=6.4 Hz, 3H), 0.63 (d, J=7.2 Hz, 3H), 0.01 (d, J=7.2 Hz, 3H).

EXAMPLE 14

Spiro[N-alloc-piperidine-3,4-piperazinorifamycin S]

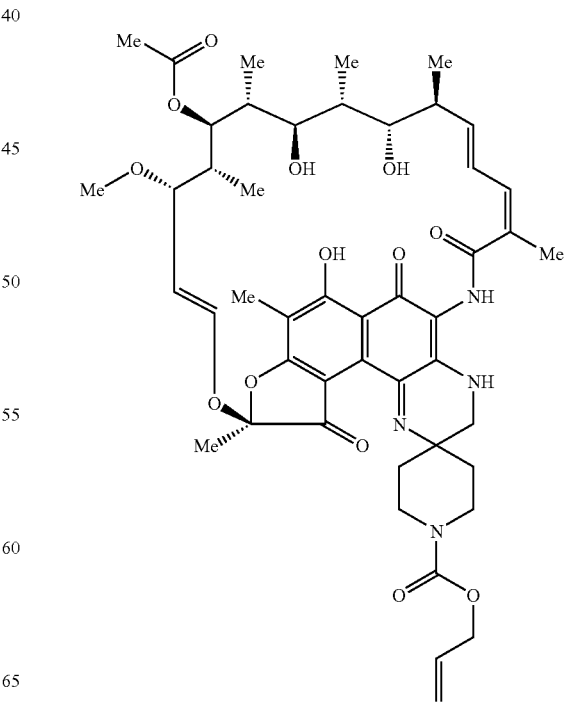

Synthesis: Step 1. 4-(2,2,2-Trifluoro-acetylamino)-4-[(2,2,2-trifluoro-acetylamino)-methyl]-piperidine-1-carboxylic acid allyl ester: To a cold (0° C.) solution of 4-(2,2,2-trifluoro-acetylamino)-4-[(2,2,2-trifluoro-acetylamino)-methyl]-piperidinium chloride (500 mg, 1.4 mmol) in pyridine (5 mL) was added allyl chloroformate (0.3 mL, 2.8 mmol) and warmed to room temperature over 1 h and the reaction mixture was stirred overnight at room temperature. The reaction mixture was diluted with ethyl acetate and washed with 1 N HCl solution five times and washed with saturated brine. The organic layer was dried over MgSO$_4$, filtered and evaporated to give the desired product (270 mg, 48%) that was used without further purification. $^1$H NMR (400 MHz, CDCl$_3$) δ 7.72 (br s, 1H), 6.71 (br s, 1H), 5.95–5.85 (m, 1H), 5.27 (d, J=17.2 Hz, 1H), 5.21 (d, J=11.6 Hz, 1H), 4.56 (d, J=5.6 Hz, 2H), 3.83–3.69 (m, 4H), 3.20–3.18 (m, 2H), 2.18–2.12 (m, 2H), 1.72–1.66 (m, 2H).

Step 2. 4-Amino-4-aminomethyl-piperidine-1-carboxylic acid allyl ester: A solution of 4-(2,2,2-trifluoro-acetylamino)-4-[(2,2,2-trifluoro-acetylamino)-methyl]-piperidine-1-carboxylic acid allyl ester (270 mg, 0.67 mmol) in 10% K$_2$CO$_3$ in MeOH/H$_2$O (5/2) (7 mL) was refluxed overnight. The reaction mixture was cooled to room temperature and evaporated. The residue was dissolved in water and extracted with chloroform. The organic layer was dried over MgSO$_4$, filtered and evaporated to give 112 mg (79%) of the desired diamine that was used without further purification. $^1$H NMR MHz, CD$_3$OD) 5.99–5.90 (m, 1H), 5.29 (d, J=17.2 Hz, 1H), 5.19 (d, J=10.0 Hz, 1H), 4.56 (d, J=5.2 Hz, 2H), 3.67–3.32 (m, 6H), 1.72–1.38 (m, 4H).

Step 3. Spiro[N-alloc-piperidine-3,4-piperazinorifamycin S]: To a solution of 4-Amino-4-aminomethyl-piperidine-1-carboxylic acid allyl ester (112 mg) in dioxane/H$_2$O (4/1) (1 mL) were added K$_3$Fe(CN)$_6$ (66 mg, 0.2 mol) and 3-bromorifamycin S (100 mg, 0.13 mmol) and the reaction mixture was stirred overnight at room temperature. The reaction mixture was cooled to 0° C. and quenched with 0.5 N HCl. The mixture was diluted with ethyl acetate and washed with 0.5 N HCl and saturated brine. The organic layer was dried over Na$_2$SO$_4$, filtered and evaporated. The residue was purified with preparative thin layer chromatography (hexanes:ethyl acetate=1:1+0.2% AcOH) to give the desired product (44 mg, 38%) as a dark red solid. ESI MS m/z 889 (M+H$^+$); $^1$H NMR (400 MHz, CDCl$_3$) δ 13.80 (br s, 1H), 8.18 (s, 1H), 7.18 (br s, 1H), 6.40 (dd, J=16.0 Hz and 11.2 Hz, 1H), 6.23 (d, J=10.4 Hz, 1H), 6.10 (dd, J=15.6 Hz and 6.4 Hz, 1H), 6.01 (d, J=12.4 Hz, 1H), 5.91 (br s, 1H), 5.28 (br s, 1H), 5.17 (br d, J=9.6 Hz, 1H), 5.05 (dd, J=12.4 Hz and 6.4 Hz, 1H), 4.96 (d, J=10.8 Hz, 1H), 4.56 (d, J=5.2 Hz, 2H), 4.04–3.74 (m, 6H), 3.59 (br s, 1H), 3.37 (d, J=4.4 Hz, 1H), 3.27 (dd, J=13.2 Hz and 6.0 Hz, 1H), 3.06–3.02 (m, 2H), 3.04 (s, 3H), 2.39–2.33 (m, 1H), 2.23 (s, 3H), 2.05 (s, 3H), 2.01 (s, 3H), 1.86–1.58 (m, 7H), 1.70 (s, 3H), 1.01 (d, J=7.2 Hz, 3H), 0.82 (d, J=6.8 Hz, 3H), 0.63 (d, J=6.8 Hz, 3H), 0.01 (d, J=7.2 Hz, 3H).

EXAMPLE 15

Spiro[piperidine-3,4-piperazinorifamycin S]

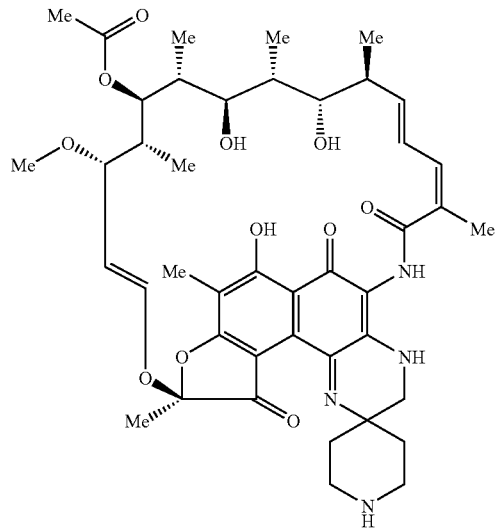

Synthesis: Step 1.4Cyano-4-(2-trimethylsilanyl-ethoxycarbonylamino)-piperidine-1-carboxylic acid tert-butyl ester: To a solution of 4-amino-4-cyano-piperidine-1-carboxylic acid tert-butyl ester (200 mg, 0.9 mmol) in DMF (2 mL) was added 1-[2-(trimethylsilyl)ethoxycarbonyloxy]pyrrolidin-2,5-dione (246 mg, 1.0 mmol) and the reaction mixture was stirred overnight at room temperature. The reaction mixture was diluted with ethyl acetate and washed with 1N HCl solution and saturated brine. The organic layer was dried over MgSO$_4$, filtered and evaporated. The resulting residue was purified by silica gel column chromatography (n-hexanes:ethyl acetate=4:1) to give the desired product (210 mg, 64%). $^1$H NMR (400 MHz, CDCl$_3$) δ 4.99 (br s, 1H), 4.22–4.18 (m, 2H), 3.93 (br d, J=12.0 Hz, 2H), 3.27–3.20 (m, 2H), 2.35 (br d, J=12.8 Hz, 2H), 1.79–1.69 (m, 2H), 1.45 (s, 9H), 1.02–0.98 (m, 2H), 0.03 (s, 9H).

Step 2. 4-Aminomethyl-4-(2-trimethylsilanyl-ethoxycarbonylamino)-piperidine-1-carboxylic acid tert-butyl ester: To a solution of 4-cyano-4-(2-trimethylsilanyl-ethoxycarbonylamino)-piperidine-1-carboxylic acid tert-butyl ester (190 mg, 0.5 mmol) in ethanol (5 mL) was added Raney nickel (100 mg) and the reaction mixture was stirred overnight under balloon of hydrogen at room temperature. The reaction mixture was filtered through celite and evaporated to give the desired amine (170 mg, 89%) that was used without further purification. $^1$H NMR (400 MHz, CD$_3$OD) δ 4.13–4.09 (m, 2H), 3.84–3.80 (m, 2H), 3.03 (br s, 2H), 2.84 (s, 2H), 2.07 (d, J=14.0 Hz, 2H), 1.45 (s, 9H), 1.42–1.37 (m, 2H), 1.02–0.96 (m, 2H), 0.06 (s, 9H).

Step 3. [N-Boc-4-(2-trimethylsilanyl-ethoxycarbonylamino)-piperidine-4-ylmethyl]-amino-rifamycin: To a solution of 4-aminomethyl-4-(2-trimethylsilanyl-ethoxycarbonylamino)-piperidine-1-carboxylic acid tert-butyl ester (170 mg, 0.45 mmol) in THF (3 mL) was added 3-bromorifamycin S (250 mg, 0.32 mmol) and triethylamine (0.12 mL, 0.86 mmol) and the reaction mixture was stirred for 4 h at room temperature. The reaction mixture was cooled to 0° C. and quenched with 0.5 N HCl. The mixture was diluted with ethyl acetate and washed with 0.5 N HCl and saturated brine. The organic layer was dried over Na$_2$SO$_4$, filtered and evaporated. The residue was purified with silica gel column chromatography (hexanes:ethyl acetate=1:2) to give the desired product (220 mg, 65%) as a purple solid. $^1$H NMR (400 MHz, CDCl₃) δ 13.70 (s, 1H), 7.52 (s, 1H), 6.88 (br s, 1H), 6.56 (br s, 1H), 6.31 (d, J=11.2 Hz, 1H), 6.13 (dd, J=16.0 Hz and 6.4 Hz, 1H), 6.08 (dd, J=12.4 Hz and 1.2 Hz, 1H), 5.14 (dd, J=12.0 Hz and 5.6 Hz, 1H), 5.02 (d, J=10.0 Hz, 1H), 4.49 (s, 1H), 4.06–3.97 (m, 2H), 3.89–3.80 (m, 6H), 3.62 (br s, 1H), 3.46–3.45 (m, 1H), 3.12–2.96 (m, 3H), 3.09 (s, 3H), 2.38–2.23 (m, 1H), 2.29 (s, 3H), 2.12–1.88 (m, 1H), 2.10 (s, 3H), 2.06 (s, 3H), 1.83–1.49 (m, 6H), 1.74 (s, 3H), 1.44 (s, 9H), 1.04 (d, J=6.8 Hz, 3H), 0.90–0.84 (m, 2H), 0.87 (d, J=7.2 Hz, 3H), 0.68 (d, =6.8 Hz, 3H), 0.08 (d, J=7.2 Hz, 3H), 0.02 (s, 9H).

Step 4. Spiro[piperidine-3,4-piperazinorifamycin S]: To a solution of [N-Boc-4-(2-trimethylsilanyl-ethoxycarbonylamino)-piperidine-4-ylmethyl]-amino-rifamycin (10 mg, 0.01 mmol) in nitromethane (1 mL) was added ZnBr₂ (10 mg, 0.04 mmol) and the reaction mixture was stirred for 3 d at room temperature. The reaction mixture was diluted with ethyl acetate and washed with 5% Na₂HPO₄ and saturated brine. The organic layer was dried over Na₂SO₄, filtered and evaporated. The residue was purified with preparative thin layer chromatography (methylene chloride:methanol:AcOH=120:30:0.3) to give the desired product (1 mg, 14%) as a dark red solid. ESI MS m/z 895 (M+H⁺); ¹H NMR (400 MHz, CDCl₃) δ 13.70 (s, 1H), 9.47 (br s, 1H), 8.18 (s, 1H), 7.13 (s, 1H), 6.46 (dd, J=15.6 Hz and 10.8 Hz, 1H), 6.26 (d, J=11.2 Hz, 1H), 6.13 (dd, J=16.0 Hz and 6.8 Hz, 1H), 5.98 (d, J=12.0 Hz, 1H), 5.02 (dd, J=12.0 Hz and 8.0 Hz, 1H), 4.99 (d, J=11.6 Hz, 1H), 3.96 (br s, 1H), 3.77 (d, J=8.8 Hz, 1H), 3.54 (br s, 1H), 3.39–3.30 (m, 3H), 3.05 (s, 3H), 3.05–3.01 (m, 2H), 2.35 (m, 1H), 2.25 (s, 3H), 2.18–1.59 (m, 10H), 2.07 (s, 3H), 2.02 (s, 3H), 1.75 (s, 3H), 1.02 (d, J=6.8 Hz, 3H), 0.84 (d, J=6.4 Hz, 3H), 0.65 (d, J=6.8 Hz, 3H), 0.01 (d, J=7.2 Hz, 3H).

EXAMPLE 16

Spiro[N-benzyl-pyrrolidine-3,4-piperazinorifamycin S]

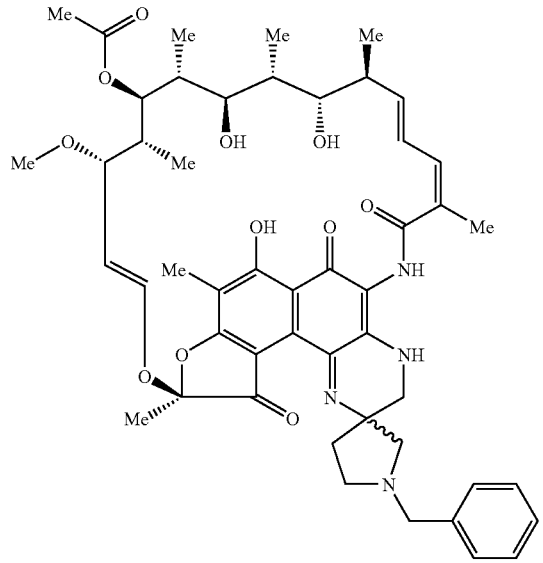

Step 1. 3-Oxo-pyrrolidine-1-carboxylic acid tert-butyl ester: To a cold (−78° C.) solution of oxalyl chloride (2.8 mL, 32.4 mmol) in CH₂Cl₂ (20 mL) was added DMSO (4.6 mL, 64.8 mmol) in CH₂Cl₂ (40 mL) and stirred for 5 min at −78° C., followed by the addition of N-Boc-3-pyrrolidinol (4.04 g, 21.6 mmol) in CH₂Cl₂ (60 mL) and the reaction mixture was stirred for 2 h at −78° C. Triethylamine (15 mL, 108 mmol) was added to the reaction mixture and stirred for 1 h at −78° C. The reaction mixture was warmed to room temperature and stirred for 2 h at room temperature. It was cooled to 0° C. and quenched with saturated NaHCO₃ and diluted with ethyl acetate. The organic layer was washed with saturated NaHCO₃ and saturated brine. The combined organic layer was dried over MgSO₄, filtered and evaporated to give the desired product (4 g, 100%) that was used without further purification. ¹H NMR (400 MHz, CDCl₃) δ 3.79–3.75 (m, 4H), 2.58 (t, J=8.0 Hz, 2H), 1.47 (s, 9H).

Step 2. 3-Amino-3-cyano-pyrrolidine-1-carboxylic acid tert-butyl ester: To a mixture of 3-oxo-pyrrolidine-1-carboxylic acid tert-butyl ester (1 g, 5.34 mmol), ammonium chloride (316 mg, 5.9 mmol) and sodium cyanide (289 mg, 5.9 mmol) was added 2 M NH₃ in MOH (20 mL) and refluxed for 3 h and cooled to room temperature. Another 2M NH₃ in MeOH (20 mL) was added and refluxed for 3 h again. The reaction mixture was cooled to room temperature and methanol was removed under reduced pressure. The residue was dissolved in ethyl acetate and washed with water and saturated brine. The organic layer was dried over MgSO₄, filtered and evaporated to give 1.1 g in 1:1 mixture of the desired product and cyanohydrin. The crude mixture was used without further purification.

Step 3. 3–Cyano-3-(2,2,2-trifluoro-acetylamino)-pyrrolidine-1-carboxylic acid tert-butyl ester: To a cold (0° C.) solution of 3-amino-3-cyano-pyrrolidine-1-carboxylic acid tert-butyl ester (4.4 g, 20.7 mmol) in pyridine (40 mL) was added trifluoroacetic anhydride (4.3 mL, 31 mmol) and warmed to room temperature over 2 h and the reaction mixture was stirred overnight. The reaction mixture was diluted with ethyl acetate and washed with 1 N HCl five times and washed with saturated brine. The organic layer was dried over MgSO₄, filered and evaporated to give the desired product (5.7 g, 89%) that was used without further purification.

Step 4. 3-Aminomethyl-3-(2,2,2-trifluoro-acetylamino)-pyrrolidine-1-carboxylic acid tert-butyl ester: To a solution of 3-cyano-3-(2,2,2-trifluoro-acetylamino)-pyrrolidine-1-carboxylic acid tert-butyl ester (2.7 g, 8.8 mmol) in ethanol (20 mL) was added Raney nickel (1.5 g) and the reaction mixture was stirred overnight under balloon of hydrogen at room temperature. The reaction mixture was filtered through celite and evaporated to give 2.7 g of the desired amine that was used without further purification.

Step 5. 3-(2,2,-Trifluoro-acetylamino)-3-[(2,2,2-trifluoro-acetylamino)-methyl]-pyrrolidine-1-carboxylic acid tert-butyl ester: To a cold (0° C.) solution of 4-aminomethyl-4-(2,2,2-trifluoro-acetylamino)-piperidine-1-carboxylic acid tert-butyl ester (2.7 g, 8.8 mmol) in pyridine (20 mL) was added trifluoroacetic anhydride (1.8 mL, 13.2 mmol) and warmed to room temperature over 2 h and stirred overnight. The reaction mixture was diluted with ethyl acetate and washed with 1 N HCl five times and washed with saturated brine. The organic layer was dried over MgSO₄, filtered and evaporated to give the desired product (3 g, 83%) that was used without further purification.

Step 6. 3-(2,2,2-Trifluoro-acetylamino)-3-[(2,2,2-trifluoro-acetylamino)-methyl]-pyrrolidinium chloride: To a solution of 3-(2,2,2-trifluoro-acetylamino)-3-[(2,2,2-trifluoro-acetylamino)-methyl]-pyrrolidine-1-carboxylic acid tert-butyl ester (3 g, 7.4 mmol) in ethyl acetate (20 mL) was added 2 N HCl in Et₂O (20 mL, 40 mmol) and the reaction mixture was stirred overnight at room temperature. The reaction mixture was filtered and washed with ether to give the desired product (1.6 g, 64%) as a white solid that was used without further purification.

Step 7. N-{1-Benzyl-3-[(2,2,2-trifluoro-acetylamino)-methyl]-pyrrolidin-3-yl}-2,2,2-trifluoro-acetamide: To a cold (0° C.) solution of 3-(2,2,2-trifluoro-acetylamino)-3-[(2,2,2-trifluoro-acetylamino)-methyl]-pyrrolidinium chloride (497 mg, 1.45 mmol) in methanol (4 mL) was added benzaldehyde (0.14 mL, 1.45 mmol) and NaOAc (357 mg, 4.35 mmol) and the mixture was stirred for 5 min, followed by the addition of AcOH (0.08 mL, 1.45 mmol) and NaCNBH$_3$ (109 mg, 1.74 mmol) and the reaction mixture was stirred for 4 h at 0° C. The methanol was removed under reduced pressure and the residue was diluted with ethyl acetate and washed with water and saturated NaHCO$_3$. The organic layer was dried over MgSO$_4$, filtered and evaporated to give 460 mg of the desired product that was used without further purification.

Step 8. 3-Aminomethyl-1-benzyl-pyrrolidin-3-ylamine: The solution of N-{1-benzyl-3-[(2,2,2-trifluoro-acetylamino)-methyl]-pyrrolidin-3-yl}-2,2,2-trifluoro-acetamide (460 mg, 1.2 mmol) in 7 N NH$_3$ in MeOH (13 mL) was refluxed overnight in a sealed tube. The reaction mixture was cooled to room temperature and evaporated to give 470 mg of the desired diamine that was used without further purification.

Step 9. Spiro[N-benzyl-pyrrolidine-3,4-piperazinorifamycin S]: To a solution of crude 3-aminomethyl-1-benzyl-pyrrolidin-3-ylamine (470 mg) in dioxane/H$_2$O (4/1) (2 mL) were added K$_3$Fe(CN)$_6$ (63 mg, 0.19 mmol) and 3-bromorifamycin S (150 mg, 0.19 mmol) and the reaction mixture was stirred overnight at room temperature. The reaction mixture was cooled to 0° C. and quenched with saturated NH$_4$Cl. The mixture was diluted with ethyl acetate and washed with saturated NH$_4$Cl and saturated brine. The organic layer was dried over Na$_2$SO$_4$, filtered and evaporated. The residue was purified with preparative thin layer chromatography (methylene chloride:methanol:AcOH=175:7:0.4) to give the desired product (2.2 mg, 1.3%) as a dark red solid in diasteromeric mixture. ESI MS m/z 881 (M+H$^+$); $^1$H NMR (400 MHz, CDCl$_3$) δ 13.79 (s, 1H), 8.18 (s, 1H), 7.36–7.27 (m, 6H), 6.47 (dd, J=10.8 Hz and 16.0 Hz, 1H), 6.27 (d, J=10.4 Hz, 1H), 6.12 (dd, J=15.6 Hz and 6.4 Hz, 1H), 6.04 (d, J=12.4 Hz, 1H), 5.11 (dd, J=12.8 Hz and 6.4 Hz, 1H), 4.99 (d, J=10.0 Hz, 1H), 3.86 (br s, 2H), 3.79 (br d, J=10.0 Hz, 2H), 3.40–3.39 (m, 2H), 3.21–3.15 (m, 2H), 3.07 (s, 3H), 3.07–3.03 (m, 1H), 2.86–2.36 (m, 4H), 2.27 (s, 3H), 2.22–2.01 (m, 2H), 2.10 (s, 3H), 2.05 (s, 3H), 1.81–1.62 (m, 4H), 1.75 (s, 3H), 1.05 (d, J=6.8 Hz, 3H), 0.86 (d, J=7.2 Hz, 3H), 0.67 (d, J=6.8 Hz, 3H), 0.03 (d, J=6.8 Hz, 3H).

EXAMPLE 17

Spiro[N-methyl-pyrrolidine-3,4-piperazinorifamycin S]

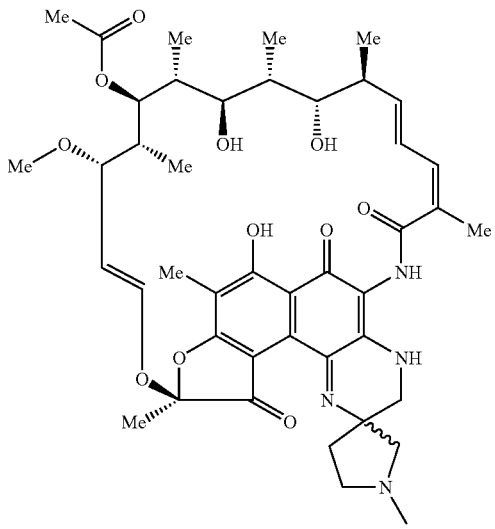

Synthesis: Step 1. 3-Cyano-3-(2,2,2-trifluoro-acetylamino)-pyrrolidinium chloride: To a solution of 3-cyano-3-(2,2,2-trifluoro-acetylamino)-pyrrolidine-1-carboxylic acid tert-butyl ester (3 g, 9.8 mmol) in ethyl acetate (20 mL) was added 2 N HCl in Et$_2$O (20 mL, 40 mmol) and the reaction mixture was stirred overnight at room temperature. The reaction mixture was filtered and washed with ether to give the desired product (2.27 g, 95%) as a white solid that was used without further purification.

Step 2. N-(3-Cyano-1-methyl-pyrrolidin-3-yl)-2,2,2-trifluoro-acetamide: To a cold (0° C.) solution of 3-cyano-3-(2,2,2-trifluoro-acetylamino)-pyrrolidinium chloride (582 mg, 2.4 mmol) in methanol (5 mL) was added formaldehyde (0.18 mL, 2.4 mmol) and NaOAc (590 mg, 7.2 mmol) and the mixture was stirred for 5 min, followed by the addition of AcOH (0.14 mL, 2.4 mmol) and NaCNBH$_3$ (181 mg, 2.9 mmol) and the reaction mixture was stirred for 4 h at 0° C. The methanol was removed under reduced pressure and the residue was diluted with ethyl acetate and washed with water and saturated NaHCO$_3$. The organic layer was dried over MgSO$_4$, filtered and evaporated to give 400 mg of the desired product that was used without further purification.

Step 3. N-(3-Aminomethyl-1-methyl-pyrrolidin-3-yl)-2,2,2-trifluoro-acetamide: To a solution of N-(3-cyano-1-methyl-pyrrolidin-3-yl)-2,2,2-trifluoro-acetamide (400 mg, 1.8 mmol) in ethanol (10 mL) was added Raney nickel (1 g) and the reaction mixture was stirred overnight under balloon of hydrogen at room temperature. The reaction mixture was filtered through celite and evaporated to give 400 mg of the desired amine that was used without further purification.

Step 4. 3-Aminomethyl-1-methyl-pyrrolidin-3-ylamine: The solution of N-(3-aminomethyl-1-methyl-pyrrolidin-3-yl)-2,2,2-trifluoro-acetamide (400 mg, 1.8 mmol) in 7 N NH$_3$ in MeOH (13 mL) was refluxed overnight in a sealed tube. The reaction mixture was cooled to room temperature and evaporated to give 405 mg of the desired diamine that was used without further purification.

Step 5. Spiro[N-methyl-pyrrolidine-3,4-piperazinorifamycin S]: To a solution of crude 3-aminomethyl-1-methyl-pyrrolidin-3-ylamine (240 mg, 1.85 mmol) in dioxane/H$_2$O (4/1) (2.5 mL) were added K$_3$Fe(CN)$_6$ (63 mg, 0.19 mmol) and 3-bromorifamycin S (150 mg, 0.19 mmol) and the reaction mixture was stirred overnight at room temperature. The reaction mixture was cooled to 0° C. and quenched with saturated NH$_4$Cl. The mixture was diluted with ethyl acetate and washed with saturated NH$_4$Cl and saturated brine. The organic layer was dried over Na$_2$SO$_4$, filtered and evaporated. The residue was purified with preparative thin layer chromatography (methylene chloride:methanol:AcOH=150:10:0.3) to give the desired product (1.3 mg, 0.8%) as a dark brown solid in 1:1 diasteromeric mixture. ESI MS m/z 805 (M+H$^+$); $^1$H NMR (400 MHz, CDCl$_3$) δ 13.72 (s, 1/2H), 13.67 (s, 1/2H), 8.25 (s, 1/2H), 8.23 (s, 1/2H), 7.28 (s, 1/2H), 7.24 (s, 1/2H), 6.50–644 (1H), 6.28 (d, J=10.8 Hz, 1H), 6.13 (dd, J=16.0 Hz and 7.2 Hz, 1/2H), 6.03 (d, J=10.8 Hz, 1/2H), 5.10 (dd, J=5.8 Hz and 12.4 Hz, 1/2H), 5.09 (dd, J=5.8 Hz and 12.4 Hz, 1/2H), 5.00 (d, J=10.8 Hz, 1H), 3.89–3.64 (m, 5H), 3.42–3.41 (m, 1H), 3.28 (d, J=11.6 Hz, 1/2H), 3.22 (d, J=11.6 Hz, 1/2H), 3.08 (s, 3/2H), 3.076 (s, 3/2H), 3.09–3.04 (m, 2H), 2.92 (br s, 1H), 2.71 (br s, 1H), 2.38 (m, 1H), 2.27 (s, 3/2H), 2.26 (s, 3/2H), 2.10–1.63 (m, 6H), 2.052 (s, 3H), 2.050 (s, 3H), 2.046 (s, 3H), 1.74 (s, 3/2H), 1.73 (s, 3/2H), 1.05 (d, J=7.2 Hz, 3H), 0.87 (d, J=7.2 Hz, 3H), 0.68 (d, J=6.8 Hz, 3/2H), 0.67 (d, J=6.8 Hz, 3/2H), 0.03 (d, J=6.8 Hz, 3H).

EXAMPLE 18

Spiro[N-isobutyl-pyrrolidine-3,4-piperazinorifamycin S]

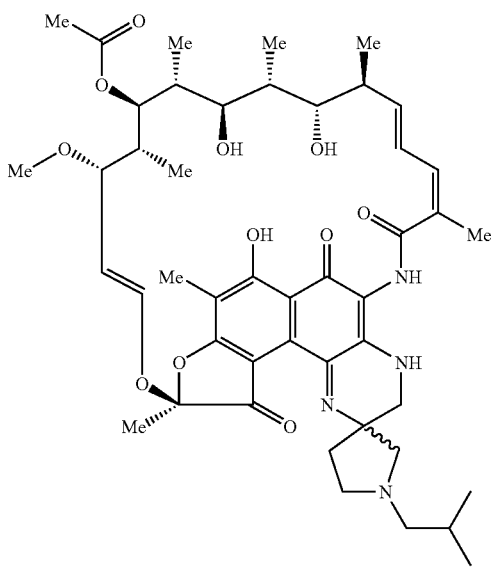

Synthesis: Step 1. N-(3–Cyano-1-isobutyl-pyrrolidin-3-yl)-2,2,2-trifluoro-acetamide: To a solution of 3-cyano-3-(2,2,2-trifluoro-acetylamino)-pyrrolidinium chloride (920 mg, 3.8 mmol) in DMF (7 mL) was added $K_2CO_3$ (2.6 g, 19 mmol) and isobutyl bromide (0.84 mL, 4.56 mmol) and the reaction mixture was stirred for 2 d at 60° C. The reaction mixture was cooled to room temperature and diluted with ethyl acetate and washed with saturated brine. The organic layer was dried over $MgSO_4$, filtered and evaporated to give 900 mg of the desired product that was used without further purification.

Step 2. N-(3-Aminomethyl-1-isobutyl-pyrrolidin-3-yl)-2,2,2-trifluoro-acetamide: To a solution of N-(3-cyano-1-methyl-pyrrolidin-3-yl)-2,2,2-trifluoro-acetamide (900 mg, 3.4 mmol) in ethanol (10 mL) was added Raney nickel (1.5 g) and the reaction mixture was stirred overnight under balloon of hydrogen at room temperature. The reaction mixture was filtered through celite and evaporated to give 890 mg of the desired amine that was used without further purification.

Step 3. 3-Aminomethyl-1-isobutyl-pyrrolidin-3-ylamine: The solution of N-(3-aminomethyl-1-isobutyl-pyrrolidin-3-yl)-2,2,2-trifluoro-acetamide (890 mg, 3.3 mmol) in 7 N $NH_3$ in MeOH (20 mL) was refluxed overnight in a sealed tube. The reaction mixture was cooled to room temperature and evaporated to give 900 mg of the desired diamine that was used without further purification.

Step 4. Spiro[N-isobutyl-pyrrolidine-3,4-piperazinorifamycin S]: To a solution of crude 3-aminomethyl-1-isobutyl-pyrrolidin-3-ylamine (400 mg, 2.3 mmmol) in dioxane/$H_2O$ (4/1) (3 mL) were added $K_3Fe(CN)_6$ (63 mg, 0.19 mmol) and 3-bromorifamycin S (150 mg, 0.19 mmol) and the reaction mixture was stirred overnight at room temperature. The reaction mixture was cooled to 0° C. and quenched with saturated $NH_4Cl$. The mixture was diluted with ethyl acetate and washed with saturated $NH_4Cl$ and saturated brine. The organic layer was dried over $Na_2SO_4$, filtered and evaporated. The residue was purified with preparative thin layer chromatography (methylene chloride:methanol:AcOH=200:10:0.4) to give the desired product (1.5 mg, 0.9%) as a dark brown solid in diasteromeric mixture. ESI MS m/z 847 (M+H$^+$); $^1$H NMR (400 MHz, CDCl$_3$) δ 13.73 (s, 1H), 8.14 (s, 1H), 7.31 (br s, 1H), 6.44 (dd, J=10.8 Hz and 16.0 Hz, 1H), 6.25 (d, J=10.4 Hz, 1H), 6.10 (dd, J=16.0 Hz and 6.4 Hz, 1H), 6.01 (dd, J=12.8 Hz and 0.8 Hz, 1H), 5.09 (dd, J=6.0 Hz and 12.4 Hz, 1H), 4.97 (d, J=9.6 Hz, 1H), 3.83 (d, J=5.6 Hz, 2H), 3.76 (d, J=10.0 Hz, 2H), 3.56 (br s, 2H), 3.39 (br d, J=6.0 Hz, 2H), 3.20 (br d, J=12.0 Hz, 2H), 3.05 (s, 3H), 3.05–3.00 (m, 1H), 2.82 (m, 2H), 2.40–2.34 (m, 1H), 2.25 (s, 3H), 2.07 (s, 3H), 2.06–1.62 (m, 6H), 2.03 (d, J=3.6 Hz, 6H), 2.02 (s, 3H), 1.71 (s, 3H), 1.03 (d, J=6.8 Hz, 3H), 1.03–1.02 (m, 1H), 0.85 (d, J=7.2 Hz, 3H), 0.65 (d, J=7.2 Hz, 3H), 0.01 (d, J=7.2 Hz, 3H).

EXAMPLE 19

Spiro[N-(quinolin-3-ylmethyl)-pyrrolidine-3,4-piperazinorifamycin S]

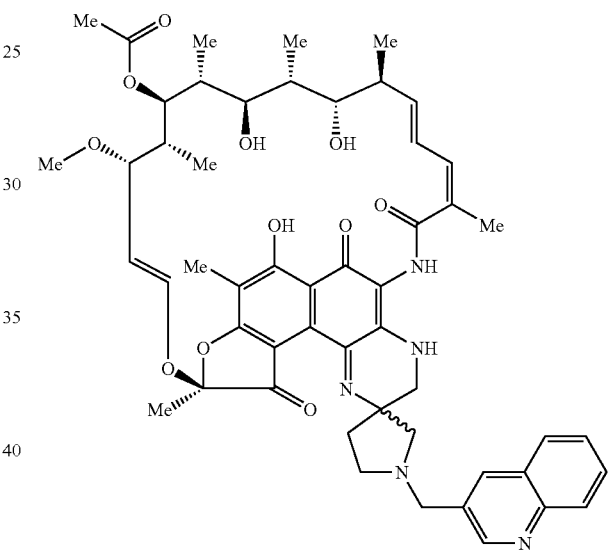

Synthesis: Step 1. 2,2,2-Trifluoro-N-{1-quinolin-3-ylmethyl-3-[(2,2,2-trifluoro-acetylamino)-methyl]-pyrrolidin-3-yl}-acetamide: To a cold (0° C.) solution of 3-(2,2,2-trifluoro-acetylamino)-3-[(2,2,2-trifluoro-acetylamino)-methyl]-pyrrolidinium chloride (490 mg, 1.43 mmol) in methanol (4 mL) was added 3-quinolinecarboxaldehyde (225 mg, 1.43 mmol) and NaOAc (352 mg, 4.29 mmol) and the mixture was stirred for 5 min, followed by the addition of AcOH (0.08 mL, 1.43 mmol) and NaCNBH$_3$ (108 mg, 1.72 mmol) and the reaction mixture was stirred for 4 h at 0° C. The methanol was removed under reduced pressure and the residue was diluted with ethyl acetate and washed with water and saturated NaHCO$_3$. The organic layer was dried over MgSO$_4$, filtered and evaporated to give 405 mg of the desired product that was used without further purification.

Step 2. 3-Aminomethyl-1-quinolin-3-ylmethyl-pyrrolidin-3-ylamine: The solution of 2,2,2-trifluoro-N-{1-quinolin-3-ylmethyl-3-[(2,2,2-trifluoro-acetylamino)-methyl]-pyrrolidin-3-yl}-acetamide (405 mg, 1.2 mmol) in 7 N NH$_3$ in MeOH (13 mL) was refluxed overnight in a sealed tube. The reaction mixture was cooled to room temperature and evaporated to give 400 mg of the desired diamine that was used without further purification.

Step 3. Spiro[N-(quinolin-3-ylmethyl)-pyrrolidine-3,4-piperazinorifamycin S]: To a solution of crude 3-aminomethyl-1-quinolin-3-ylmethyl-pyrrolidin-3-ylamine (400 mg) in dioxane/$H_2O$ (4/1) (3 mL) were added $K_3Fe(CN)_6$ (63 mg, 0.19 mmol) and 3-bromorifamycin S (150 mg, 0.19 mmol) and the reaction mixture was stirred overnight at room temperature. The reaction mixture was cooled to 0° C. and quenched with saturated $NH_4Cl$. The mixture was diluted with ethyl acetate and washed with saturated $NH_4Cl$ and saturated brine. The organic layer was dried over $Na_2SO_4$, filtered and evaporated. The residue was purified with preparative thin layer chromatography (methylene chloride:methanol:AcOH=200:10:0.4) to give the desired product (6.8 mg, 3.8%) as a dark red solid in 1:2 diasteromeric mixture. ESI MS m/z 932 (M+H$^+$); $^1$H NMR (400 MHz, CDCl$_3$) δ 13.83 (s, 1/3H), 13.81 (s, 2/3H), 9.00 (s, 1/3H), 8.90 (s, 2/3H), 8.26–8.09 (m, 3H), 7.90–7.80 (m, 1H), 7.75–7.69 (m, 1H), 7.58–7.53 (m, 1H), 7.36 (s, 2/3H), 7.33 (s, 1/3H), 6.48–6.42 (m, 1H), 6.27–6.23 (m, 1H), 6.13–6.07 (m, 1H), 6.03 (d, J=12.4 Hz, 2/3H), 6.01 (d, J=12.8 Hz, 1/3H), 5.09 (dd, J=12.4 Hz and 6.0 Hz, 2/3H), 5.06 (dd, J=12.4 Hz and 6.0 Hz, 1/3H), 4.99 (dd, J=10.4 Hz, 1H), 3.96–3.58 (m, 6H), 3.39 (d, J=5.2 Hz, 1H), 3.22–3.16 (m, 2H), 3.06 (s, 3H), 3.06–3.03 (m, 2H), 2.86–2.84 (m, 2H), 2.40–2.36 (m, 1H), 2.25 (s, 3H), 2.09 (s, 3H), 2.09–2.00 (m, 1H), 2.04 (s, 3H), 2.03 (s, 3H), 1.80–1.65 (m, 2H), 1.75 (s, 3H), 1.04 (d, J=6.8 Hz, 3H), 0.85 (d, J=6.8 Hz, 2H), 0.84 (d, J=6.8 Hz, 1H), 0.66 (d, J=6.8 Hz, 2H), 0.65 (d, J=6.8 Hz, 1H), 0.02 (d, J=6.8 Hz, 2H), 0.01 (d, J=6.8 Hz, 1H).

EXAMPLE 20

Spiro[N-Boc-pyrrolidine-3,4-piperazinorifamycin S]

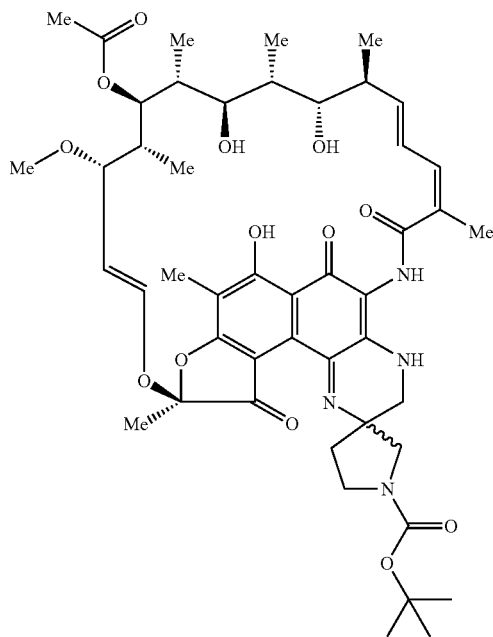

Synthesis: Step 1. 3-Amino-3-aminomethyl-pyrrolidine-1-carboxylic acid tert-butyl ester: A solution of 3-aminomethyl-3-(2,2,2-trifluoro-acetylamino)-pyrrolidine-1-carboxylic acid tert-butyl ester (600 mg, 1.9 mmol) in 10% $K_2CO_3$ in MeOH/$H_2O$ (5/2) (4 mL) was refluxed overnight. The reaction mixture was cooled to room temperature and evaporated. The residue was dissolved in ethyl acetate and washed with water and saturated brine. The organic layer was dried over $MgSO_4$, filtered and evaporated to give 350 mg of the desired diamine that was used without further purification.

Step 2. Spiro[N-Boc-pyrrolidine-3,4-piperazinorifamycin S]: To a solution of crude 3-amino-3-aminomethyl-pyrrolidine-1-carboxylic acid tert-butyl ester (350 mg) in dioxane/$H_2O$ (4/1) (2 mL) were added $K_3Fe(CN)_6$ (63 mg, 0.19 mmol) and 3-bromorifamycin S (150 mg, 0.19 mmol) and the reaction mixture was stirred overnight at room temperature. The reaction mixture was cooled to 0° C. and quenched with saturated $NH_4Cl$. The mixture was diluted with ethyl acetate and washed with saturated $NH_4Cl$ and saturated brine. The organic layer was dried over $Na_2SO_4$, filtered and evaporated. The residue was purified with preparative thin layer chromatography (hexanes:ethyl acetate:AcOH=100:100:1) to give the desired product (8 mg, 4.7%) as a dark red solid in 1:1 diasteromeric mixture. ESI MS m/z 891 (M+H$^+$); $^1$H NMR (400 MHz, CDCl$_3$) δ 13.72 (s, 1/2H), 13.65 (s, 1/2H), 8.24 (s, 1/2H), 8.21 (s, 1/2H), 7.61 (s, 1/2H), 7.42 (s, 1/2H), 6.45 (dd, J=10.8 Hz and 16.0 Hz, 1H), 6.23 (d, J=10.4 Hz, 1H), 6.11–5.99 (m, 2H), 5.05 (dd, J=12.4 Hz and 6.0 Hz, 1H), 4.93 (d, J=10.8 Hz, 1H), 3.83–3.24 (m, 8H), 3.04 (s, 3H), 3.05–3.00 (m, 1H), 2.64 (m, 1H), 2.35 (m, 1H), 2.09–1.29 (m, 6H), 2.05 (s, 6H), 2.00 (s, 3H), 1.69 (s, 3H), 1.43 (s, 9/2H), 1.39 (s, 9/2H), 1.01 (d, J=6.8 Hz, 3/2H), 1.00 (d, J=7.2 Hz, 3/2H), 0.82 (d, J=6.8 Hz, 3H), 0.63 (d, J=6.8 Hz, 3H), 0.01 (d, J=7.2 Hz, 3H).

REFERENCES CITED

The content of each of the following documents is hereby incorporated by reference.

U.S. Patent Documents

U.S. Pat. No. 4,219,478
U.S. Pat. No. 4,341,785
U.S. Pat. No. 4,690,919
U.S. Pat. No. 4,859,661
U.S. Pat. No. 4,965,261
U.S. Pat. No. 4,983,602

Other Publications

Farr, B. M. Rifamycins, in *Principles and Practice of Infectious Diseases*; Mandell, G. L., Bennett, J. E., Dolin, R., Eds.; Churchhill Livingstone: Philadelphia, pp. 348–361.

March, E., Montecchi, L., Venturini, A. P., Mascellani, G., Brufani, M. *J. Med. Chem.* Vol. 28, pp. 960–63, 1985.

National Committee for Clinical Laboratory Standards, 2000, Methods for dilution antimicrobial susceptibility tests for bacteria that grow aerobically, 5th ed. M$_7$-A5, Wayne, Pa.

What is claimed is:

1. A compound having a structure of Formula I:

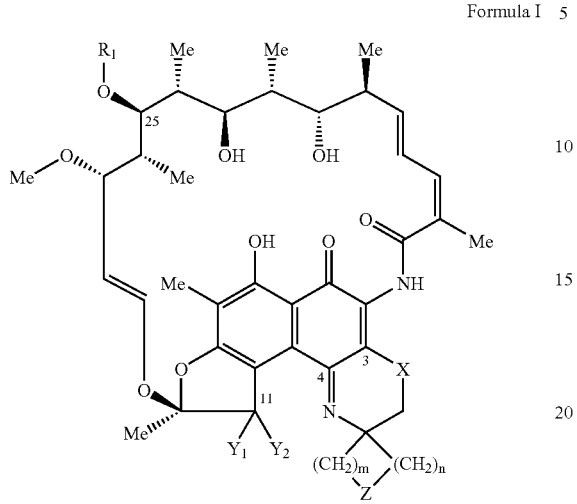

Formula I wherein,
R$_1$ is hydrogen, (C$_1$–C$_6$)alkyl, substituted (C$_1$–C$_6$)alkyl, —C(O)CH$_2$R$_{10}$, or —C(O)NR$_{11}$R$_{12}$,
wherein R$_{10}$ is hydrogen, halogen, hydroxyl, amino, (C$_1$–C$_6$)alkyl, (C$_1$–C$_6$)alkoxy, (C$_1$–C$_6$)alkylthio, (C$_1$–C$_6$)acyloxy, (C$_1$–C$_6$)alkylamino, di(C$_{1–6}$)alkylamino, aryl, heteroaryl, or -L$_{25}$-Q$_{25}$,
wherein L$_{25}$ is a linker group and Q$_{25}$ is an antibacterial pharmacophore selected from quinolones, macrolides, oxazolidinones, and β-lactams, and
wherein R$_{11}$ and R$_{12}$ independently are the same or different and are hydrogen, (C$_1$–C$_6$)alkyl, substituted (C$_1$–C$_6$)alkyl, or -L$_{25}$-Q$_{25}$, or
R$_{11}$ and R$_{12}$, together with the nitrogen atom to which they are attached, form a 3-to 8-membered heterocyclic ring, optionally containing up to two heteroatoms, wherein one or more of the carbon or nitrogen atoms of the heterocyclic ring is optionally substituted by (C$_1$–C$_6$)alkyl or -L$_{25}$-Q$_{25}$;
one of Y$_1$ and Y$_2$ is —OH and the other is hydrogen, or Y$_1$ and Y$_2$ together with the carbon to which they are attached are C═O or C═N—O—R$_{21}$,
wherein R$_{21}$ is hydrogen, (C$_1$–C$_6$)alkyl or -L$_{11}$-Q$_{11}$,
wherein L$_{11}$ is a linker group and Q$_{11}$ is an antibacterial pharmacophore selected from quinolones, macrolides, oxazolidinones, and β-lactams;
X is —CR$_{31}$R$_{32}$—, —NR$_{33}$—, —S— or —O—,
wherein R$_{31}$, R$_{32}$ and R$_{33}$ independently are the same or different and are hydrogen or (C$_1$–C$_6$)alkyl, and
m and n independently are the same or different and are an integer between 1 and 3; and
Z is —NR$_{41}$—, —CR$_{42}$R$_{43}$—, —O—, or —S(O)$_p$—,
wherein p is an integer between 0 and 2,
R$_{41}$ is hydrogen, (C$_1$–C$_6$)alkyl, (C$_1$–C$_6$)alkyl sulfonyl, aryl sulfonyl, (C$_1$–C$_6$)alkoxycarbonyl, aryloxycarbonyl, (C$_1$–C$_6$)alkyl amino carbonyl, aryl amino carbonyl, which are all optionally substituted, or -L-Q,
wherein L is a linker group comprising any combination of from 1 to 5 groups selected from (C$_1$–C$_6$) alkylene, (C$_3$–C$_8$)cycloalkylene, arylene, heteroarylene, bivalent heterocyclic group containing 1 to 3 heteroatoms, —C(═O)—, —C(═N—(O)—R$_{13}$)—, —C═N—, —O—, —S(O)$_n$—, and —N(R$_{14}$)—,
wherein n is an integer between 0 and 2, the carbon or nitrogen atoms of the linker group are optionally substituted by 1 to 3 substituents selected from (C$_1$–C$_6$)alkyl, amino, (C$_1$–C$_6$)alkylamino, di(C$_1$–C$_6$)alkylamino, hydroxyl, (C$_1$–C$_6$)alkoxy, and heterocyclic group, R$_{13}$ and R$_{14}$ are independently the same or different and are hydrogen, (C$_1$–C$_6$)alkyl, aryl, heteroaryl, or heterocyclic group, and Q is an antibacterial pharmacophore selected from quinolones, macrolides, oxazolidinones, and β-lactams, and
R$_{42}$ and R$_{43}$ independently are the same or different and are hydrogen, hydroxyl, amino, carboxyl, halo, cyano, (C$_1$–C$_6$)alkyl, (C$_3$–C$_6$)cycloalkyl, (C$_1$–C$_6$) heteroaryl, or heterocyclic group.

2. The compound of claim 1, wherein L, L$_{11}$, and L$_{25}$ independently are the same or different and comprise any combination of from one to three of the following structures:

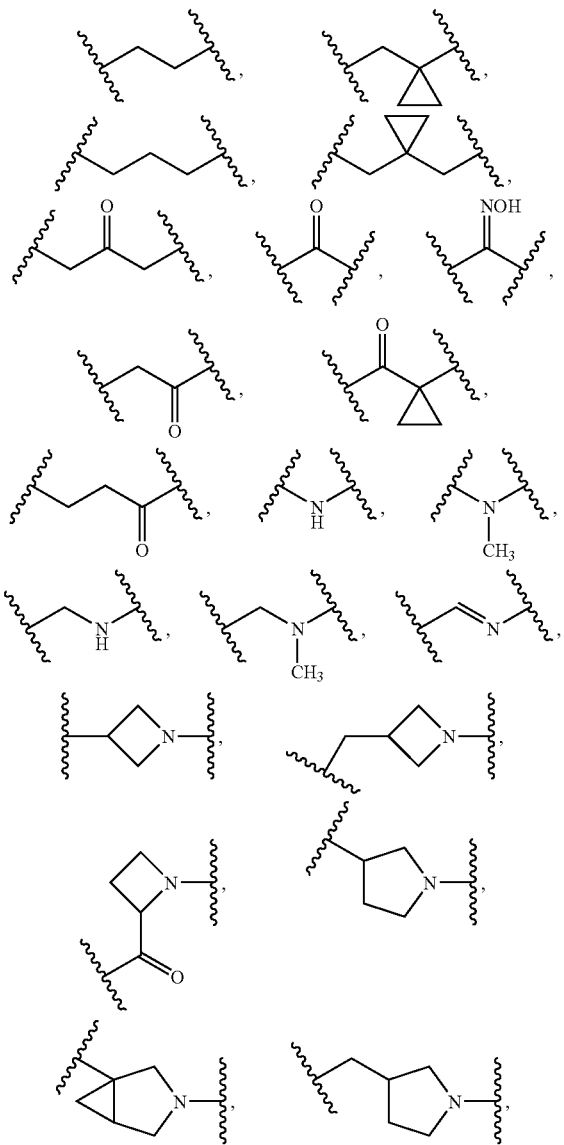

-continued

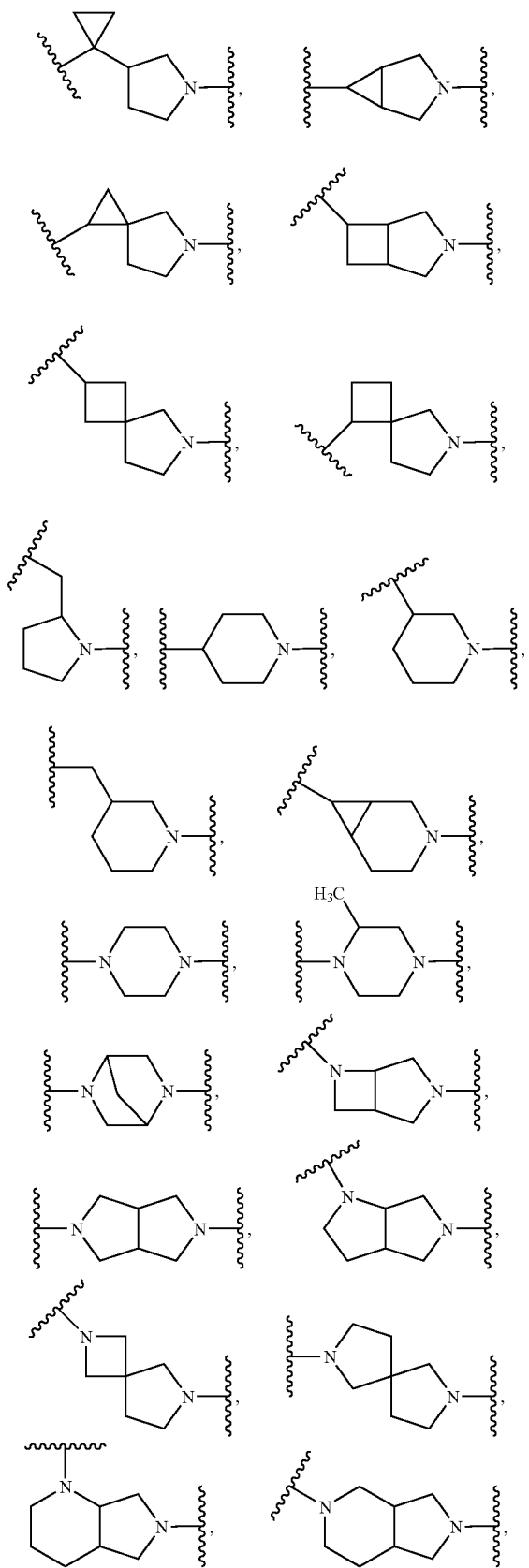

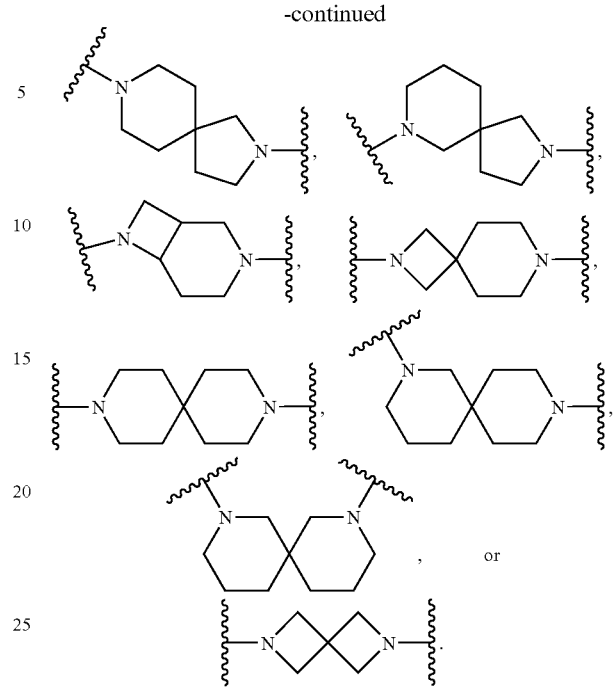

3. A method of treating a bacterial infection in a subject comprising: administering to the subject an effective amount of the compound of claim 1.

4. The method of claim 3, wherein the bacterial infection is caused by a drug-resistant bacterium.

5. A compound having a structure of Formula II:

Formula II

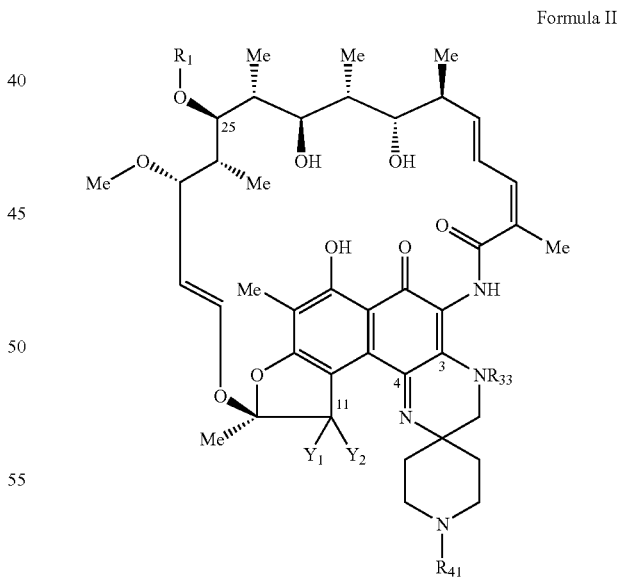

wherein, $R_1$ is hydrogen, $(C_1–C_6)$alkyl, substituted $(C_{1–6})$alkyl, —C(O)CH$_2$R$_{10}$, or —C(O)NR$_{11}$R$_{12}$, wherein $R_{10}$ is hydrogen, halogen, hydroxyl, amino, $(C_1–C_6)$alkyl, $(C_1–C_6)$alkoxy, $(C_1–C_6)$alkylthio, $(C_1–C_6)$acyloxy, i -C6)alkylamino, di(C$_1$–C6)alkylamino, aryl, heteroaryl, or -L$_{25}$-Q$_{25}$, wherein L$_{25}$ is a linker group and Q$_{25}$ is an antibacterial pharmacophore selected from quinolones, macrolides, oxazolidinones, and β-lactams, and wherein R$_{11}$ and R$_{12}$ independently are the same or different and are hydrogen, (C$_1$–C$_6$)alkyl, substituted (C$_1$–C$_6$)alkyl, or -L$_{25}$-Q$_{25}$, or R$_{11}$ and R$_{12}$, together with the nitrogen atom to which they are attached, form a 3- to 8-membered heterocyclic ring, optionally containing up to two heteroatoms, wherein one or more of the carbon or nitrogen atoms of the heterocyclic ring is optionally substituted by (C$_1$–C$_6$)alkyl or -L$_{25}$-Q$_{25}$;

one of Y$_1$ and Y$_2$ is —OH and the other is hydrogen, or Y$_1$ and Y$_2$ together with the carbon to which they are attached form C=O or CN=O—R$_{21}$, wherein R$_{21}$ is hydrogen, (C$_1$–C$_6$)alkyl or -L$_{11}$-Q$_{11}$, wherein L$_{11}$ is a linker group and Q$_{11}$ is an antibacterial pharmacophore selected from quinolones, macrolides, oxazolidinones, and β-lactams;

R$_{33}$ is hydrogen or (C$_1$–C$_6$)alkyl;

R$_{41}$ is hydrogen, (C$_1$–C$_6$)alkyl, (C$_1$–C$_6$)alkyl sulfonyl, aryl sulfonyl, (C$_1$–C$_6$)alkoxycarbonyl, aryloxycarbonyl, (C$_1$–C$_6$)alkyl amino carbonyl, aryl amino carbonyl, which are all optionally substituted, or -L-Q, wherein L is a linker group comprising any combination of from 1 to 5 groups selected from (C$_1$–C$_6$) alkylene, (C$_3$–C$_8$)cycloalkylene, arylene, heteroarylene, bivalent heterocyclic group containing 1 to 3 heteroatoms, —C(=O)—, —C(=N—O—R$_{13}$)—, —C=N, —O—, —S(O)$_n$—, and —N(R$_{14}$)—, wherein n is an integer between 0 and 2, the carbon or nitrogen atoms of the linker group are optionally substituted by 1 to 3 substituents selected from (C$_1$–C$_6$)alkyl, amino, (C$_1$–C6)alkylamino, di(C$_1$–C6)alkylamino, hydroxyl, (C$_1$–C$_6$)alkoxy, and heterocyclic group, R$_{13}$ and R$_{14}$ are independently the same or different and are hydrogen, (C$_1$–C$_6$)alkyl, aryl, heteroaryl, or heterocyclic group, and Q is an antibacterial pharmacophore selected from quinolones, macrolides, oxazolidinones, and β-lactams.

6. The compound of claim 5, wherein L, L$_{11}$, and L$_{25}$ independently are the same or different and comprise any combination of from one to three of the following structures:

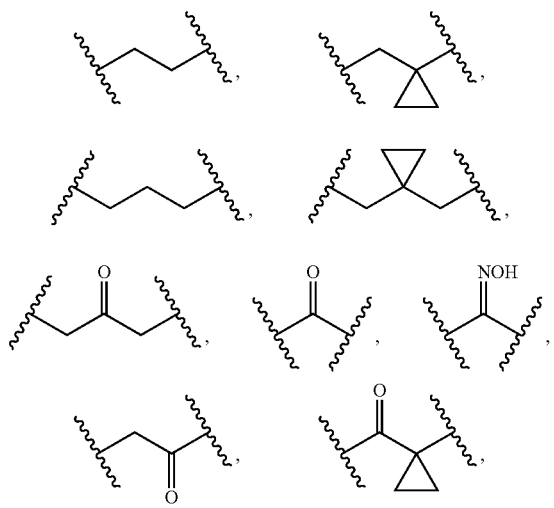

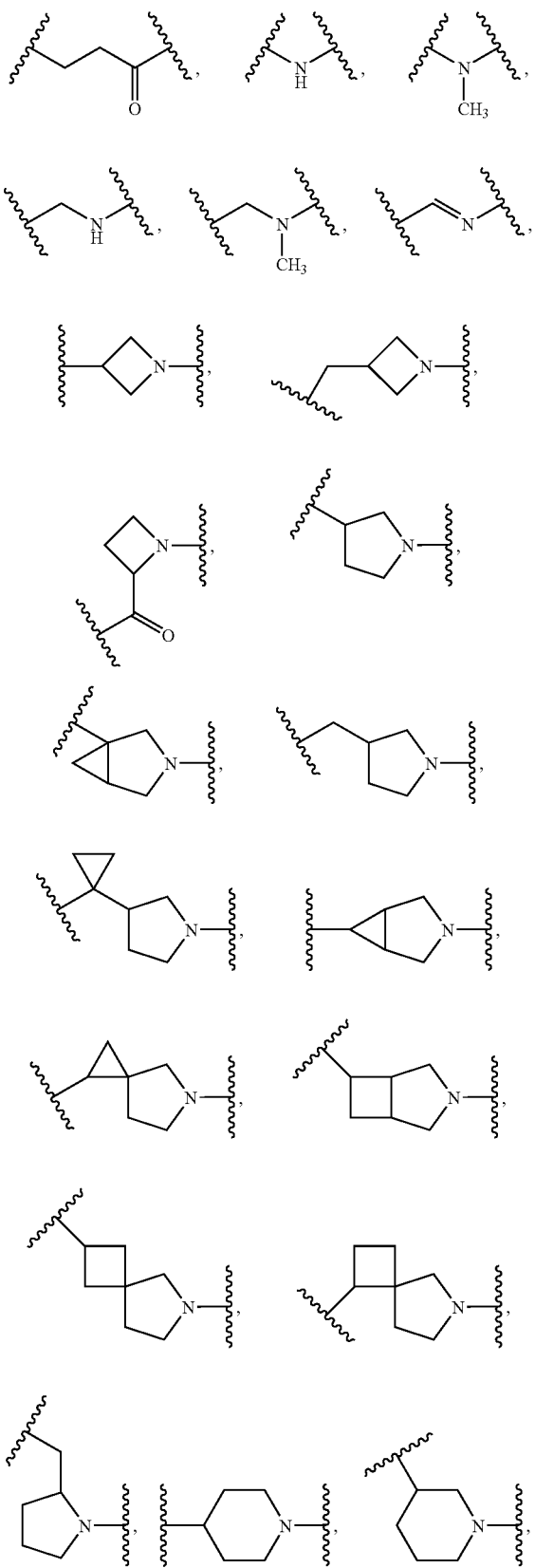

49

-continued

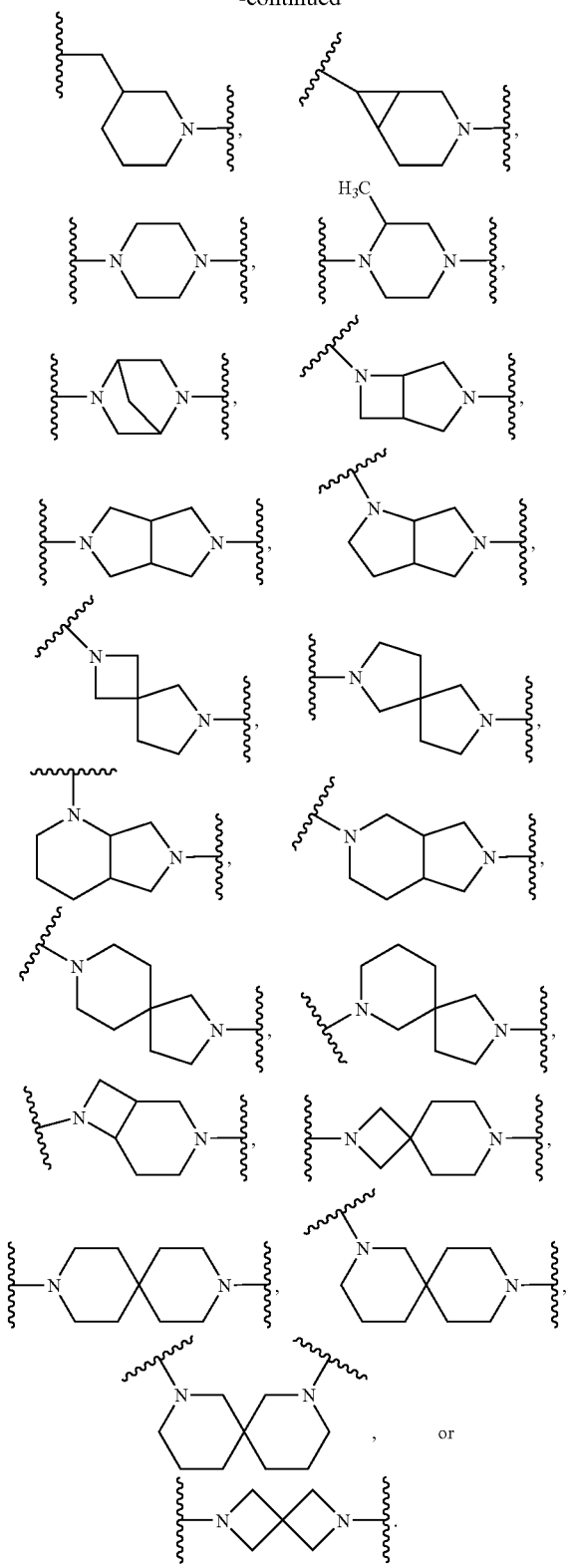

7. A method of treating a bacterial infection in a subject comprising: administering to the subject an effective amount of the compound of claim 5.

8. The method of claim 7, wherein the bacterial infection is caused by a drug-resistant bacterium.

50

9. A compound having a structure of Formula III:

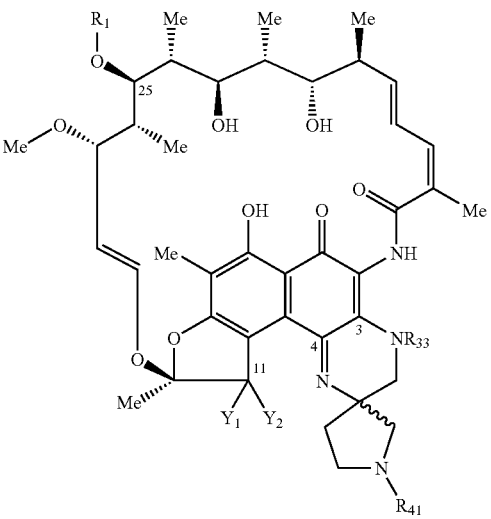

Formula III wherein, $R_1$ is hydrogen, $(C_1-C_6)$alkyl, substituted $(C_1-C_6)$alkyl, —C(O)CH$_2$R$_{10}$, or —C(O)NR$_{11}$ R$_{12}$,
  wherein $R_{10}$ is hydrogen, halogen, hydroxyl, amino, $(C_1-C_6)$alkyl, $(C_1-C_6)$alkoxy, $(C_1-C_6)$alkylthio, $(C_1-C_6)$acyloxy, i -C6)alkylamino, di$(C_1-C_6)$alkylamino, aryl, heteroaryl, or -L$_{25}$-Q$_{25}$,
    wherein $L_{25}$ is a linker group and $Q_{25}$ is an antibacterial pharmacophore selected from quinolones, macrolides, oxazolidinones, and β-lactams, and
  wherein $R_{11}$ and $R_{12}$ independently are the same or different and are hydrogen, $(C_1-C_6)$alkyl, substituted $(C_1-C_6)$alkyl, or -L$_{25}$-Q$_{25}$, or
  $R_{11}$ and $R_{12}$, together with the nitrogen atom to which they are attached, form a 3-to 8-membered heterocyclic ring, optionally containing up to two heteroatoms, wherein one or more of the carbon or nitrogen atoms of the heterocyclic ring is optionally substituted by $(C_1-C_6)$alkyl or -L$_{25}$-Q$_{25}$;

one of $Y_1$ and $Y_2$ is —OH and the other is hydrogen, or $Y_1$ and $Y_2$ together with the carbon to which they are attached form C=O or C=N—O—R$_{21}$,
  wherein $R_{21}$ is hydrogen, $(C_1-C_6)$alkyl or L$_{11}$-Q$_{11}$,
    wherein $L_{11}$ is a linker group and $Q_{11}$ is an antibacterial pharmacophore selected from quinolones, macrolides, oxazolidinones, and β-lactams;

$R_{33}$ is hydrogen or $(C_1-C_6)$alkyl; and $R_{41}$ is hydrogen, $(C_1-C_6)$alkyl, $(C_1-C_6)$alkyl sulfonyl, aryl sulfonyl, $(C_1-C_6)$alkoxycarbonyl, aryloxycarbonyl, $(C_1-C_6)$alkyl amino carbonyl, aryl amino carbonyl, which are all optionally substituted, or -L-Q,
  wherein L is a linker group comprising any combination of from 1 to 5 groups selected from $(C_1-C_6)$ alkylene, $(C_3-C_8)$cycloalkylene, arylene, heteroarylene, bivalent heterocyclic group containing 1 to 3 heteroatoms, —C(=O)—, —C(N=O—R$_{13}$)—, —C=N—, —O—, —S(O)$_n$—, and —N(R$_{14}$)—,
    wherein n is an integer between 0 and 2, the carbon or nitrogen atoms of the linker group are optionally substituted by 1 to 3 substituents selected from $(C_1-C_6)$alkyl, amino, $(C_1-C_6)$alkylamino, di($C_1$–$C_6$)alkylamino, hydroxyl, ($C_1$–$C_6$)alkoxy, and heterocyclic group, $R_{13}$ and $R_{14}$ are independently the same or different and are hydrogen, ($C_1$–$C_6$)alkyl, aryl, heteroaryl, or heterocyclic group, and Q is an antibacterial pharmacophore selected from quinolones, macrolides, oxazolidinones, and β-lactams.

10. The compound of claim 9, wherein L, $L_{11}$, and $L_{25}$ independently are the same or different and comprise any combination of from one to three of the following structures:

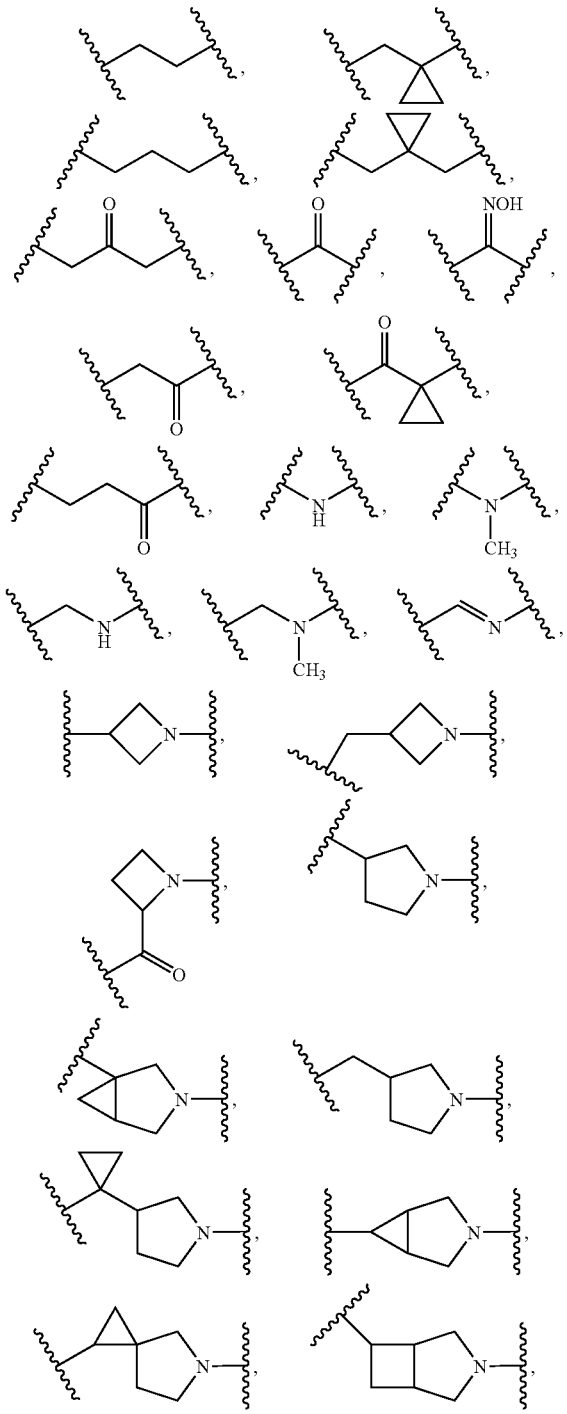

-continued

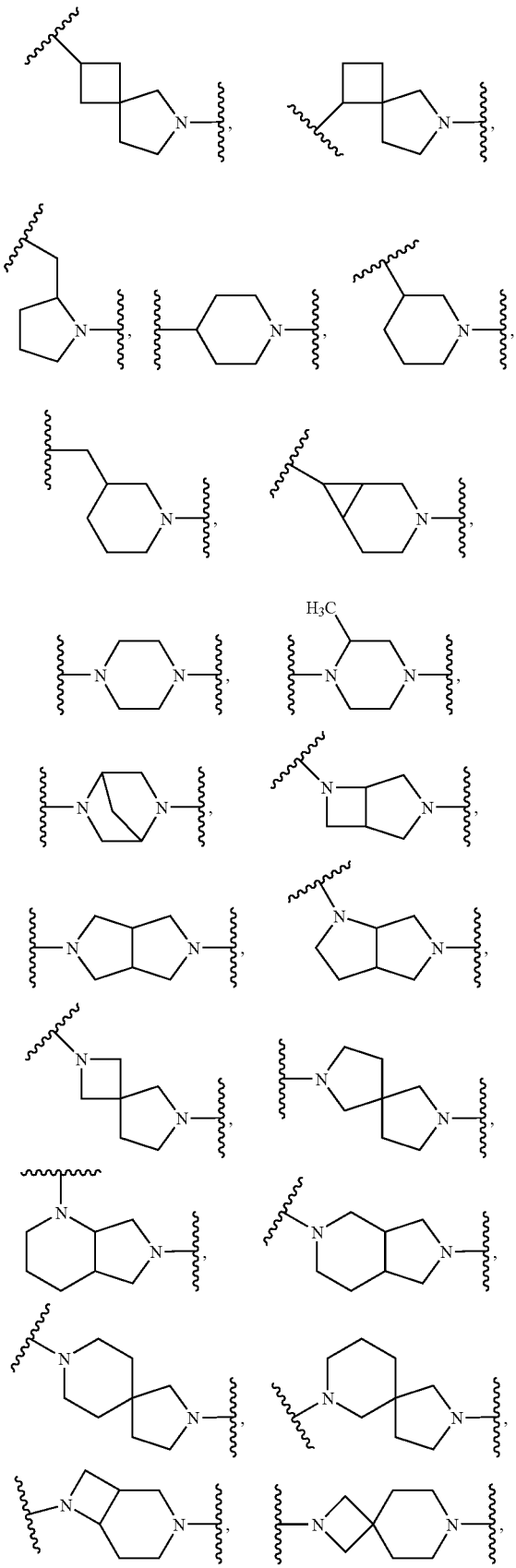

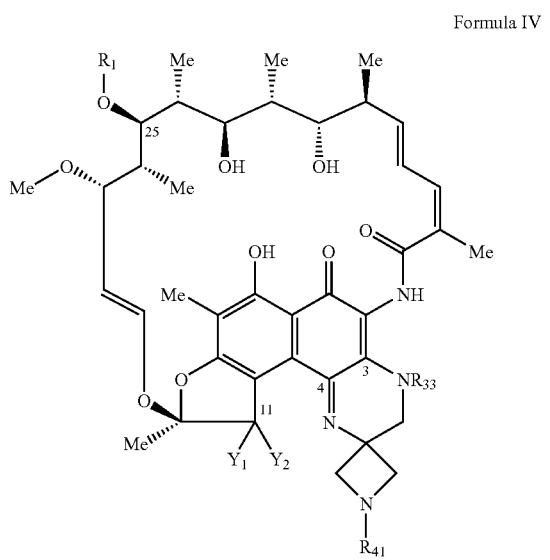

11. A method of treating a bacterial infection in a subject comprising: administering to the subject an effective amount of the compound of claim 9.

12. The method of claim 11, wherein the bacterial infection is caused by a drug-resistant bacterium.

13. A compound having a structure of Formula IV:

Formula IV wherein,
R$_1$ is hydrogen, (C$_1$–C$_6$)alkyl, substituted (C$_1$–C$_6$)alkyl, —C(O)CH$_2$R$_{10}$, or —C(O)NR$_{11}$R$_{12}$,
wherein R$_{10}$ is hydrogen, halogen, hydroxyl, amino, (C$_1$–C$_6$)alkyl, (C$_1$–C$_6$)alkoxy, (C$_1$–C$_6$)alkylthio, (C$_1$–C$_6$)acyloxy, (C$_1$–C$_6$)alkylamino, di(C$_{1≧C6}$)alkylamino, aryl, heteroaryl, or -L$_{25}$-Q$_{25}$,
wherein L$_{25}$ is a linker group and Q$_{25}$ is an antibacterial pharmacophore selected from quinolones, macrolides, oxazolidinones, and β-lactams, and
wherein R$_{11}$ and R$_{12}$ independently are the same or different and are hydrogen, (C$_1$–C$_6$)alkyl, substituted (C$_1$–C$_6$)alkyl, or -L$_{25}$-Q$_{25}$, or
R$_{11}$ and R$_{12}$, together with the nitrogen atom to which they are attached, form a 3-to 8-membered heterocyclic ring, optionally containing up to two heteroatoms, wherein one or more of the carbon or nitrogen atoms of the heterocyclic ring is optionally substituted by (C$_1$–C$_6$)alkyl or -L$_{25}$-Q$_{25}$;

one of Y$_1$ and Y$_2$ is —OH and the other is hydrogen, or Y$_1$ and Y$_2$ together with the carbon to which they are attached form C═O or C═N—O—R$_{21}$,
wherein R$_{21}$ is hydrogen, (C$_1$–C$_6$)alkyl or -L$_{11}$-Q$_{11}$,
wherein L$_{11}$ is a linker group and Q$_{11}$ is an antibacterial pharmacophore selected from quinolones, macrolides, oxazolidinones, and β-lactams;

R$_{33}$ is hydrogen or (C$_1$–C$_6$)alkyl;
R$_{41}$ is hydrogen, (C$_1$–C$_6$)alkyl, (C$_1$–C$_6$)alkyl sulfonyl, aryl sulfonyl, (C$_{1-6}$)alkoxycarbonyl, aryloxycarbonyl, (C$_1$–C$_6$)alkyl amino carbonyl, aryl amino carbonyl, which are all optionally substituted, or -L-Q,
wherein L is a linker group comprising any combination of from 1 to 5 groups selected from (C$_1$–C$_6$)alkylene, (C$_3$–C$_8$)cycloalkylene, arylene, heteroarylene, bivalent heterocyclic group containing 1 to 3 heteroatoms, —C(═O), —C(═N—O—R$_{13}$)—, —C═N—, —O—, —S(O)$_n$—, and —N(R$_{14}$)—,
wherein n is an integer between 0 and 2, the carbon or nitrogen atoms of the linker group are optionally substituted by 1 to 3 substituents selected from (C$_1$–C$_6$)alkyl, amino, (C$_1$–C$_6$)alkylamino, di(C$_1$–C$_6$)alkylamino, hydroxyl, (C$_1$–C$_6$)alkoxy, and heterocyclic group, R$_{13}$ and R$_{14}$ are independently the same or different and are hydrogen, (C$_1$–C$_6$)alkyl, aryl, heteroaryl, or heterocyclic group, and Q is an antibacterial pharmacophore selected from quinolones, macrolides, oxazolidinones, and β-lactams.

14. The compound of claim 13, wherein L, L$_{11}$, and L$_{25}$ independently are the same or different and comprise any combination of from one to three of the following structures:

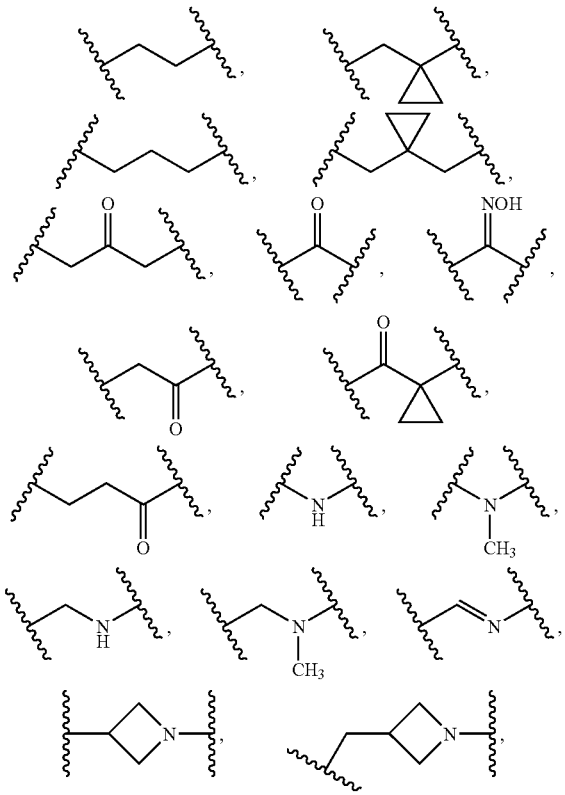

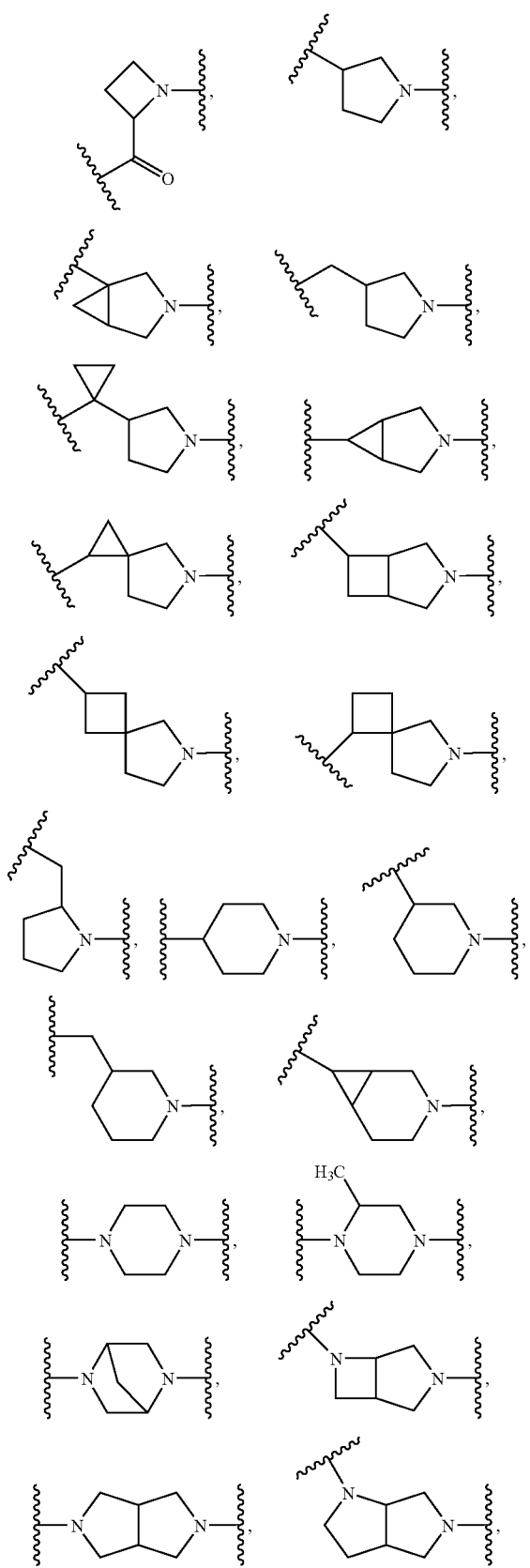
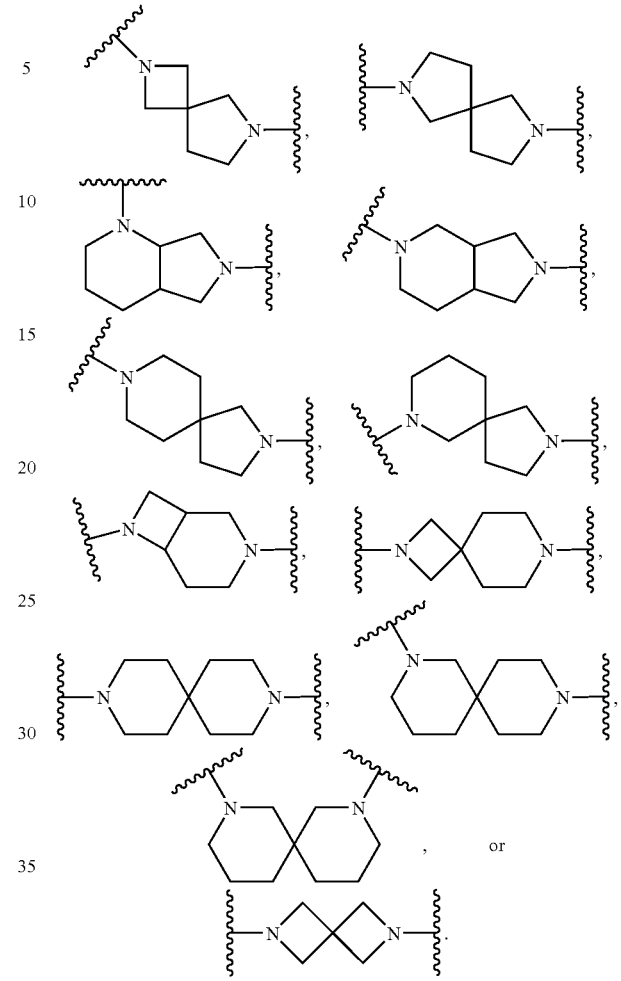
15. A method of treating a bacterial infection in a subject comprising: administering to the subject an effective amount of the compound of claim 13.
16. The method of claim 15, wherein the bacterial infection is caused by a drug-resistant bacterium.
17. A compound having the formula:
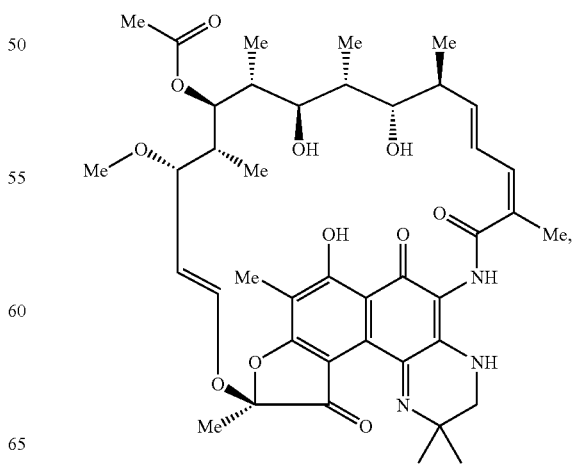

57
-continued
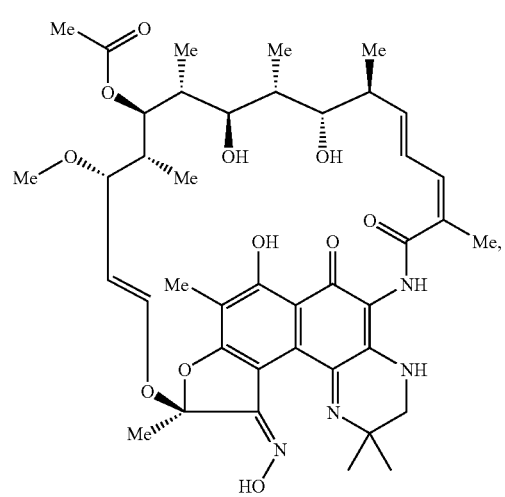
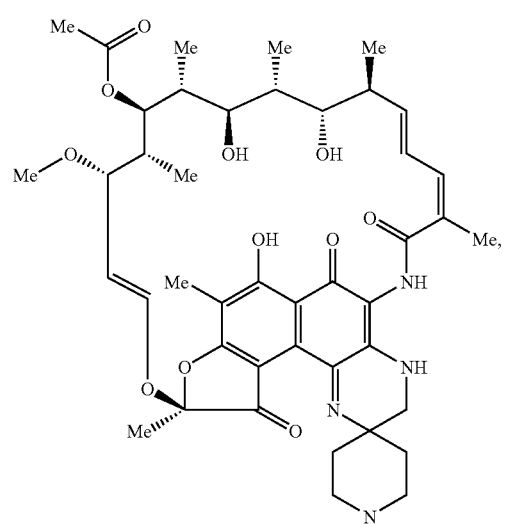
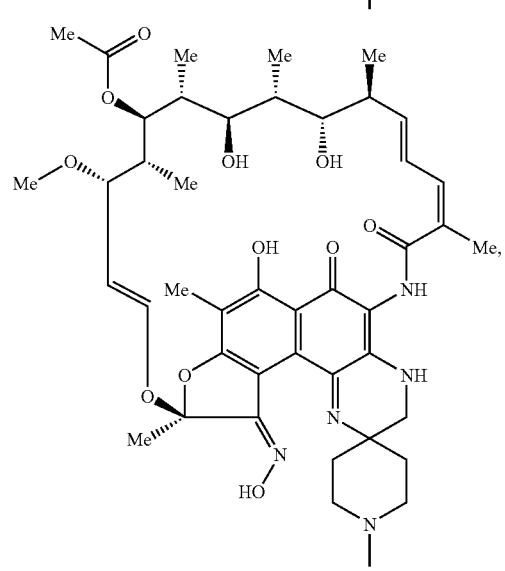
58
-continued
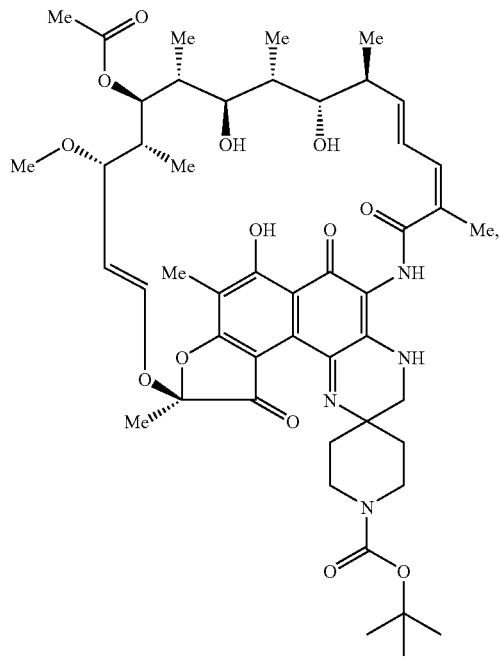
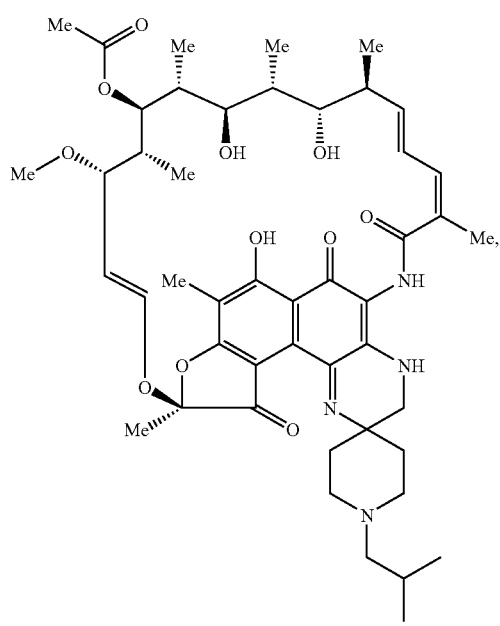

59
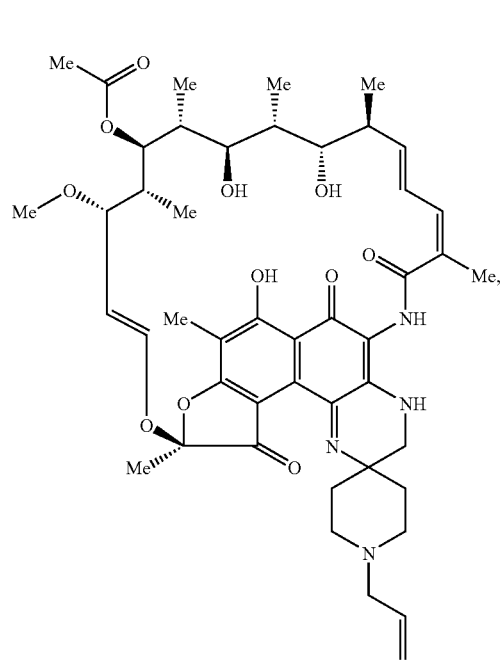
60
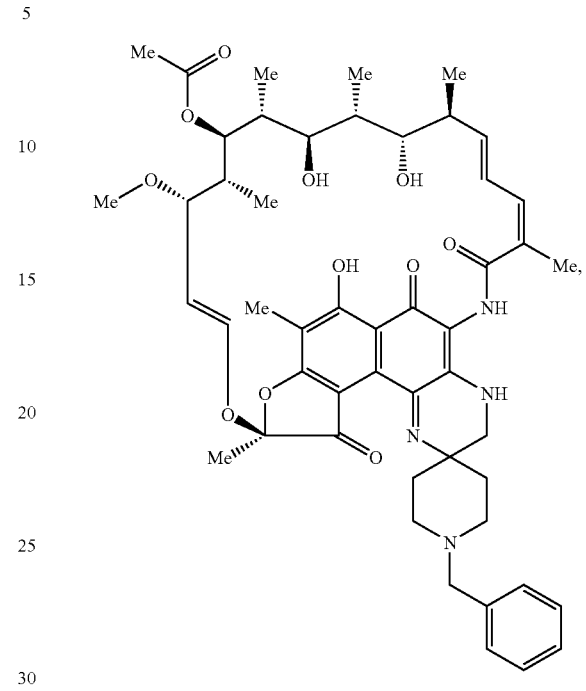
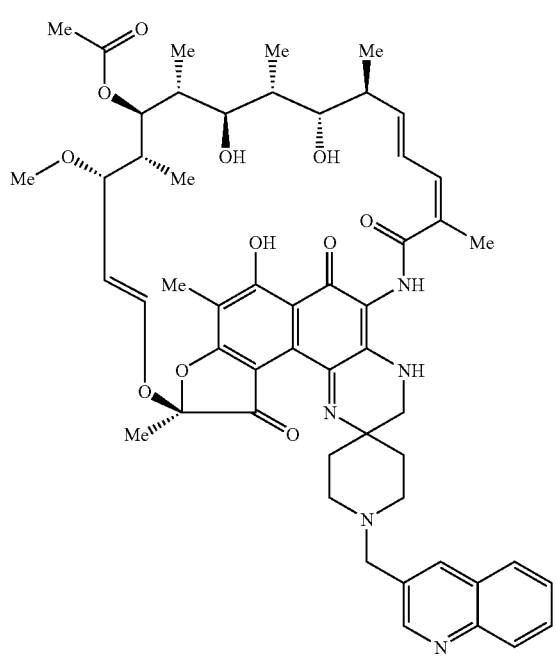
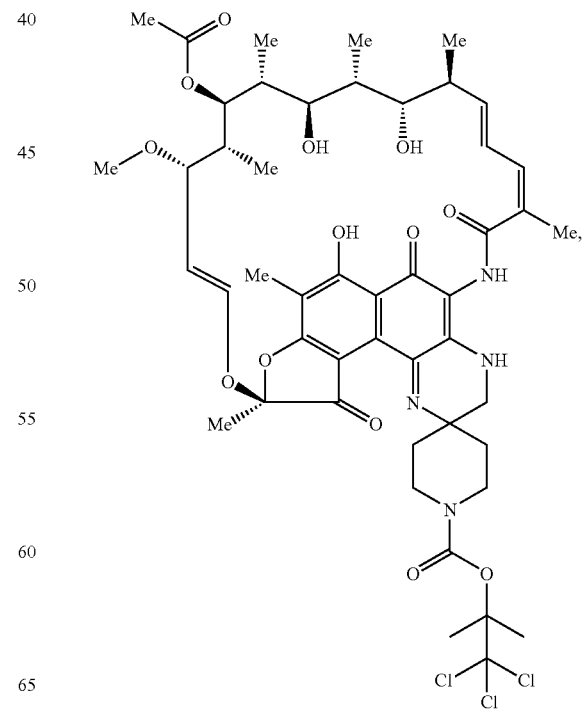

61
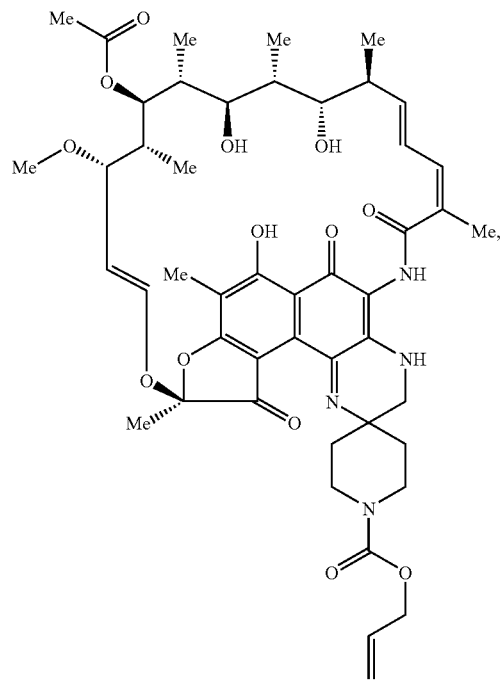
62
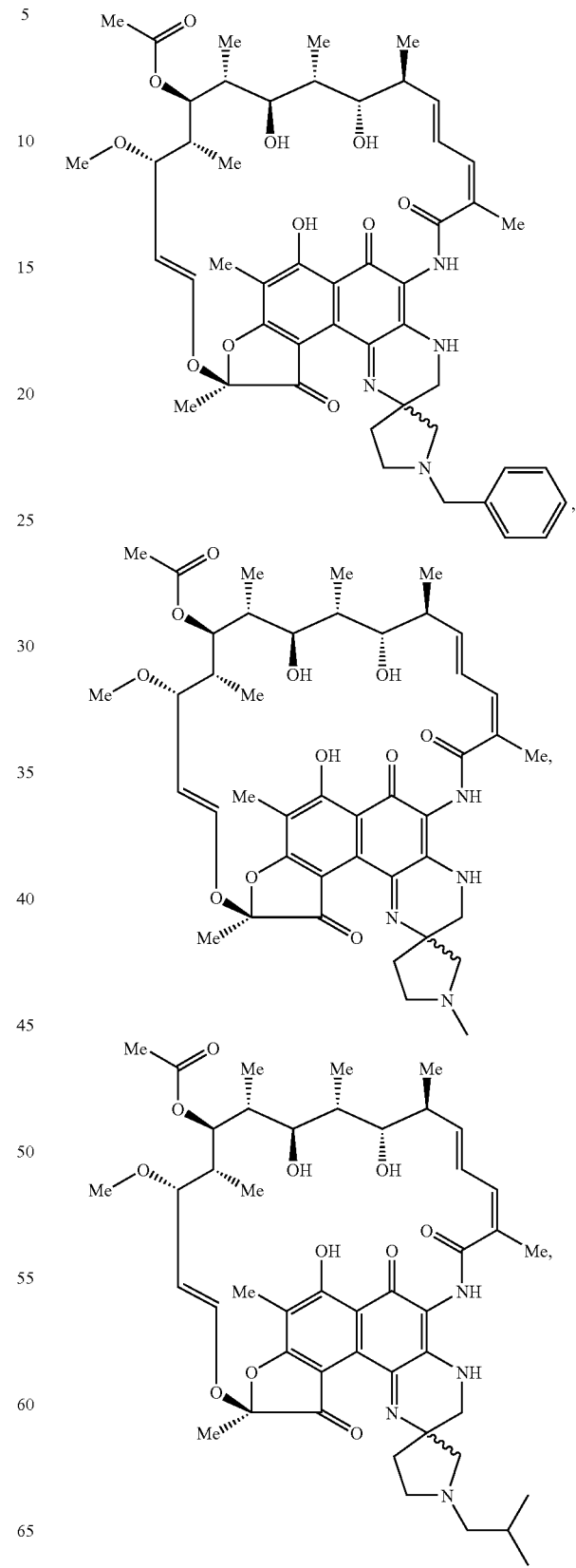

-continued
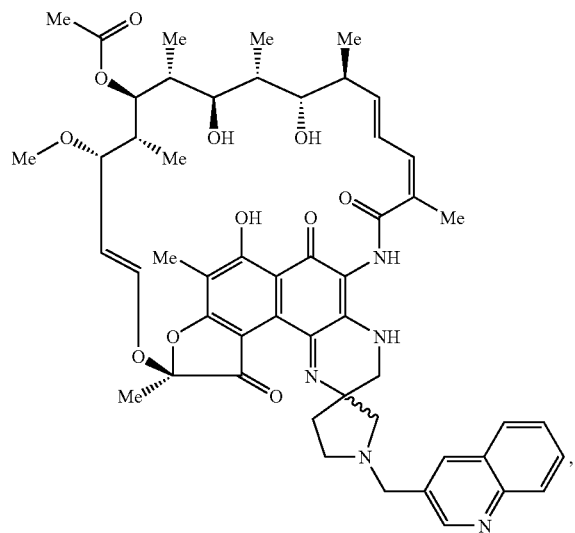
or
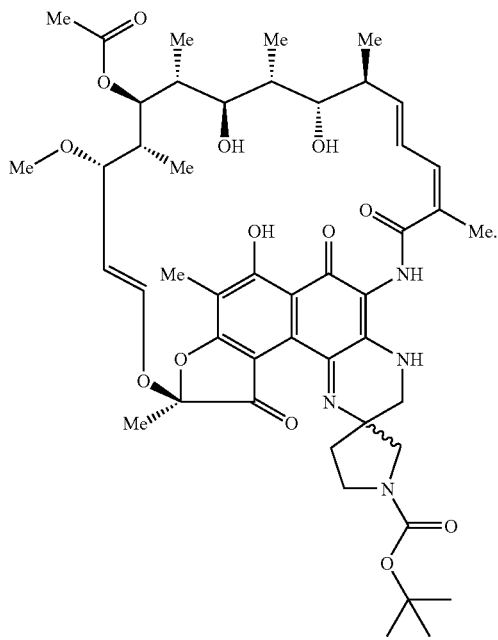
18. A compound having the formula 2',2'-Dimethyl-3,4-piperazinorifamycin S:
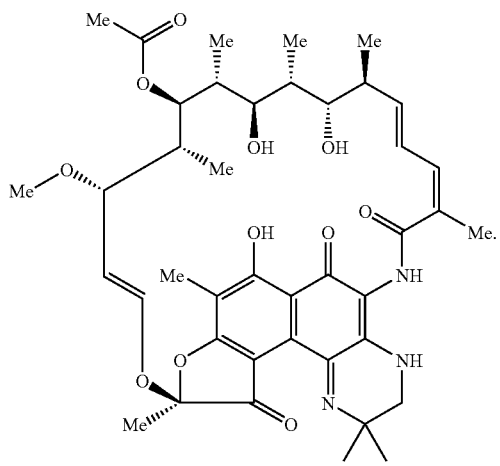
19. A compound having the formula 3,4-(2,2-Dimethyl-piperazino)-11-deoxy-11-hydroxyimino-rifamycin S:

20. A compound having the formula Spiro[N-methyl-piperidine-3,4-piperazinorifamycin S]:
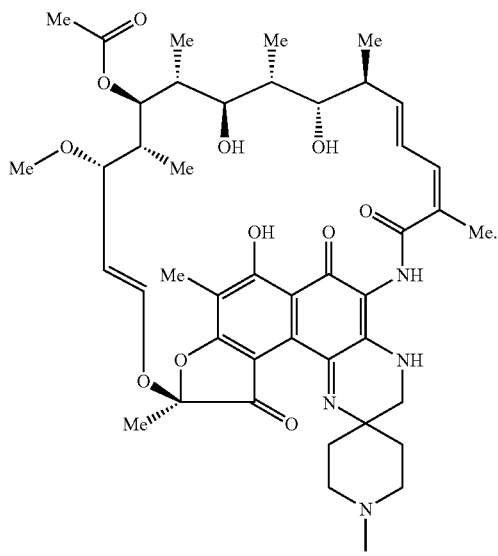
21. A compound having the formula Spiro[N-methyl-piperidine-3,4-piperazino-11-deoxy-11-hydroxyimino-rifamycin S]:
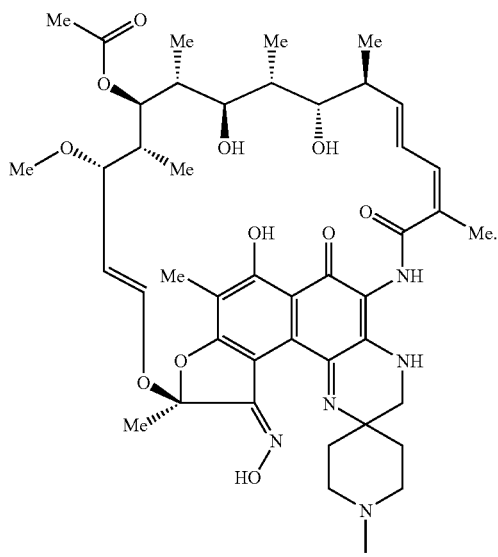
22. A compound having the formula [N-Boc-piperidine-3,4-piperazinorifamycin S]:
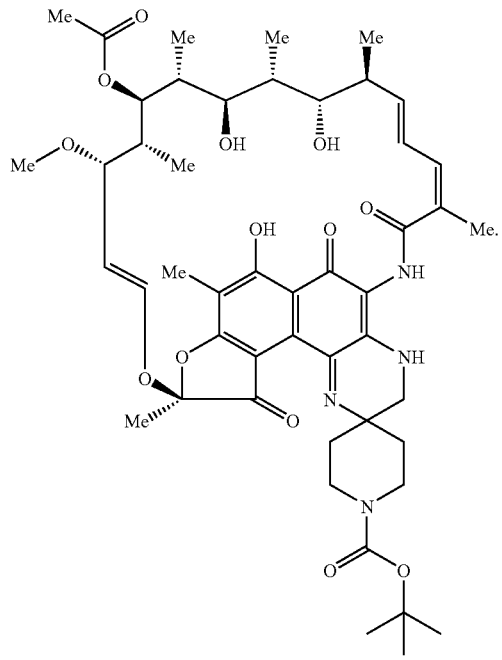
23. A compound having the formula Spiro[N-isobutyl-piperidine-3,4-piperazinorifamycin S]:
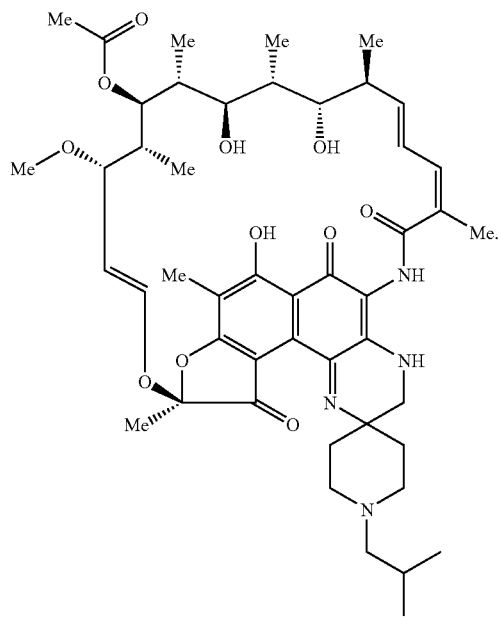

24. A compound having the formula Spiro [N-allyl-piperidine-3,4- piperazinorifamycin S]:

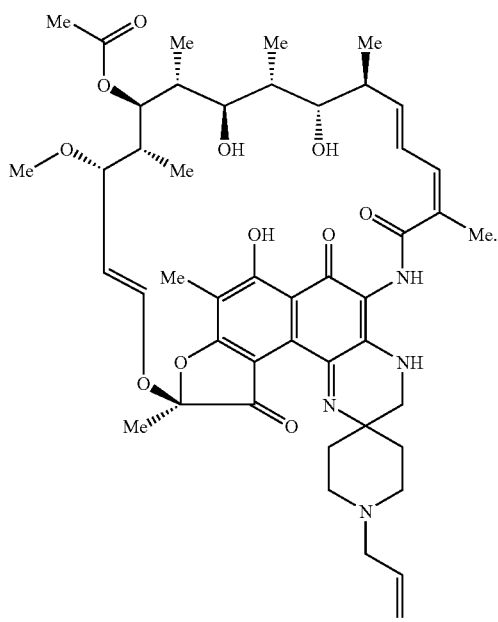

25. A compound having the formula Spiro[N-(quinolin-3-ylmethyl)-piperidine-3,4-piperazinorifamycin S]:

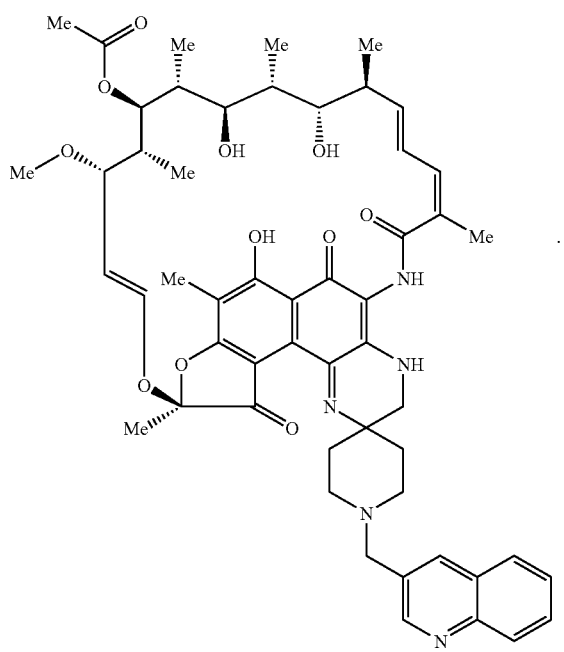

26. A compound having the formula Spiro[N-benzyl-piperidine-3,4-piperazinorifamycin S]:

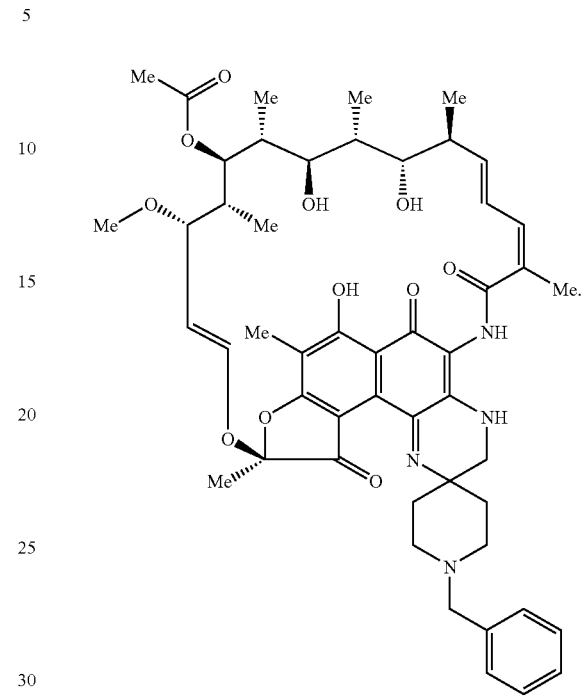

27. A compound having the formula Spiro[N-(2,2,2-trichloro-1,1-dimethyl-ethoxycarbonyl)-piperidine-3,4-piperazinorifamycin S]:

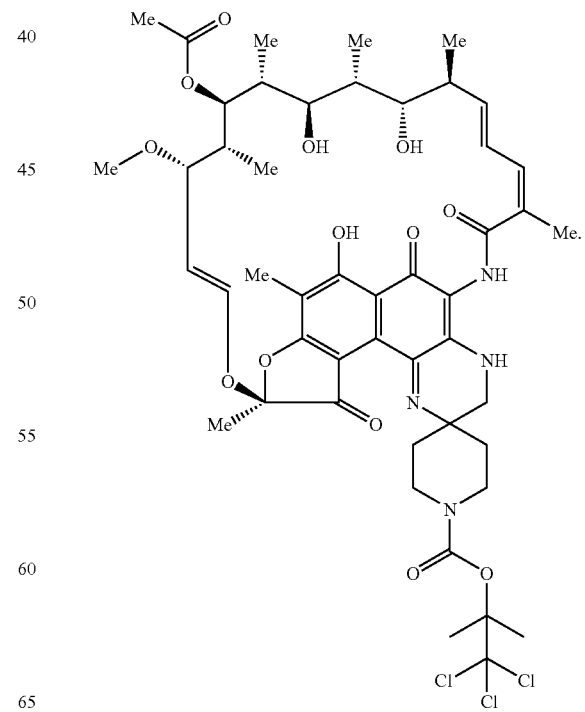

28. A compound having the formula Spiro[N-alloc-piperidine-3,4-piperazinorifamycin S]:

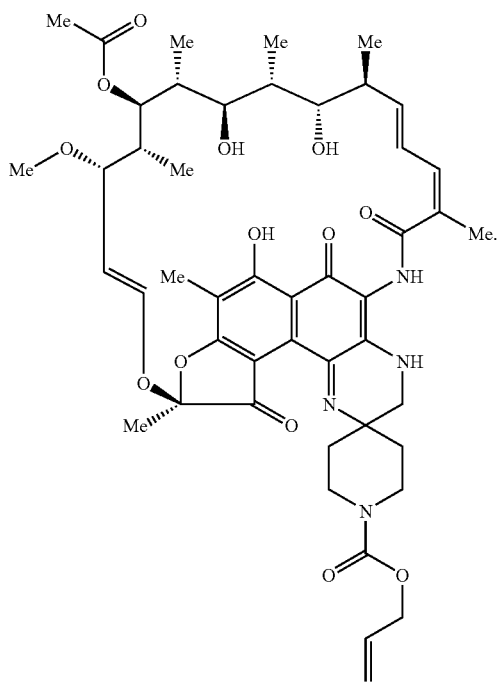

29. A compound having the formula Spiro[piperidine-3,4-piperazinorifamycin S]:

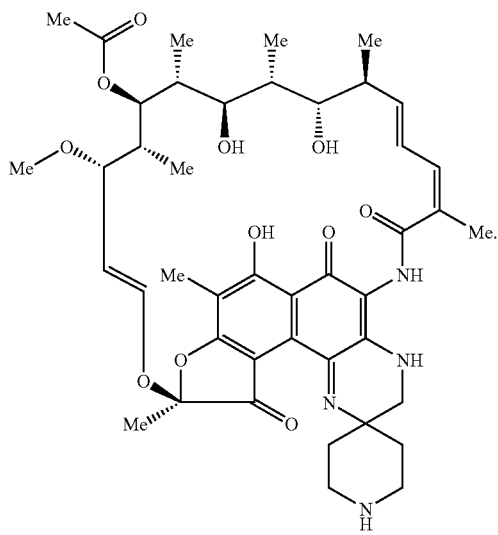

30. A compound having the formula Spiro[N-benzyl-pyrrolidine-3,4-piperazinorifamycin S]:

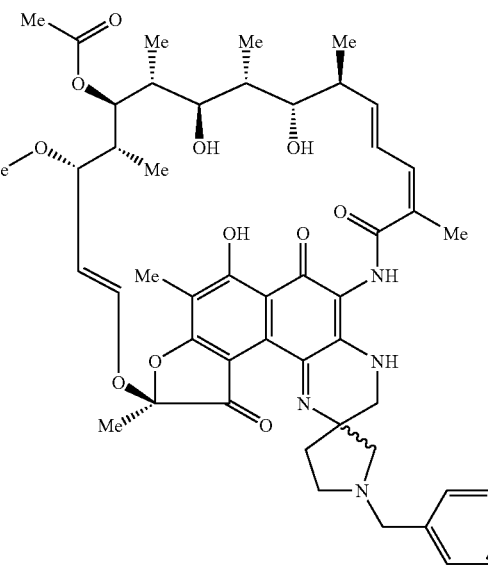

31. A compound having the formula Spiro [N-methyl-pyrrolidine-3,4-piperazinorifamycin S]:

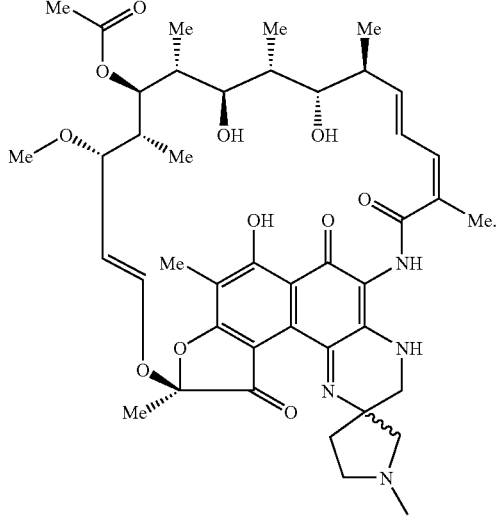

32. A compound having the formula Spiro[N-isobutyl-pyrrolidine-3,4-piperazinorifamycin S]:

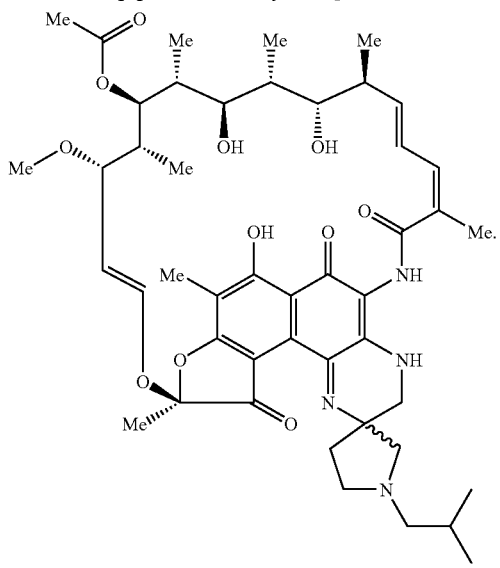

33. A compound having the formula Spiro[N-(quinolin-3-ylmethyl)-pyrrolidine-3,4-piperazinorifamycin S]:
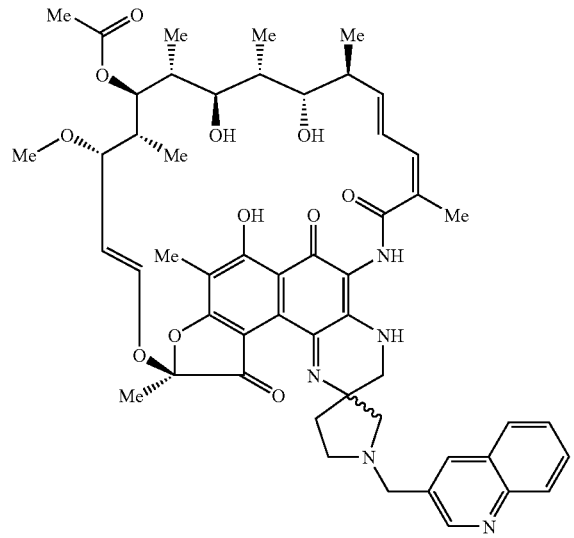
34. A compound having the formula Spiro[N-Boc-pyrrolidine-3,4-piperazinorifamycin S]:
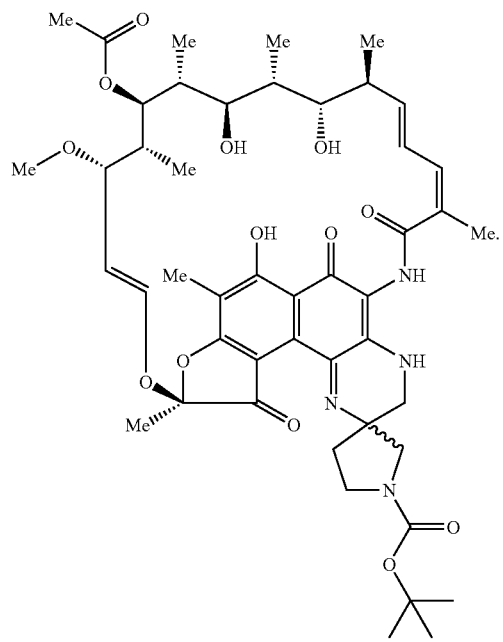
* * * * *